(12) United States Patent  
Suzuki et al.

(10) Patent No.: US 9,119,750 B2
(45) Date of Patent: Sep. 1, 2015

(54) ABSORBENT ARTICLE

(75) Inventors: Migaku Suzuki, Kanagawa (JP);
Katsumi Ando, Kanagawa (JP)

(73) Assignee: DAIO PAPER CORPORATION,
Ehime (JP)

( * ) Notice: Subject to any disclaimer, the term of this patent is extended or adjusted under 35 U.S.C. 154(b) by 346 days.

(21) Appl. No.: 12/448,206

(22) PCT Filed: Dec. 28, 2006

(86) PCT No.: PCT/JP2006/326274
§ 371 (c)(1),
(2), (4) Date: Jun. 12, 2009

(87) PCT Pub. No.: WO2008/081549
PCT Pub. Date: Jul. 10, 2008

(65) Prior Publication Data
US 2009/0270828 A1    Oct. 29, 2009

(51) Int. Cl.
*A61F 13/491* (2006.01)
*A61F 13/495* (2006.01)
*A61F 13/494* (2006.01)
*A61F 13/537* (2006.01)

(52) U.S. Cl.
CPC ........... *A61F 13/495* (2013.01); *A61F 13/4946* (2013.01); *A61F 13/49473* (2013.01); *A61F 13/53713* (2013.01); *A61F 13/53717* (2013.01); *A61F 2013/53782* (2013.01)

(58) Field of Classification Search
CPC .............. A61F 13/491; A61F 13/4915; A61F 2013/51195
USPC ........... 604/385.101, 385.09, 385.19, 385.01, 604/385.08
See application file for complete search history.

(56) References Cited

U.S. PATENT DOCUMENTS

| | | | | | |
|---|---|---|---|---|---|
| 3,227,162 | A | * | 1/1966 | Machuca Aguirre | 604/347 |
| 4,681,577 | A | * | 7/1987 | Stern et al. | 604/378 |
| 4,778,459 | A | * | 10/1988 | Fuisz | 604/378 |
| 4,781,713 | A | * | 11/1988 | Welch et al. | 604/385.19 |
| 4,950,262 | A | * | 8/1990 | Takagi | 604/385.101 |
| 5,425,726 | A | * | 6/1995 | Shimizu et al. | 604/385.23 |
| 5,716,350 | A | * | 2/1998 | Ryan | 604/385.09 |
| 5,891,124 | A | * | 4/1999 | Nomura et al. | 604/385.23 |

(Continued)

FOREIGN PATENT DOCUMENTS

| | | |
|---|---|---|
| JP | A-06-327715 | 11/1994 |
| JP | A-09-510384 | 10/1997 |

(Continued)

*Primary Examiner* — Lynne Anderson
*Assistant Examiner* — Peter S Vasat
(74) *Attorney, Agent, or Firm* — Oliff PLC

(57) ABSTRACT

It is an object of the present invention to provide an absorbent article having an excellent utilization efficiency of an absorber. The object is attained by an absorbent article including: a leak preventer including a bottom surface part extending in a front-rear direction, and side parts raised to an upper side at both left and right sides of the bottom surface part; an absorber containing super absorbent polymer for absorbing a body fluid placed in an internal space formed by the bottom surface part and the side parts of the leak preventer in at least one layer; and a liquid guide unit placed in a front body part of the internal space, at a position where a flow of discharged urine directly collides with the liquid guide unit, for moving, when urine is discharged, the urine from the position where the urine has collided therewith to other positions.

51 Claims, 36 Drawing Sheets

(56) References Cited

U.S. PATENT DOCUMENTS

| | | | |
|---|---|---|---|
| 5,897,544 A * | 4/1999 | Ronnberg | 604/385.19 |
| 5,947,947 A * | 9/1999 | Tanzer et al. | 604/385.101 |
| 5,961,505 A | 10/1999 | Coe et al. | |
| 6,152,908 A | 11/2000 | Widlund et al. | |
| 6,248,098 B1 | 6/2001 | Sayama | |
| 6,391,013 B1 | 5/2002 | Suzuki et al. | |
| 6,436,081 B1 | 8/2002 | Wada et al. | |
| 6,508,798 B1 | 1/2003 | Widlund et al. | |
| 6,814,721 B1 * | 11/2004 | Hansson | 604/385.01 |
| 6,926,703 B2 * | 8/2005 | Sugito et al. | 604/385.101 |
| 7,438,707 B2 * | 10/2008 | Bushman et al. | 604/385.22 |
| 2002/0013567 A1 | 1/2002 | Mishima et al. | |
| 2003/0093045 A1 * | 5/2003 | Erdman | 604/367 |
| 2004/0039361 A1 * | 2/2004 | LaVon et al. | 604/385.01 |
| 2004/0039363 A1 * | 2/2004 | Sugiyama et al. | 604/385.101 |
| 2004/0087927 A1 | 5/2004 | Suzuki | |
| 2004/0204697 A1 * | 10/2004 | Litvay | 604/367 |
| 2006/0058769 A1 * | 3/2006 | Suzuki et al. | 604/385.101 |

FOREIGN PATENT DOCUMENTS

| | | |
|---|---|---|
| JP | A-09-510385 | 10/1997 |
| JP | A-10-314217 | 12/1998 |
| JP | A-11-113958 | 4/1999 |
| JP | A-11-318976 | 11/1999 |
| JP | A-2000-271170 | 10/2000 |
| JP | A-2002-204811 | 7/2002 |
| JP | A-2006-116157 | 5/2006 |
| JP | A-2006-300317 | 11/2006 |
| WO | WO 02/065965 A1 | 8/2002 |

* cited by examiner

FIG. 1
(A)
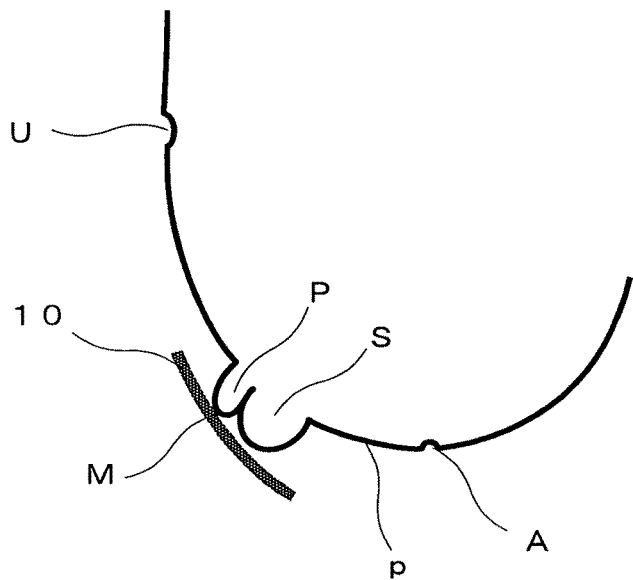
(B)
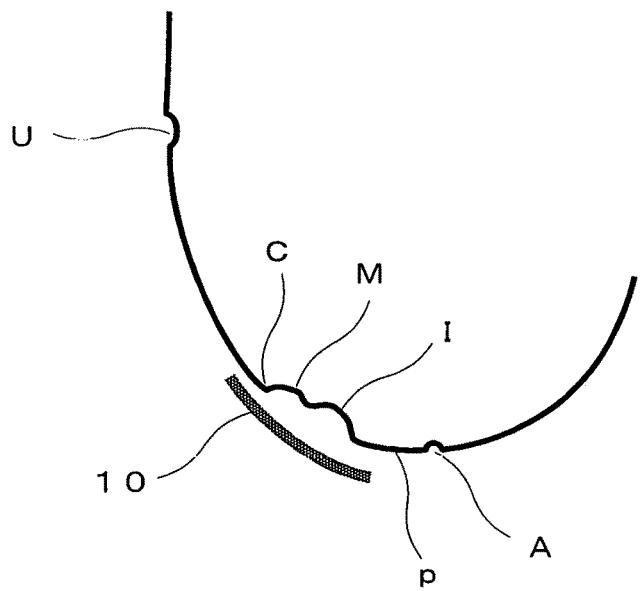

FIG. 2
(A)
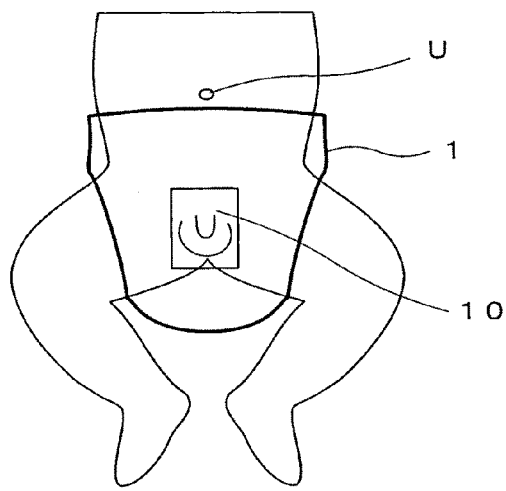
(B)
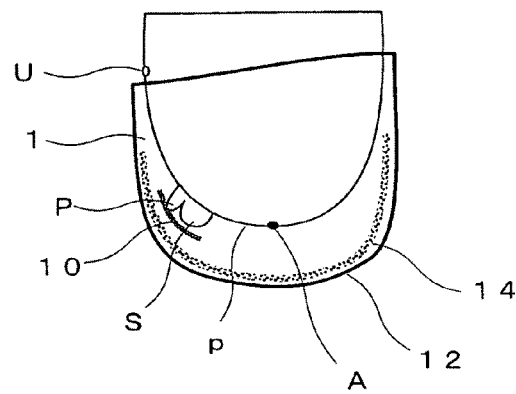
(C)
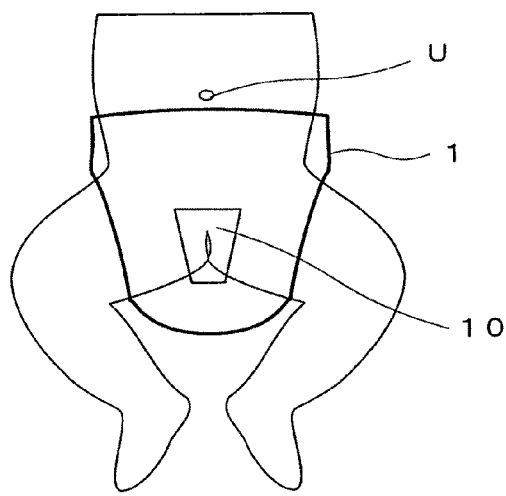
(D)
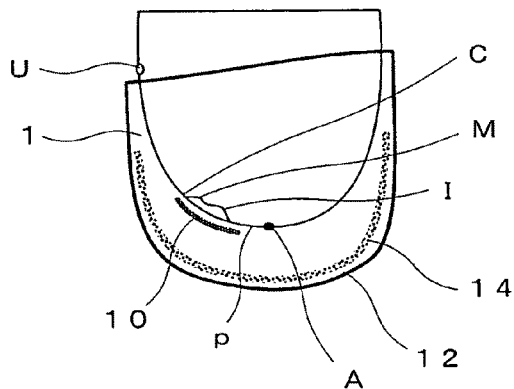

FIG. 3
(A)
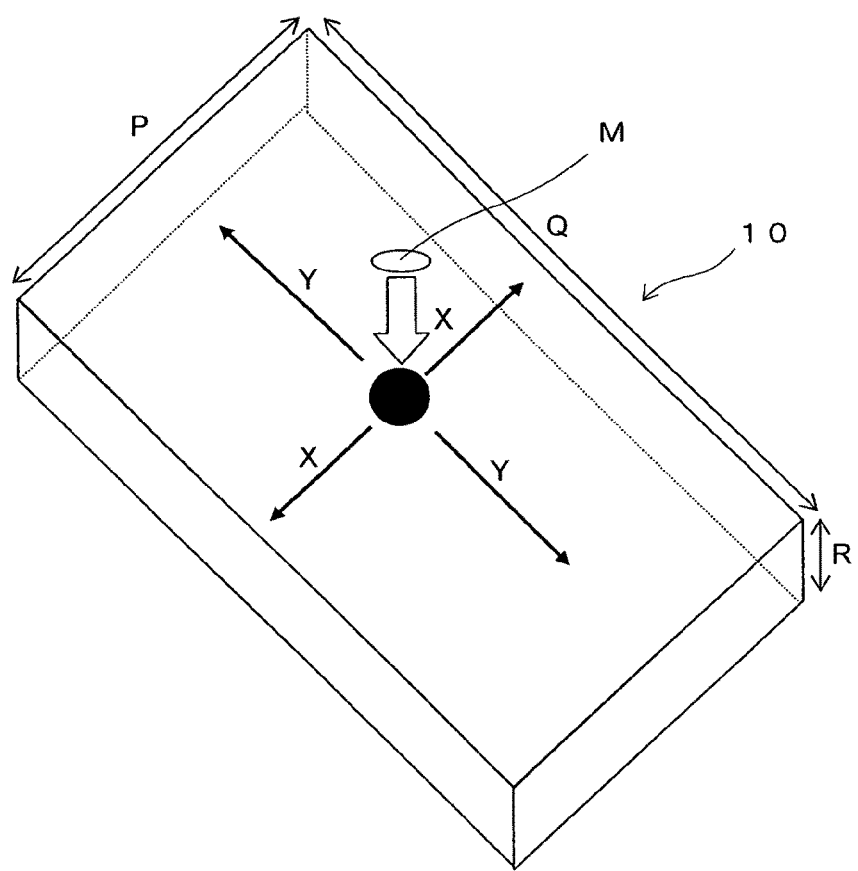
(B)
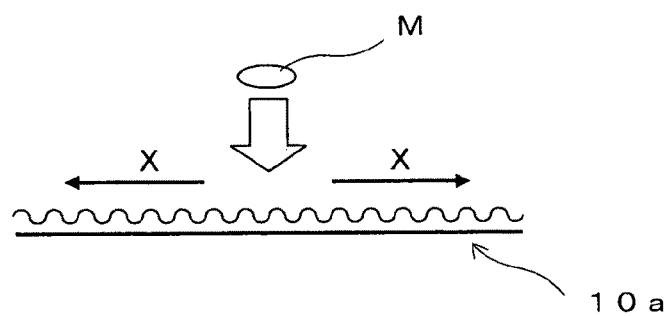
(C)
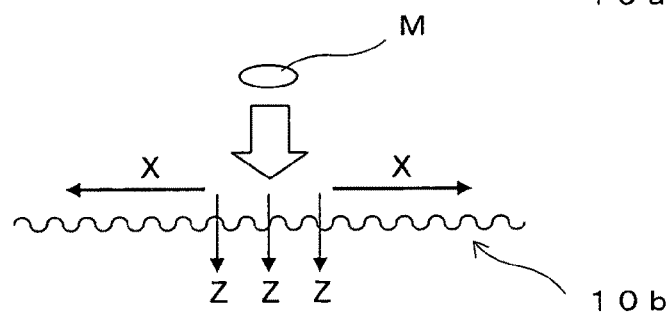

FIG. 4
(A)
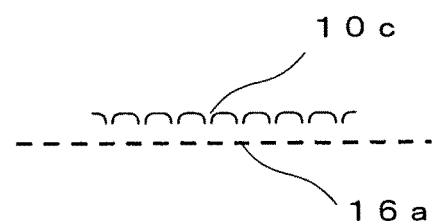
(B)
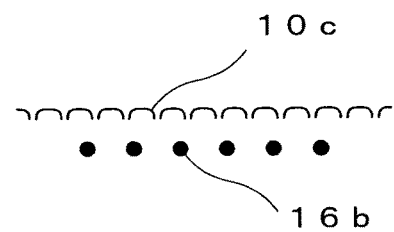
FIG. 5
(A)
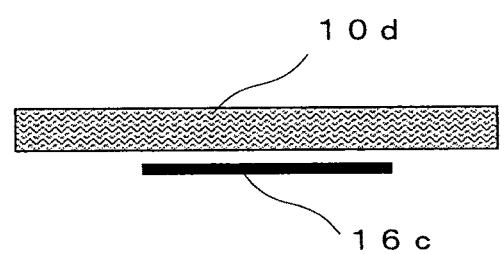
(B)
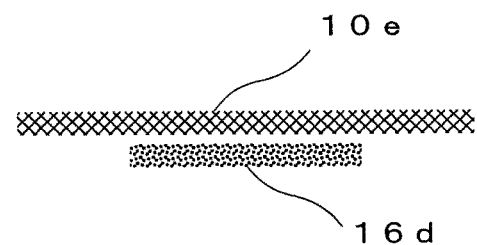
(C)
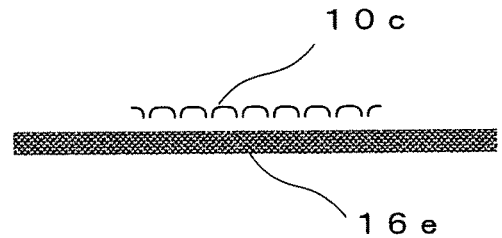

FIG. 6
(A)
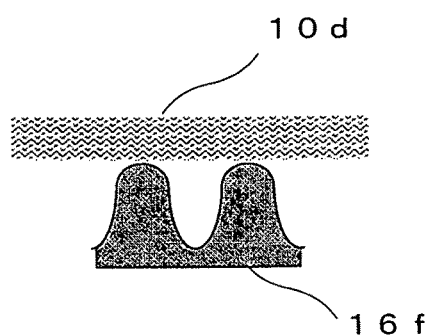
(B)
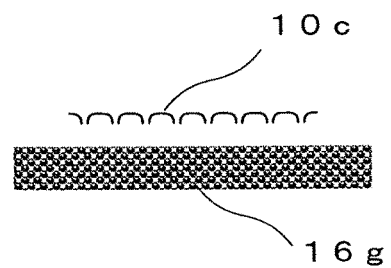

FIG. 19
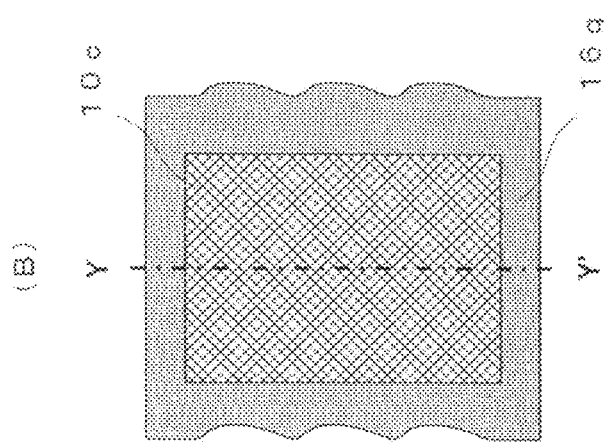
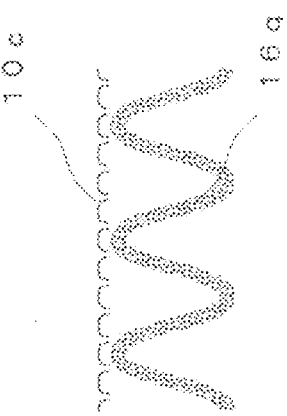
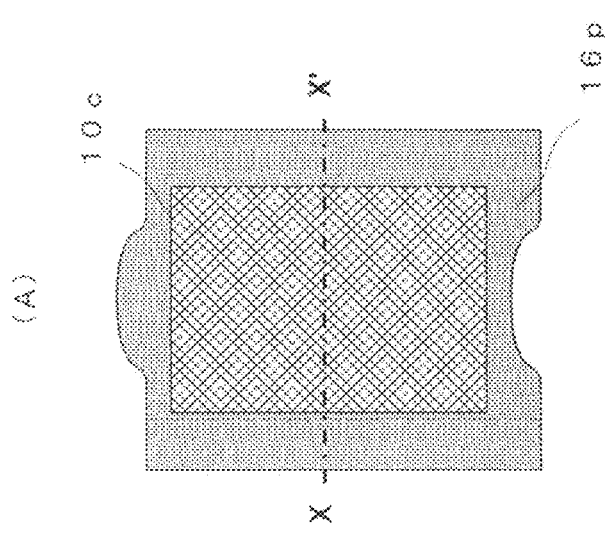
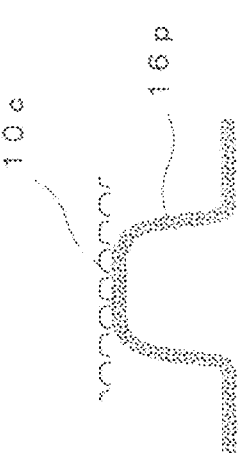
FIG. 18
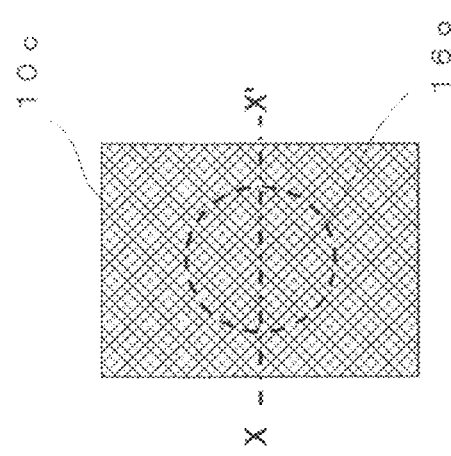
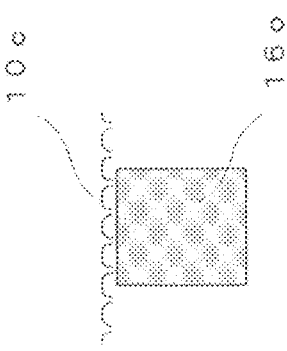

FIG. 22
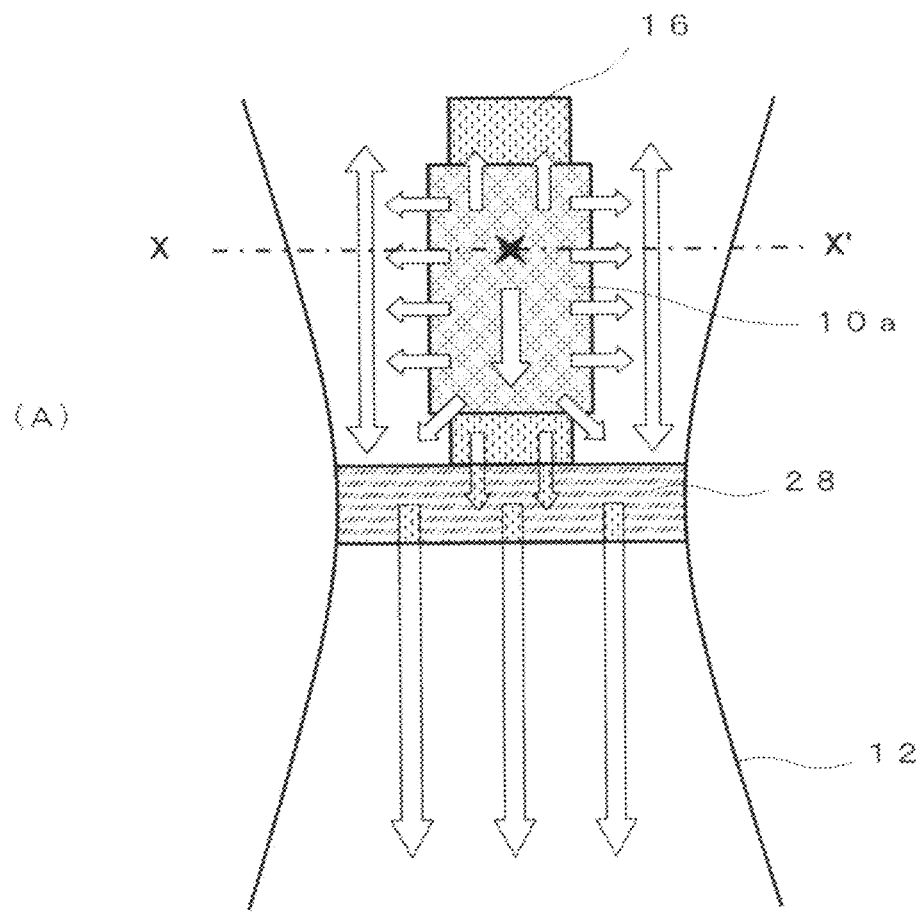
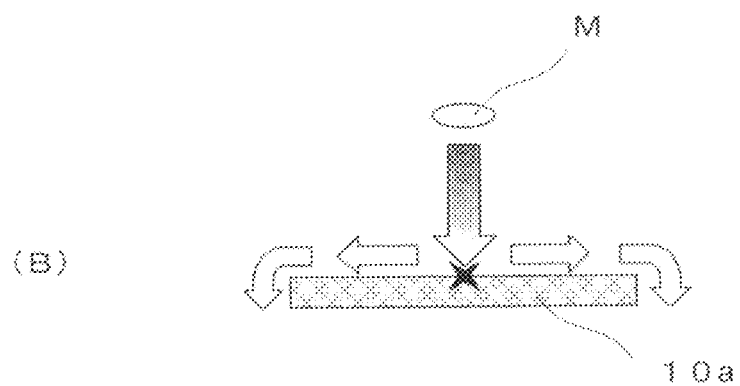

FIG. 23
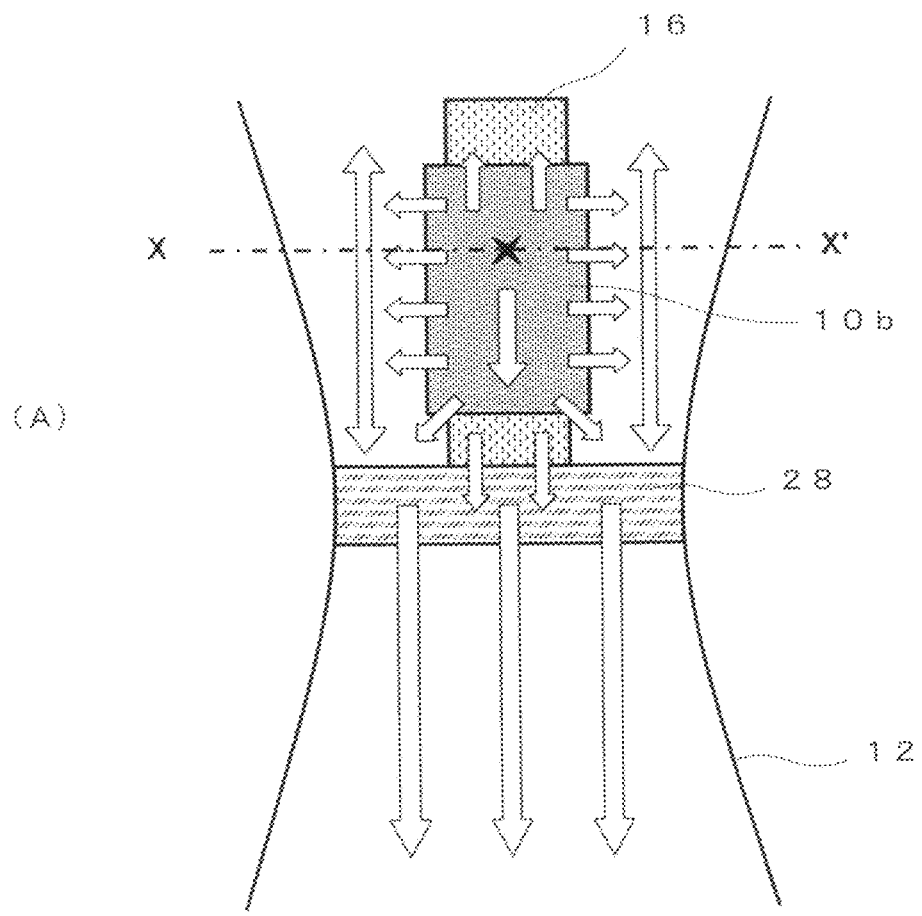
(A)
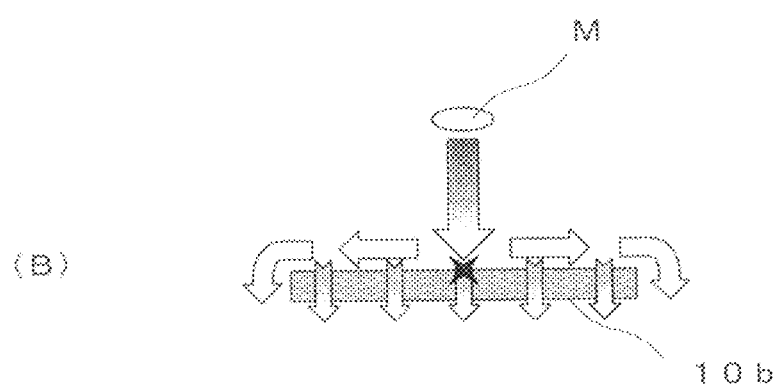
(B)

FIG. 25
(A)
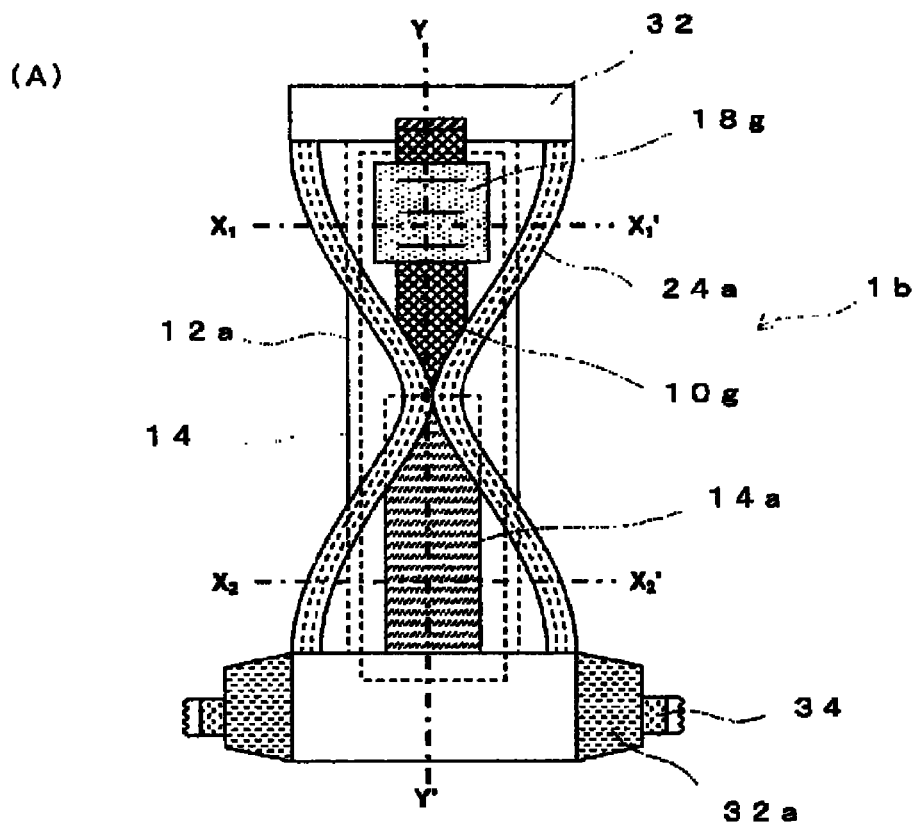
(B)
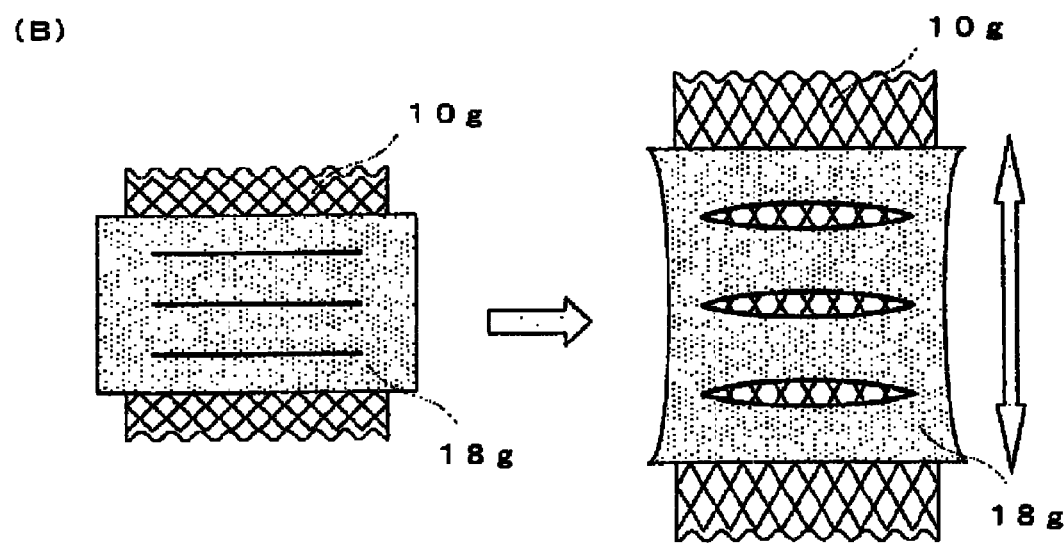

FIG. 38
(A)
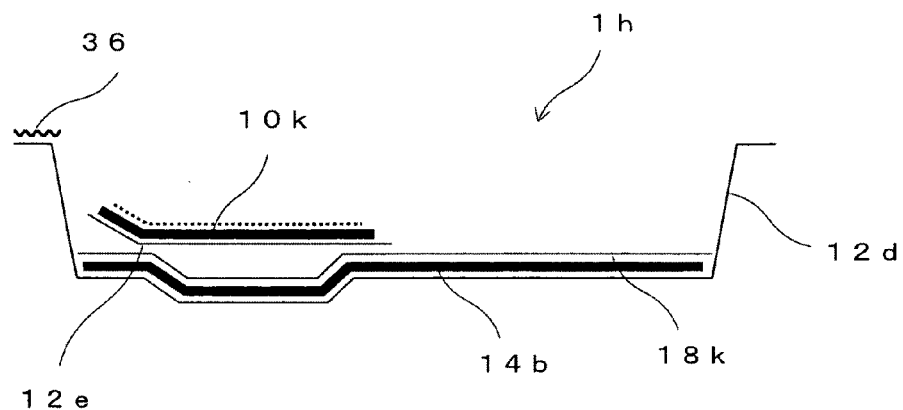
(B)
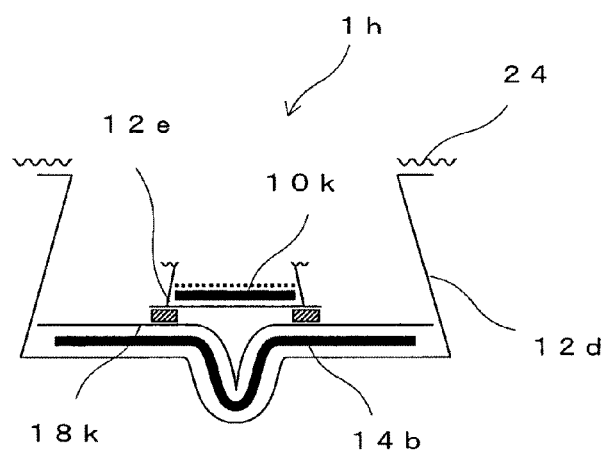
(C)
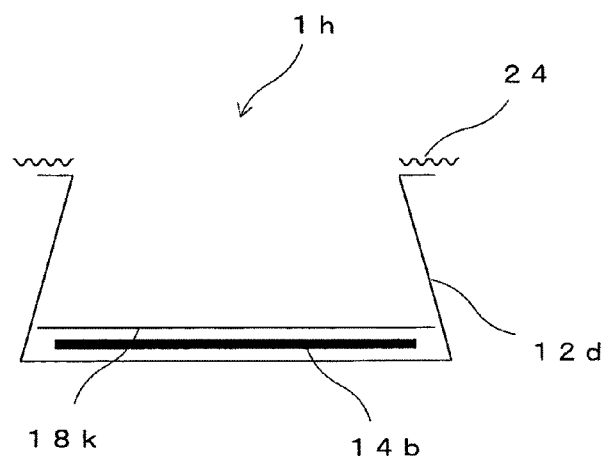

ABSORBENT ARTICLE

TECHNICAL FIELD

The present invention relates to an absorbent article, which is excellent in absorption efficiency and prevents a skin surface of a wearer from getting dirty by body excretion.

BACKGROUND ART

An absorbent article such as a disposable diaper is an article that absorbs urine discharged from the wearer with an absorber using an absorbing component such as wood pulp and super absorbent polymer (hereinafter also referred to as "SAP"), and receives feces (solid excretion).

The absorbent article desirably has sufficient urine absorbing ability so as to withstand long-time use and so as to prevent urine leakage. Therefore, a method of increasing the amount of absorber is normally adopted to provide the sufficient urine absorbing ability to the absorbent article.

However, the following problems still remain even if the amount of absorber is simply increased. First, the utilization efficiency of the absorber degrades. In other words, only a portion of the absorber close to the area where the urine is discharged absorbs urine, and another portion of the absorber distant from the area where the urine is discharged is not utilized to absorb urine, and thus the ratio of the portion utilized to absorb urine to the entire amount of absorber lowers. Next, there is a problem that, as the amount of absorbed urine increases, in particular, as the amount of absorbed urine approaches the design limit of the absorbing capacity, the amount of returning urine from the absorber to the top sheet, that is, the rewet amount increases. If the rewet amount is large, the moisture amount existent on the body surface of the wearer at and after discharge of urine increases, thereby degrading the wearing feeling as the body surface easily gets humid and becoming the main cause of so-called diaper rash.

In recent years, various absorbent articles, which are not only excellent in urine absorbing ability but also aiming to prevent problems such as stuffiness, rash, smell, and the like are proposed. The absorbent articles aiming to allow easy and hygienical disposal after use are also proposed.

For example, Patent Documents 1 to 4 describe so-called urine/feces separating diapers such as the absorbent article aiming to separately accommodate urine and feces by providing each opening for urine at a front part and for feces at a rear part of the front surface of the absorbent article, and the absorbent article aiming to prevent mixing of urine and feces by providing a partition member (urine/feces separating member) in the vicinity of a central part of the absorbent article.

However, if the front part is dedicated to urine and the rear part is dedicated to feces as in the absorbent articles described in Patent Documents 1 to 4, it is difficult to arrange the absorber in an amount that provides sufficient urine absorbing ability. In particular, the urine-absorbing ability is important as the number of urine discharges is actually greater than the number of feces discharges.

Patent Document 1 JP 6-327715 A
Patent Document 2: JP 9-510384 A
Patent Document 3: JP 9-510385 A
Patent Document 4: JP 11-113958 A

DISCLOSURE OF THE INVENTION

Problems to be Solved by the Invention

The inventors of the present invention proposed an absorbent article including a first leak preventer in sheet form; a second leak preventer in sheet form present above and in a rear part of the first leak preventer; and an absorbent containing a super absorbent polymer, capable of absorbing a body fluid, and provided above the first leak preventer extending from a front part of the first leak preventer beneath the second leak preventer in at least one layer (Japanese Patent Application No. 2006-55308). This absorbent article has a so-called "two-floor structure" in which the second leak preventer is placed on the first leak preventer at the rear part thereof, the first leak preventer absorbing urine and the second leak preventer receiving feces, whereby the separation process of urine and feces can be carried out while sufficiently maintaining the urine-absorbing ability.

However, the utilization efficiency of the absorbent needs to be high even in such absorbent article of "two-floor structure".

The inventors of the present invention further reviewed the above-mentioned problems, and found the following.

Specifically, it was found that the main reason the utilization efficiency degrades when the amount of absorber is increased is that the absorber is compressed and deforms at a narrowed portion under a crotch of the wearer, thus inhibiting the movement of urine, and the urine does not reach the portion at the rear body part of the absorber. In the conventional absorbent article, the ratio of the amount of its absorber actually used to absorb the urine to the entire amount of the absorber is an extremely low level of around 50 wt %.

Further, in the conventional absorbent article, the distance or the positional relationship between the meatus urinarius and the surface of the absorbent article where the discharged urine first contacts varies depending on the sex, body position, movement of the body, attached state when being worn, and the like (e.g., the meatus urinarius and the surface of the absorbent article may contact with or separate from each other, or the distance therebetween may become short or large. Further, the positional relationship may shift to the front, rear, right, or the left). Thus, the liquid movement state (movement path, etc.) from the meatus urinarius to the absorbent article is not always same. The occurrence of leakage cannot be prevented unless the width and the length are formed to be enough size, and sufficient design capacity is given for the absorber as a countermeasure in the conventional absorbent article. In recent years, the demands of the absorbent article are shifting more and more to the ultra-thin type as a great amount of super absorbent polymer is added, and therefore, it is becoming difficult to utilize adaptation to changes in the distance and the positional relationship between the meatus urinarius and the absorbent article based on the cushioning property specific to the conventional absorbent article using the absorber mainly made of bulky fluff pulp, whereby it has been more important to solve the problem that the utilization efficiency of the absorber degrades when the amount of absorber is increased.

Therefore, it is an object of the present invention to provide an absorbent article having an excellent utilization efficiency of an absorber.

Means for Solving the Problems

After careful study conducted with a view toward achieving the above-mentioned object, the inventors found that, by providing a liquid guide unit which is arranged at a position where the flow of discharged urine directly collides therewith, for moving the urine from the position where the urine has collided when urine is discharged to other positions, the urine can be moved from the discharged position using a force when the urine is discharged, and found that it is possible to obtain excellent utilization efficiency of the absorber, and completed the present invention.

According to the present invention, there are provided the following absorbent articles according to items (1) through (24).

(1) An absorbent article including:

a leak preventer including a bottom surface part extending in a front-rear direction, and side parts raised to an upper side at both left and right sides of the bottom surface part;

an absorber containing super absorbent polymer for absorbing a body fluid placed in an internal space formed by the bottom surface part and the side parts of the leak preventer in at least one layer; and a liquid guide unit placed in a front body part of the internal space, at a position where a flow of discharged urine directly collides with the liquid guide unit, for moving, when urine is discharged, the urine from the position where the urine has collided therewith to other positions.

(2) The absorbent article according to item (1), in which the liquid guide unit is in sheet-form.

(3) The absorbent article according to item (2), in which the liquid guide unit has a width of between 10 and 100 mm, length of between 20 and 200 mm, and thickness of between 0.1 and 2 mm.

(4) The absorbent article according to item (2) or (3), in which a part of a peripheral edge of the liquid guide unit is not connected to other portions of the absorbent article.

(5) The absorbent article according to any one of items (2) to (4), in which the liquid guide unit is formed of a film having openings.

(6) The absorbent article according to any one of items (2) to (4), in which at least a part of the liquid guide unit has cushioning property.

(7) The absorbent article according to item (6), in which the liquid guide unit is formed of bulky nonwoven fabric.

(8) The absorbent article according to any one of items (2) to (4), in which at least a part of the liquid guide unit has stretchability.

(9) The absorbent article according to item (8), in which the liquid guide unit is formed of a stretchable net.

(10) The absorbent article according to item (1), in which the liquid guide unit is formed of a molded foam body having a recessed surface on an upper side.

(11) The absorbent article according to any one of items (1) to (10), further including a top sheet on an upper side of the absorber.

(12) The absorbent article according to item (11), in which a rear end of the liquid guide unit and the top sheet are connected.

(13) The absorbent article according to any one of items (1) to (12), further including an urine/feces separating member in the vicinity of a central part in the front-rear direction of the leak preventer, the urine/feces separating member allowing a front body part of the internal space to function as an urine receiving part and a rear body part of the internal space to function as a feces receiving part.

(14) The absorbent article according to item (13), in which the urine/feces separating member and the liquid guide unit are connected.

(15) The absorbent article according to any one of items (1) to (14), further including side edge bands along ends of the side parts of the leak preventer.

(16) The absorbent article according to item (15), in which at least a part of the side edge bands has stretchability.

(17) The absorbent article according to item (15) or (16), in which the side edge bands and left and right ends of the liquid guide unit are connected directly or by a connection member.

(18) The absorbent article according to item (17), in which the connection member for connecting the side edge bands and the left and right ends of the liquid guide unit has stretchability.

(19) The absorbent article according to any one of items (1) to (18), including a support member for supporting the liquid guide unit from a lower side.

(20) The absorbent article according to item (19), in which the absorber is a sheet-form absorber, the sheet-form absorber functioning as the support member.

(21) The absorbent article according to item (19), in which at least a part of the support member has stretchability.

(22) The absorbent article according to any one of items (1) to (21), further including waist bands at a front end and a rear end of the leak preventer, the waist bands and the liquid guide unit being connected directly or by a connection member.

(23) The absorbent article according to item (22), in which the connection member for connecting the liquid guide unit and the waist bands has stretchability.

(24) The absorbent article according to any one of items (1) to (23), in which the absorber is a super absorbent sheet containing the super absorbent polymer at greater than or equal to 50 wt %.

Effects of the Invention

The absorbent article of the present invention excels in utilization efficiency of the absorber.

BRIEF DESCRIPTION OF THE DRAWINGS

FIG. 1 are schematic longitudinal end face views illustrating an example of an arrangement of a liquid guide unit.

FIG. 2 are schematic views of a state in which an absorbent article of the present invention is attached to a wearer.

FIG. 3 are schematic views illustrating an example of a structure and a function of the liquid guide unit.

FIG. 4 are schematic longitudinal end face views illustrating examples of various combinations of the liquid guide unit and a support member.

FIG. 5 are schematic longitudinal end face views illustrating examples of various combinations of the liquid guide unit and the support member.

FIG. 6 are schematic longitudinal end face views illustrating examples of various combinations of the liquid guide unit and the support member.

FIG. 18 are a schematic plan view illustrating a combination of the liquid guide unit formed of a film having openings and the support member, and a lateral end face view taken along the line X-X' of the plan view.

FIG. 19 are schematic views illustrating combinations of the liquid guide unit formed of a film having openings and the support member.

FIG. 22 are schematic views illustrating the state of movement of urine in one example of the absorbent article of the present invention.

FIG. 23 are schematic views illustrating the state of movement of urine in another example of the absorbent article of the present invention.

FIG. 25 are schematic views illustrating further another example of the absorbent article of the present invention.

FIG. 38 are schematic views illustrating further another example of the absorbent article of the present invention.

Figure 7:
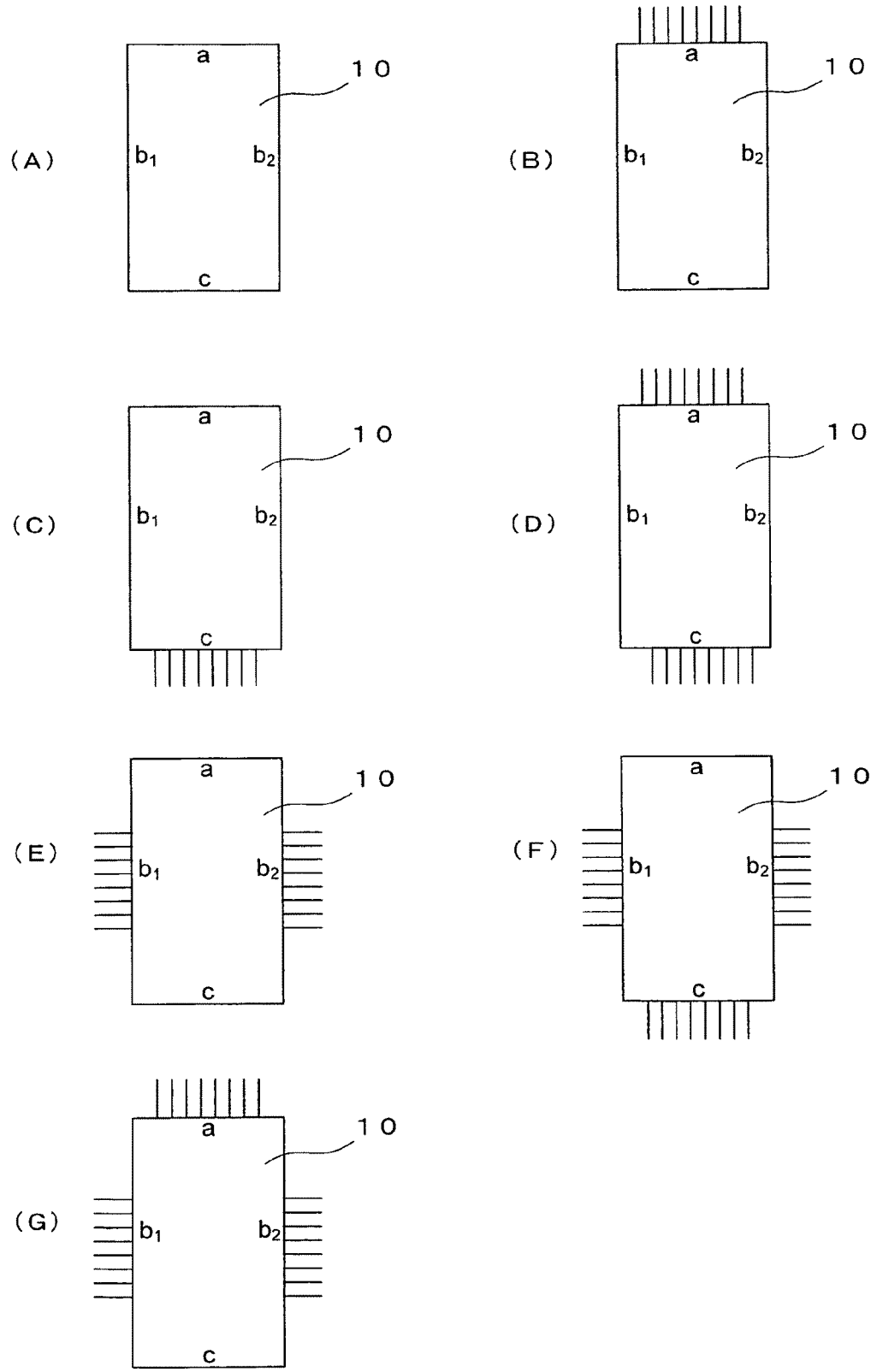
FIG. 7 are schematic plan views illustrating connected states and unconnected states of the peripheral edge of the liquid guide unit in sheet form and the other portions of the absorbent article.

DESCRIPTION OF SYMBOLS 1, 1*a*-1*h* absorbent article
10, 10*a*-10*k* liquid guide unit
12, 12*a*-12*e* leak preventer
14, 14*b* absorber
14*a* feces receiving absorber
16, 16*a*-16*s* support member
18, 18*a*-18*k* top sheets
20, 20*a* strechable member
24 side edge band
26, 26*a*, 26*b* connection member
28, 28*a*, 28*b* urine/feces separating member
30 feces barrier
32, 32*a*, 32*b* waist band
34, 34*a*, 34*b* connecting part
36 waist barrier sheet
38 feces receiving sheet
40 hydrophobic SMS nonwoven fabric
42 tissue paper
44 polyester web
46 SAP layer
A anus
C clitoris
I introitus
M meatus urinarius
P penis
p perineum
R feces receiving part
S scrotum
U umbilicus

BEST MODE FOR CARRYING OUT THE INVENTION

Hereinafter, an absorbent article of the present invention is described in more detail based on preferable embodiment modes illustrated in attached drawings. In the specification of the present invention, a side close to a skin of a wearer when the absorbent article is practically worn is referred to as "upper" side and a side far therefrom is referred to as "lower" side. In addition, a side corresponding to a front side of a body of a wearer when the absorbent article of the present invention is practically worn is referred to as "front" and a side corresponding to a rear side thereof is referred to as "rear". In the drawings, members which are practically in contact with each other may be illustrated to be separately positioned for easy understanding. Note that, in each plan view of the attached drawings, a front side of an absorbent article or the like is illustrated on an upper side of the view and in each longitudinal end face view of the attached drawings, a front side of an absorbent article or the like is illustrated on a left side of the view.

The absorbent article of the present invention basically includes: a leak preventer having a bottom surface part extending in the front-rear direction and side parts rising upward on both left and right sides of the bottom surface part; an absorber capable of absorbing body fluid, the absorber containing super absorbent polymer and placed in an internal space formed by the bottom surface part and the side parts of the leak preventer in at least one layer; and a liquid guide unit placed, in a front body part of the internal space, at a position where the flow of discharged urine directly collides therewith, and, when urine is discharged, moving the urine from the position where the urine has collided therewith to other positions.

Materials generally used for a back sheet may be used as materials for the leak preventer. Specific examples of the materials that can be used include: a resin film of PE, PP, PET, EVA, or the like; and a body fluid impermeable sheet such as a foamed sheet made of the above-mentioned resin. Further, a sheet having air permeability such as an air permeable film is preferably used as the body fluid impermeable sheet.

The resin film may be used as a multilayer sheet of the film and a nonwoven fabric for the better touch or appearance. In this case, an SB nonwoven fabric, a thermal bond nonwoven fabric (such as a spot bond type), or the like having a relatively light weight is preferably used as the nonwoven fabric.

Further, a multilayer sheet of the resin film and a sheet-form absorber described below may be used.

Further, a highly water-resistant nonwoven fabric may be used.
Examples of the highly water-resistant nonwoven fabric include an SMS having a water resistance of 100 mmH$_2$O or more and an SMS having water resistance by filling pores of a micro-fiber web with microfibrillated cellulose (MFC) or wax. In this case, the highly water-resistant nonwoven fabric may be used alone, or used as a multilayer sheet of a film and the highly water-resistant nonwoven fabric.

The leak preventer may be formed of a plurality of members.

As described above, the leak preventer includes the bottom surface part extending in the front-rear direction and the side parts rising upward on both left and right sides of the bottom surface part. The side parts are preferably symmetrical.

The internal space is formed by the bottom surface part and the side parts of the leak preventer.

The absorber is arranged in the internal space.

There are no particular limitations regarding the absorber used in the present invention as long as it contains super absorbent polymer and is capable of absorbing body fluid. For example, it is possible to use a powder absorber such as powder wood pulp and unprocessed SAP. However, taking into consideration stability in form, risk of detachment, etc., a sheet-form absorber is preferable. Above all, it is desirable to adopt a sheet-form absorber formed by coating nonwoven fabric with super absorbent polymer as mentioned above.

The kind of absorber can be selected as appropriate according to the use. For example, when the absorbent article of the present invention is used as a diaper for children, an absorber containing a large amount of wood pulp is preferable for newborn babies and a few-month-old babies (small-size), and an absorber containing large amount of SAP is preferable for several-month-old babies or older babies (medium-size, large-size, or extra large size).

In a preferred mode, the sheet-form absorber is a super absorbent sheet containing 50 wt % or more of SAP, preferably 60 to 95 wt % of SAP.

The super absorbent sheet is an ultrathin sheet-form absorber containing SAP as a main component. The super absorbent sheet has a very high SAP content, and thus is very thin. The super absorbent sheet has a thickness of preferably 1.5 mm or less, more preferably 1 mm or less.

A structure or a production process for the super absorbent sheet is not particularly limited as long as the super absorbent sheet is an ultrathin sheet-form absorber containing SAP as a main component.

An example of the super absorbent sheet includes a super absorbent sheet obtained by an Air Laid process. The Air Laid process involves mixing pulverized wood pulp and SAP, adding a binder, and forming the mixture into a sheet, to thereby obtain a super absorbent sheet. Examples of the super absorbent sheet obtained by this process include: NOVATHIN (US registered trademark) manufactured by Rayonier Inc.; and B-SAP manufactured by Oji Kinocloth Co., Ltd.

Another example of the super absorbent sheet includes a super absorbent sheet obtained by a process involving coating SAP-dispersed slurry on a body fluid permeable sheet such as a nonwoven fabric. The SAP-dispersed slurry is preferably prepared by dispersing SAP and microfibrillated cellulose (MFC) in a mixed solvent of water and ethanol. An example of the super absorbent sheet obtained by this process includes MegaThin (registered trademark) manufactured by Japan Absorbent Technology Institute.

Other examples of the super absorbent sheet include: a super absorbent sheet obtained by a process involving carrying a large amount of SAP on a raised nonwoven fabric and fixing the SAP with a hot melt binder, an emulsion binder, a water-soluble fiber, or the like; a super absorbent sheet obtained through a process involving mixing fibrous SAP with a polyethylene terephthalate (PET) fiber and forming the mixture into a web; and an SAP sheet obtained by providing tissues above and below an SAP layer.

The absorber is provided in at least one layer. That is, the absorber may be provided as one layer, or as two or more layers (multilayer).

Further, the absorber may be provided while being folded.

The liquid guide unit is arranged at the front body part in the internal space. The liquid guide unit is placed at a position where the flow of discharged urine directly collides therewith, and, when urine is discharged, the urine moves from the position where the urine has collided to other positions.

FIG. 1 are schematic longitudinal end face views illustrating an example of arrangement of the liquid guide unit. In FIG. 1, the left side corresponds to the front side of the absorbent article. In FIG. 1, the portions other than the liquid guide unit of the absorbent article are omitted.

FIG. 1(A) illustrates a case of when the wearer is a boy and FIG. 1(B) illustrates a case of when the wearer is a girl. The positional relationship of umbilicus U, penis P, scrotum S, clitoris C, meatus urinarius M, introitus I, perineum p, and anus A is as illustrated in FIG. 1(A) and FIG. 1(B).

As illustrated in FIG. 1(A) and FIG. 1(B), the liquid guide unit 10 is arranged near the meatus urinarius M, and the flow of discharged urine directly collides thereto. The liquid guide unit 10 spreads from the vicinity of the meatus urinarius M to the periphery, and hence when urine is discharged, the urine moves from the position where the urine has collided to other positions. Therefore, the absorbent article using the liquid guide unit 10 illustrated in FIG. 1 has an absorber which is excellent in utilization efficiency.

The distance between the surface of the liquid guide unit and the meatus urinarius is preferably between 0 and 20 mm, and more preferably between 0 and 5 mm. When the distance between the surface of the liquid guide unit and meatus urinarius is 0 mm, this means a state in which the surface of the liquid guide unit is in contact with the meatus urinarius, and includes a state of being in contact therewith by application of pressure.

The liquid guide unit is a site where the discharged urine first comes into contact, and the position where the urine collides with the liquid guide unit is constant and the function of the liquid guide unit can be easily exhibited if the distance between the surface of the liquid guide unit and the meatus urinarius is in the above-mentioned range. Since the urine is discharged with force, the discharging direction and the position barely change if the surface of the liquid guide unit and the meatus urinarius are close to each other, and thus the urine can be stably received and the urine can be uniformly distributed. Further, if the surface of the liquid guide unit and the meatus urinarius are close to each other, the position where the urine collides with the liquid guide unit is less likely to shift even if the body of the wearer moves.

In the case of male adults, the displacement and deformation of the penis while wearing are large, and thus the surface of the liquid guide unit is preferably brought into contact with the upper surface of the penis from the tip to the root of the penis so that the tip of the penis faces downward.

FIG. 2 are schematic views of a state in which the absorbent article of the present invention is attached to the wearer. FIG. 2(A) and FIG. 2(B) are respectively a front view and longitudinal end face view of the case when the wearer is a boy, and FIG. 2(C) and FIG. 2(D) are respectively a front view and longitudinal end face view of the case when the wearer is a girl. The positional relationship of the umbilicus U, penis P, scrotum S, clitoris C, meatus urinarius M, introitus I, perineum p, and anus A of the wearer are as illustrated in FIG. 2(A) to FIG. 2(D).

The absorbent article 1 illustrated in FIG. 2 includes a leak preventer 12, an absorber 14, and a liquid guide unit 10.

As illustrated in FIG. 2(B) and FIG. 2(D), the liquid guide unit 10 is preferably arranged spaced apart from the absorber 14 (non-contact state). The flow of discharged urine can be supplied to the target site of the absorber in a controlled state by the liquid guide unit by maintaining the liquid guide unit at a position independent from other components.

FIG. 3 are schematic views illustrating an example of the structure and the function of the liquid guide unit. FIG. 3(A) is a perspective view, and FIG. 3(B) and FIG. 3(C) are respectively longitudinal end face views.

The liquid guide unit 10 illustrated in FIG. 3(A) has a sheet-form (band form), whose width in the left and right direction (X direction) is P, length in the front-rear direction (Y direction) is Q, and thickness in the vertical direction (Z direction) is R.

In FIG. 3, the urine discharged from the meatus urinarius directly collides to the upper surface of the liquid guide unit, and then moves on the plane defined by the X direction and the Y direction if the liquid guide unit is a liquid guide unit 10a of liquid impermeable type (see FIG. 3(B)), and moves through a three-dimensionally defined by the X direction, the Y direction, and the Z direction if the liquid guide unit is a liquid guide unit 10b of liquid permeable type (see FIG. 3(C)).

The conventional absorbent article has a structure in which such a liquid guide unit is not provided, and a liquid permeable surface sheet is placed on the absorber. In this case, the discharged urine first permeates through the surface sheet mainly in the Z direction, moves through the interior of the absorber, and diffuses in the X direction and the Y direction. Therefore, the movement range of the urine is narrow.

The structure, the material, and the like of the liquid guide unit are not particularly limited as long as it can exhibit the above-mentioned function.

A liquid guide unit in sheet form is a liquid guide unit of a preferred structure. The liquid guide unit in sheet form preferably has a width P of between 10 and 100 mm, the length Q of between 20 and 200 mm, and the thickness R of between 0.1 and 2 mm.

The material of the liquid guide unit in sheet form is not particularly limited, and may be formed of film, net, nonwoven fabric, fabric, knitted fabric, or a combination thereof.

The liquid guide unit may have stretchability at least partially, or may be combined with a stretchable material. In such case, the liquid guide unit exerts delicate follow-up property according to change in body position and movement of the body of the wearer, and hence the position of the liquid guide unit can be always easily maintained constant.

The liquid guide unit may have cushioning property at least partially, or may be combined with a material having cushioning property. In such case, the thickness of the liquid guide unit itself or the combination of the liquid guide unit and the material having cushioning property can be easily changed, whereby the liquid guide unit exerts delicate follow-up property according to change in body position and movement of the body of the wearer, and hence the position of the liquid guide unit can be always easily maintained constant.

A specific structure of the liquid guide unit in sheet form, for example, suitably includes a film having openings, bulky nonwoven fabric, and stretchable net.

The film having openings is a film having numerous openings. The film having openings has liquid permeability since the liquid passes through the openings, and has a fluid-distributing function since the liquid moves on the portion other than the openings.

The film having openings includes a polyolefin-based film including relatively large openings having a diameter of greater than or equal to 0.5 mm and introductory tubes, as proposed by the inventors of the present invention in WO 02/065965. The polyolefin-based film preferably has a thickness of greater than or equal to 1 mm. The polyolefin-based film is preferably subjected to surface hydrophilic processing with a surfactant and the like to provide excellent urine adaptation and wettability.

The bulky nonwoven fabric is a nonwoven fabric having an apparent specific gravity of smaller than or equal to $0.2 \text{ g/cm}^3$. The bulky nonwoven fabric can be obtained through a dry method such as air-through method and spot-bond method.

The bulky nonwoven fabric has high porosity and also has liquid permeability, and may function as an acquisition layer exhibiting a temporary urine holding function.

The bulky nonwoven fabric may be used as a sub-layer by being in contact with the top sheet.

In the present invention, more bulky nonwoven fabric having higher porosity is preferable. For instance, the nonwoven fabric is made of synthetic fiber such as PE fiber, PP fiber, PET fiber, PE/PET bicomponent fiber, and PET/PET bicomponent fiber, the synthetic fiber having a hollow structure and a fineness of preferably greater than or equal to 3 d and more preferably greater than or equal to 5 d, where an apparent specific gravity is between 0.01 and 0.1 $\text{g/cm}^3$ and thickness under no-load is between 1 and 5 mm.

The stretchable net is a meshed article having stretchability in at least one direction.

The stretchability may originate from the stretchability of the material itself of the meshed article, may be provided by the structure of the meshed article (e.g., meshed article in which nylon filament is knitted in stockinet), or may be a combination of both.

The stretchable net suitably includes a net made of stretchable polyurethane filament, combination-weaved net of nylon and polyurethane filament, stretchable net used in pantyhose for women, or an unidirectional stretchable net (e.g., manufactured by US Conwed Plastics) in which a rubber thread including the PE monofilament (e.g., 30 d) for the vertical series and the SEBS elastomer (e.g., 50 d) for the horizontal series are combination-weaved.

One preferred mode of the liquid guide unit is to be used in combination with a support member. Specifically, the liquid guide unit is preferably supported by the support member from the lower side.

The support member has a function of enhancing the shape stability of the liquid guide unit, a function of holding the liquid guide unit at a position proximate to the meatus urinarius, a function of blocking a part of the lower surface of the liquid guide unit which is liquid permeable so as to be liquid impermeable, a function of ensuring a space between the liquid guide unit and the absorber, and the like.

The material used for the support member includes fiber material of thread-form or rope-form, plastic material of film-form or mat-form, and foam made of polyethylene, propylene, urethane or the like having cushioning property. Using the sheet-form absorber for the support member as one means for enhancing the absorbing ability is one mode of the present invention.

Providing stretchability to at least a part of the support member is also one preferred mode. In this case, the support member has a function of pressing the liquid guide unit against the vicinity of the meatus urinarius of the wearer.

Examples of the support member having stretchability in at least a part include stretchable net, rubber threads arranged in parallel, stretchable urethane film, and stretchable urethane foam sheet.

FIG. 4 to FIG. 6 are schematic longitudinal end face views illustrating examples of various combinations of the liquid guide unit and the support member.

In the combination of the liquid guide unit and the support member illustrated in FIG. 4(A), a liquid guide unit $10c$ is a liquid permeable film having openings, and a support member $16a$ is a liquid permeable stretchable net.

In the combination of the liquid guide unit and the support member illustrated in FIG. 4(B), the liquid guide unit $10c$ is a liquid permeable film having openings, and a support member $16b$ comprises rubber threads arranged in parallel in the left and right direction.

In all combinations of the liquid guide unit and the support member illustrated in FIG. 4, the support member has the function of pressing the liquid guide unit against the vicinity of the meatus urinarius of the wearer. The combinations of the liquid guide unit and the support member illustrated in FIG. 4 all have liquid permeability.

In the combination of the liquid guide unit and the support member illustrated in FIG. 5(A), a liquid guide unit $10d$ is a liquid permeable bulky nonwoven fabric, and a support member $16c$ is a liquid impermeable stretchable urethane film.

In the combination of the liquid guide unit and the support member illustrated in FIG. 5(B), a liquid guide unit $10e$ is a liquid permeable stretchable net, and a sheet-form absorber used for the absorber functions as a support member $16d$.

In the combination of the liquid guide unit and the support member illustrated in FIG. 5(C), the liquid guide unit $10c$ is a liquid permeable film having openings, and a support member $16e$ is a liquid impermeable stretchable urethane foam sheet.

In all combinations of the liquid guide unit and the support member illustrated in FIG. 5, the support member contributes to maintaining the shape of the liquid guide unit, and partially or entirely blocks the lower surface of the liquid guide unit so that such the blocked portion becomes liquid impermeable.

In the combination of the liquid guide unit and the support member illustrated in FIG. 6(A), the liquid guide unit $10d$ is a bulky nonwoven fabric, and a support member $16f$ is a molded projecting block (e.g., thickness of 15 mm) of urethane foam having cushioning property.

In the combination of the liquid guide unit and the support member illustrated in FIG. 6(B), the liquid guide unit $10c$ is a film having openings, and a support member $16g$ is a net-form foam (e.g., thickness of 10 mm).

In all combinations of the liquid guide unit and the support member illustrated in FIG. 6, the support member has a function of approaching the liquid guide unit to the vicinity of the meatus urinarius of the wearer, and has a function of ensuring a space between the absorber beneath the support member and the liquid guide unit.

Figure 16:
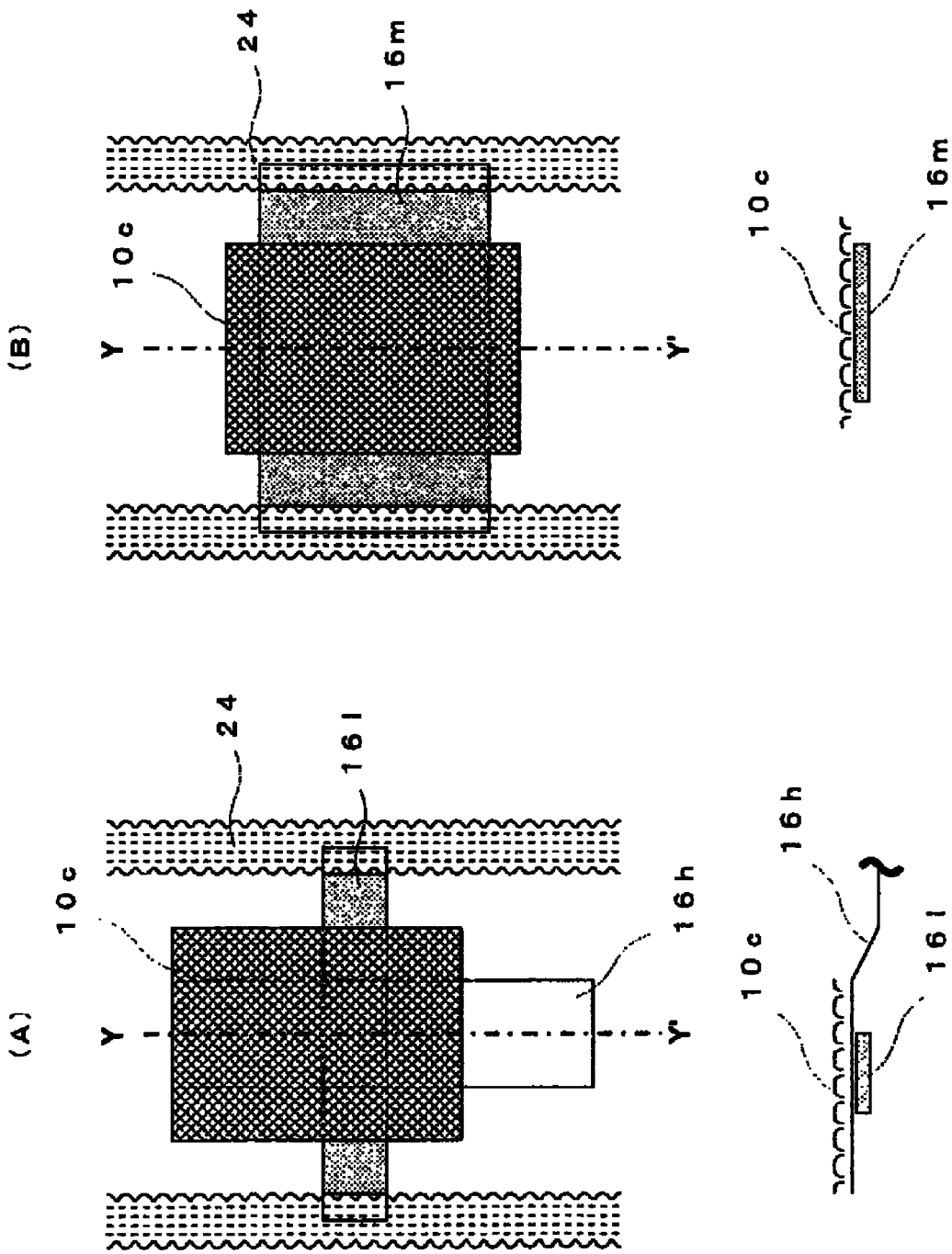
FIG. 16 are schematic plan views illustrating combinations of the liquid guide unit formed of a film having openings, the side edge bands, and the support member, and longitudinal end face views taken along the line Y-Y' of the plan views.
Figure 17:
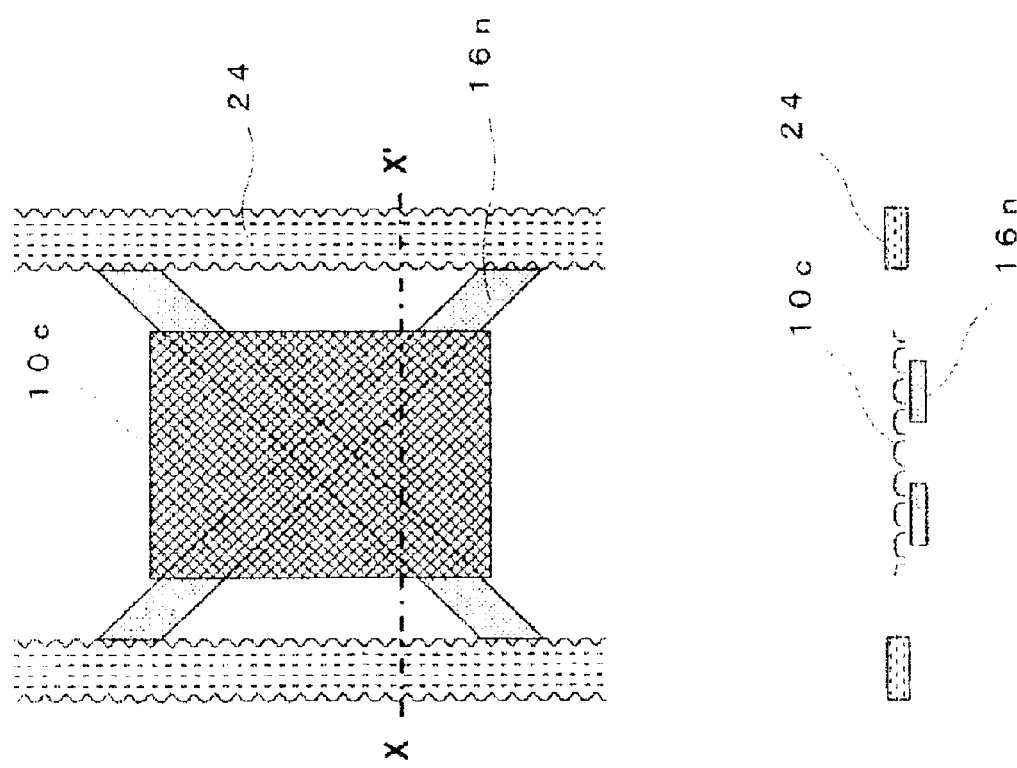
FIG. 17 are a schematic plan view illustrating a combination of the liquid guide unit formed of a film having openings, the side edge bands, and the support member, and a lateral end face view taken along the line X-X' of the plan view.

One preferred mode of the support member is to be connected to the side edge bands on both left and right sides so as to bridge between the side edge bands (see FIG. 16 and FIG. 17).

As described above, the liquid guide unit is arranged at the front body part in the internal space formed by the bottom surface part and the side parts of the leak preventer, but is normally connected to other portions of the absorbent article (e.g., top sheet, waist band, urine/feces separating member, side edge bands provided along the ends of the side parts of the leak preventer).

If the liquid guide unit is in sheet form, a part of the peripheral edge of the liquid guide unit is preferably not connected to other portions of the absorbent article in order for the liquid guide unit to maintain a constant positional relationship with the meatus urinarius.

When being worn, the entire shape of the absorbent article of the present invention constantly changes by the movement and the body position of the wearer. In particular, such tendency is likely when the absorbent article of the present invention is used as a diaper for children. If a part of the peripheral edge of the liquid guide unit is not connected to other portions of the absorbent article, the association of the change in shape of the absorbent article with the shape and thus with the change in positional relationship with the meatus urinarius of the liquid guide unit can be lowered (that is, degree of freedom of the liquid guide unit increases), and as a result, the influence of the movement of the wearer can be effectively eliminated.

FIG. 7 are schematic plan views illustrating connected states and unconnected states of the peripheral edge of the liquid guide unit in sheet form and the other portions of the absorbent article. In FIG. 7, the connection part of the peripheral edge of the liquid guide unit and the other portions of the absorbent article is illustrated with plural parallel lines. Further, in FIG. 7, the portion others than the liquid guide unit of the absorbent article are omitted.

In the liquid guide unit 10 illustrated in FIG. 7(A), none of the front end a, the left and right ends $b_1$, $b_2$ and the rear end c is connected to the other portions of the absorbent article. In this mode, the liquid guide unit can be fixed by being connected to other portions of the absorbent article at a central part on the rear side of the liquid guide unit in sheet form (this is the same in each mode illustrated in FIG. 7(B) to FIG. 7(G)).

In the liquid guide unit 10 illustrated in FIG. 7(B), the front end a is connected to another portion of the absorbent article, and the left and right ends $b_1$, $b_2$ and the rear end c are not connected to the other portions of the absorbent article.

In the liquid guide unit 10 illustrated in FIG. 7(C), the rear end c is connected to another portion of the absorbent article, and the front end a and the left and right ends $b_1$, $b_2$ are not connected to the other portions of the absorbent article.

In the liquid guide unit 10 illustrated in FIG. 7(D), the front end a and the rear end c connected to other portions of the absorbent article, and the left and right ends $b_1$, $b_2$ are not connected to the other portions of the absorbent article.

In the liquid guide unit 10 illustrated in FIG. 7(E), the left and right ends $b_1$, $b_2$ are connected to other portions of the absorbent article, and the front end a and the rear end c are not connected to other portions of the absorbent article.

In the liquid guide unit 10 illustrated in FIG. 7(F), the left and right ends $b_1$, $b_2$ and the rear end c are connected to other portions of the absorbent article, and the front end a is not connected to other portions of the absorbent article.

In the liquid guide unit 10 illustrated in FIG. 7(G), the front end a and the left and right ends $b_1$, $b_2$ are connected to another portion of the absorbent article, and the rear end c is not connected to the other portions of the absorbent article.

One preferred mode of the absorbent article of the present invention is to further include the urine/feces separating member in the vicinity of the central part in the front-rear direction of the leak preventer, and to have the front body part in the internal space functioning as a urine receiving part and the rear body part in the internal space functioning as a feces receiving part by the urine/feces separating member. The urine/feces separating member is not particularly limited as long as it partitions the internal space to the front and the rear, and physically prevents the movement of the urine and the feces. For instance, an adhesive, rubber, film, foam, non-woven fabric, and a net-form sheet may be used.

In this case, one preferred mode of the present invention is to have the liquid guide unit connected to the urine/feces separating member.

The rear end of the liquid guide unit is preferably connected directly or through an intermediation of the support member to the surface of the absorber (or top sheet contacting the absorber) beneath the urine/feces separating member (see FIG. 32(A)) or at a position behind the urine/feces separating member (see FIG. 28(A)). In this mode, the urine that moved to the rear side from the position where colliding with the liquid guide unit easily moves to the absorber positioned at the further rear body part.

One preferred mode of the present invention is to have the liquid guide unit connected to the side edge bands.

The side edge bands are members provided respectively along the ends of the side parts of the leak preventer, and have a function of maintaining a state closely contacting to the body surface of the wearer. Examples of the side edge bands include one having the plural synthetic rubbers, urethane filaments, and the like arranged in parallel, or one having an elastic film of a width of between 2 and 20 mm sandwiched in the two sheets of nonwoven fabric.

Among them, the side edge bands, which are connected directly or by connection members to the left and right ends of the liquid guide unit are preferable (see FIG. 13 to FIG. 17, FIG. 20, and FIG. 21).

Figure 20:
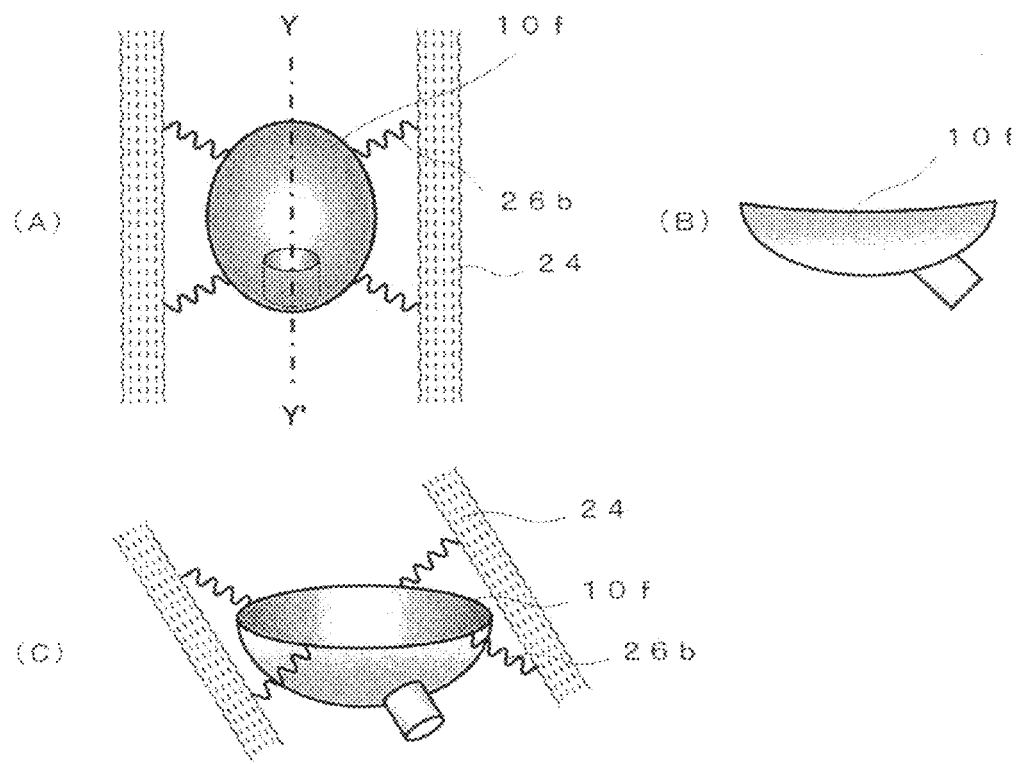
FIG. 20 are schematic views illustrating combinations of the liquid guide unit formed of a molded foam body and the side edge bands.

In this case, one preferred mode is to provide stretchability to the connection members (see FIG. 13(B) and FIG. 20).

Thus, further stretchability can be given in a suspended structure like a hammock, whereby the position of the liquid guide unit can be further maintained constant even if the body position or the movement of the wearer changes.

One preferred mode of the side edge band are to provide stretchability to at least part of the side edge bands. In this mode, a gap is less likely to be formed between the side edge bands and the body surface of the wearer, and thus the close contact therebetween can be more easily maintained.

One preferred mode of the present invention is to have the liquid guide unit connected to the waist band.

The waist band forms a waist hole for receiving the waist of the wearer when being worn. The waist band is provided at the front end and/or the rear end of the leak preventer. If the waist band is provided at the front end or the rear end of the leak preventer, either one of a hook member or a loop member is provided at the left and right ends of the waist band, and the other one of the hook member or the loop member is provided at the rear part or the front part of the leak preventer. The waist hole is formed by connecting the hook member and the loop member. If the waist bands are provided at the front end and the rear end of the leak preventer, the hook members are provided at the left or right ends of one of the waist bands, and the loop members are provided at the left and right ends of the other waist band. The waist hole is formed by connecting the hook members and the loop members.

The waist band has a structure in which 15 urethane filaments (e.g., 470dtex manufactured by DU-PONT TORAY CO., LTD.) are sandwiched between two SMSs (e.g., manufactured by AVGOL Ltd., weight 13 g/m$^2$).

Among them, it is preferable that the waist bands are provided at the front end and the rear end of the leak preventer, and the waist bands and the liquid guide unit are connected directly or by a connection member (see FIG. 8(A), FIG. 9, FIG. 10(B), FIG. 11, and FIG. 12(B)). Thus, the liquid guide unit is suspended at the front end and the rear end to be in a suspended structure like to a hammock, and the proximate state of the liquid guide unit and the meatus urinarius is stably maintained.

Figure 11:
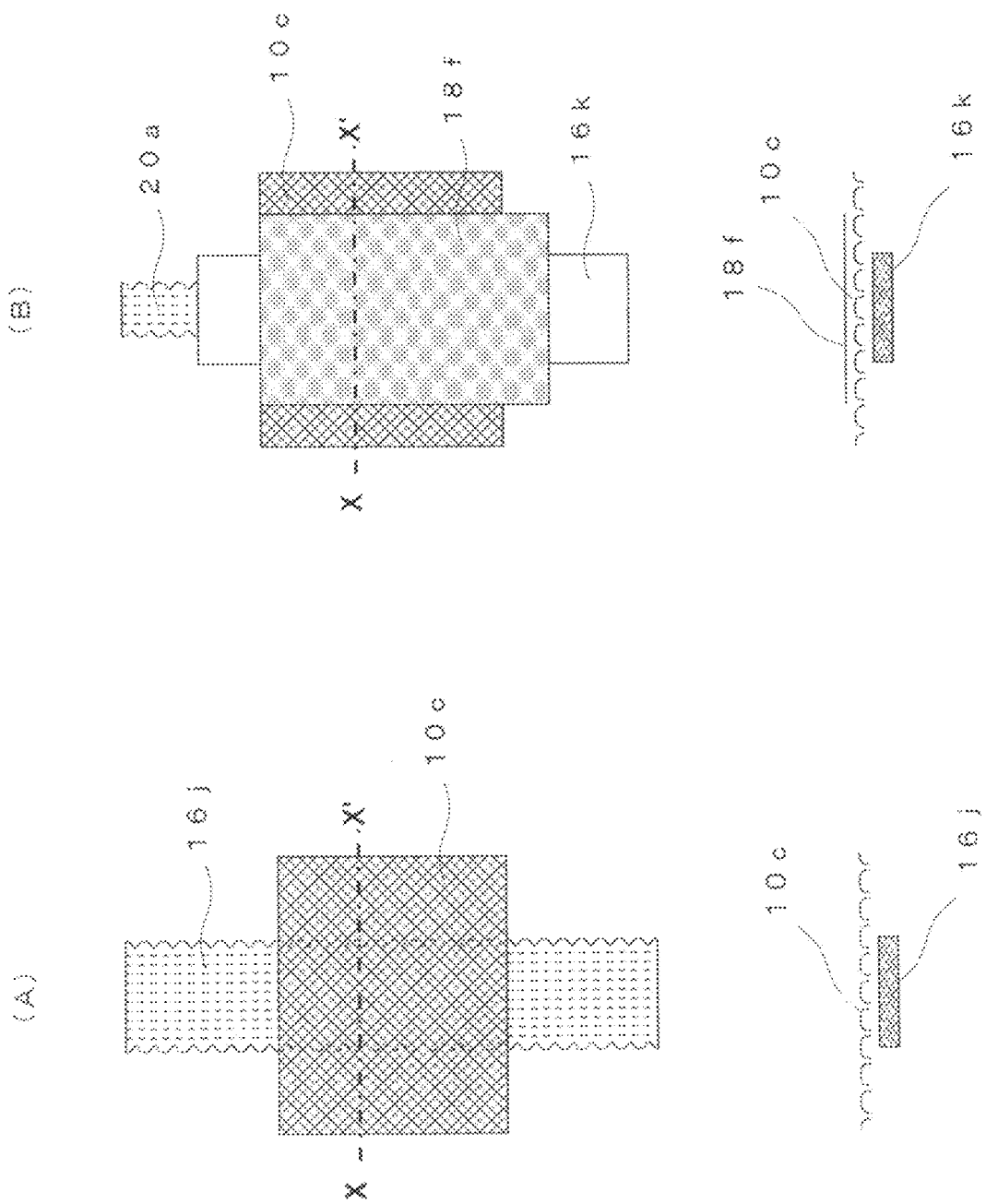
FIG. 11 are schematic plan views illustrating combinations of the liquid guide unit formed of a film having openings and the support member, and lateral end face views taken along the line X-X' of the plan views.

In this case, one preferred mode is to provide stretchability to the connection member (see FIG. 9(B) and FIG. 11). Thus, further stretchability can be given by the suspended structure like a hammock, whereby the proximate state of the liquid guide unit and the meatus urinarius can be more stably maintained even if the body position or the movement of the wearer changes.

Hereinafter, the combinations of the liquid guide unit and other components of the absorbent article is described.

Figure 8:
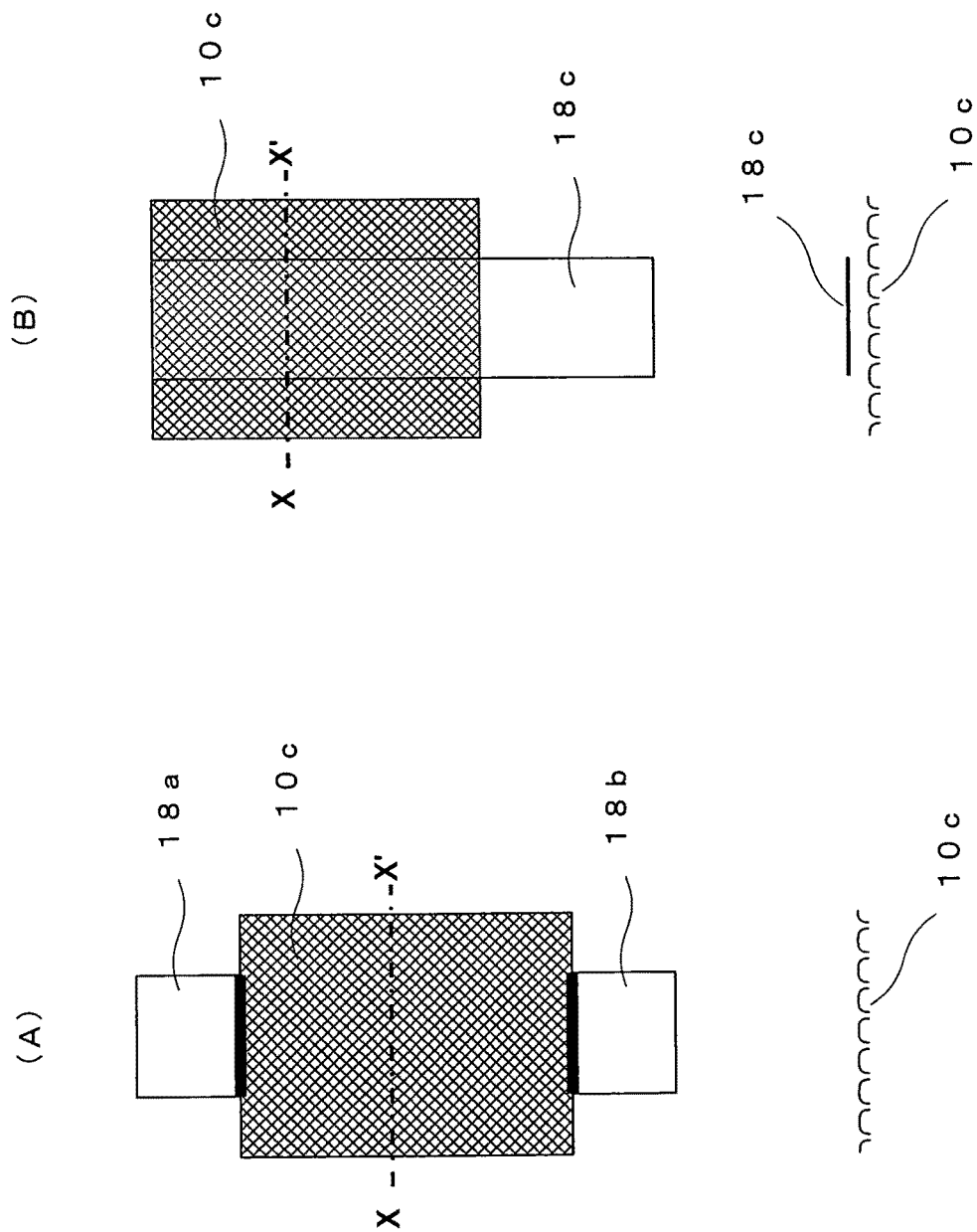
FIG. 8 are schematic plan views illustrating a combination of the liquid guide unit formed of a film having openings and the top sheet, and lateral end face views taken along a line X-X' of the plan views.
Figure 9:
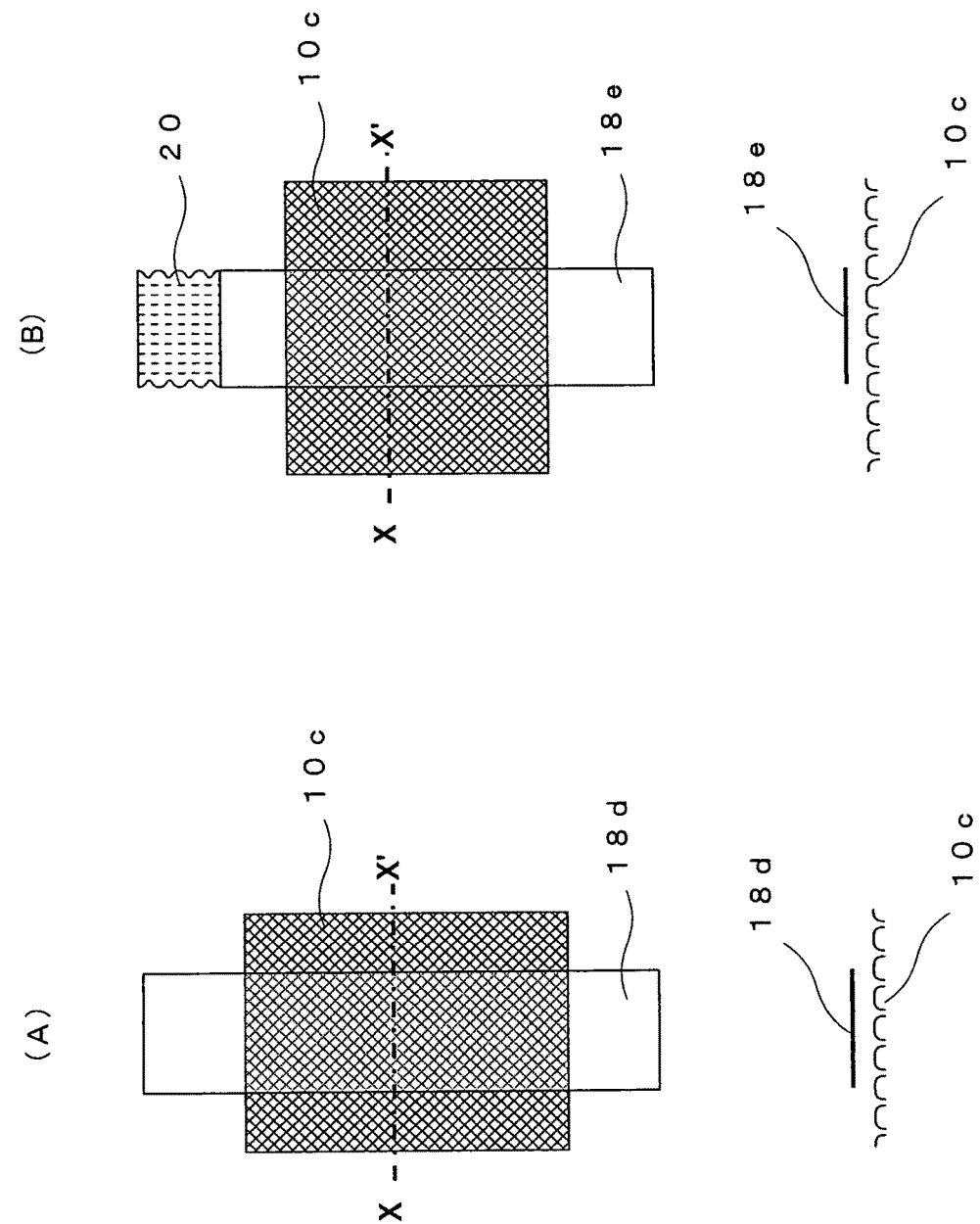
FIG. 9 are schematic plan views illustrating combinations of the liquid guide unit formed of a film having openings and the top sheet, and lateral end face views taken along the line X-X' of the plan views.

FIG. 8 and FIG. 9 are schematic plan views illustrating combinations of the liquid guide unit formed of a film having openings and the top sheet, and lateral end face views taken along the line X-X' of the plan views.

The liquid guide unit 10c illustrated in FIG. 8(A) is formed of a rectangular film having openings, and includes top sheets 18a and 18b at the front end and the rear end by way of a connection part (the black painted portion in the figure). The connection part may be formed by an adhesive. Further, the waist band (not shown) and the front end of the liquid guide unit 10c are connected by the top sheet 18a.

As seen in such mode, if the skin contact sheets 18a and 18b are provided on the absorber (not shown), and the front end of the liquid guide unit 10c and the skin contact sheet 18a are connected and the rear end of the liquid guide unit 10c and the skin contact sheet 18b are connected, the liquid guide unit 10c is suspended at the front end and the rear end by the skin contact sheets 18a and 18b to be in a suspended structure like a hammock, and the urine that moved on the liquid guide unit 10c of the urine received at the liquid guide unit 10c can be moved to the front side and the rear side, particularly to the rear side, through the skin contact sheets 18a and 18b.

The liquid guide unit 10c illustrated in FIG. 8(B) is formed of a rectangular film having openings, and includes a top sheet 18c extending from the front end to a position behind the rear end on thereon. The liquid guide unit 10c and the top sheet 18c are connected by the adhesive and the like at the overlapped portion. The waist band (not shown) and the front end of the liquid guide unit 10c are also connected.

The combination illustrated in FIG. 8(B) has the same effects as those of the combination illustrated in FIG. 8(A).

The liquid guide unit 10c illustrated in FIG. 9(A) is formed of a rectangular film having openings, and includes a top sheet 18d extending from a position in front of the front end to a position behind the rear end thereon. The waist band (not shown) and the liquid guide unit 10c are connected by the top sheet 18d.

The liquid guide unit 10c illustrated in FIG. 9(B) is basically the same as the liquid guide unit 10c illustrated in FIG. 9(A), but differs in that the front end of a top sheet 18e to be combined is connected to a stretchable member 20.

Figure 10:
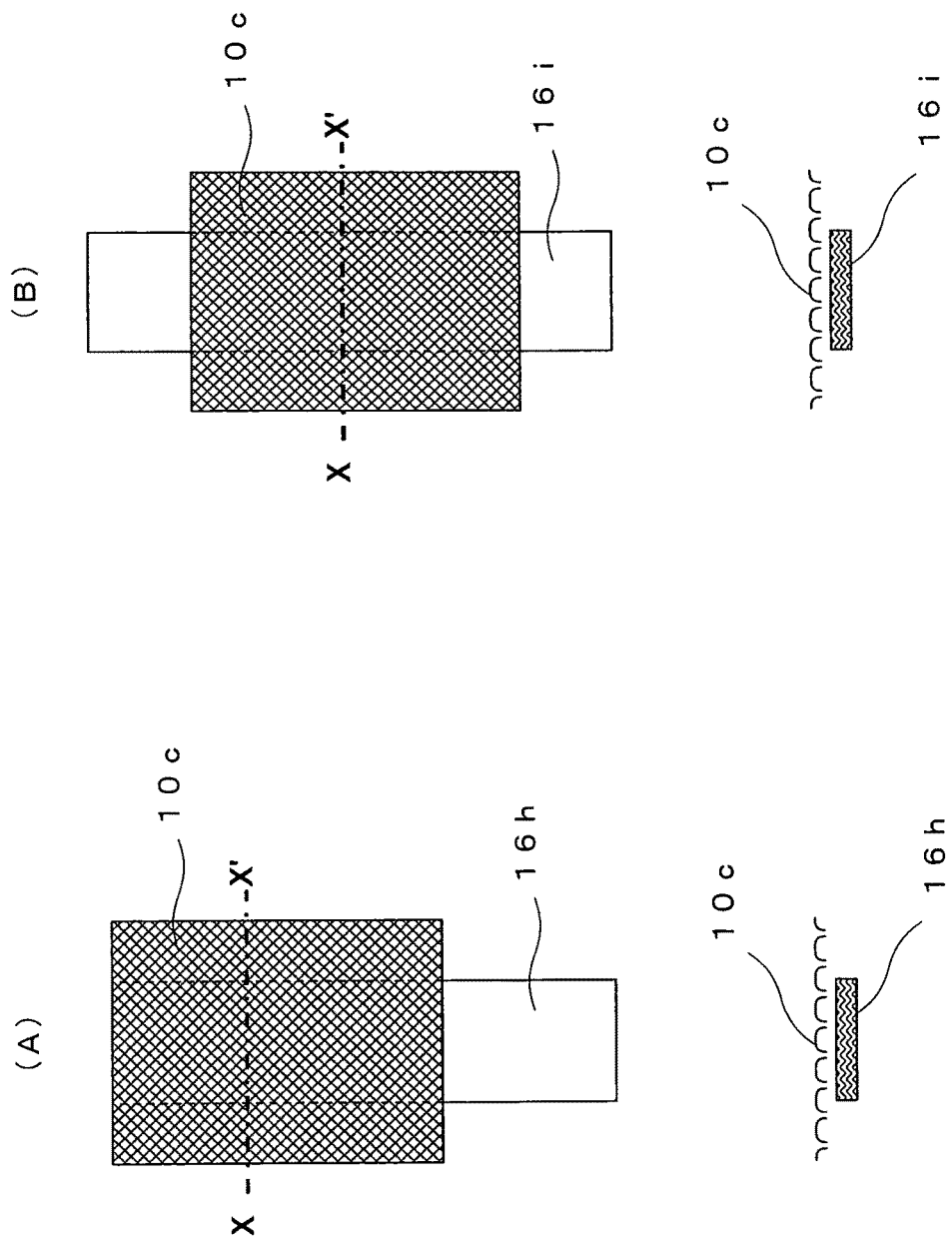
FIG. 10 are schematic plan views illustrating combinations of the liquid guide unit formed of a film having openings and the support member, and lateral end face views taken along the line X-X' of the plan views.

FIG. 10 and FIG. 11 are schematic plan views illustrating combinations of the liquid guide unit formed of a film having openings and the support member, and lateral end face views taken along the line X-X' of the plan views.

The liquid guide unit 10c illustrated in FIG. 10(A) is formed of a rectangular film having openings, and includes a sheet-form support member 16h extending from the front end to a position behind the rear end beneath the liquid guide unit 10c.

The liquid guide unit 10c illustrated in FIG. 10(B) is formed of a rectangular film having openings, and includes a sheet-form support member 16i extending from a position in front of the front end to a position behind the rear end beneath the liquid guide unit 10c. Further, the waist band (not shown) and the liquid guide unit 10c are connected by the support member 16i.

The liquid guide unit 10c illustrated in FIG. 11(A) is basically the same as the liquid guide unit illustrated in FIG. 10(B), but differs in that the sheet-form support member 16j to be combined has stretchability.

The liquid guide unit 10c illustrated in FIG. 11(B) is basically the same as the liquid guide unit 10c illustrated in FIG. 10(B), but differs in that the front end of the sheet-form support member 16k to be combined is connected to a stretchable member 20a, and has a top sheet 18f extending from the front end to a position behind the rear end thereon.

Figure 12:
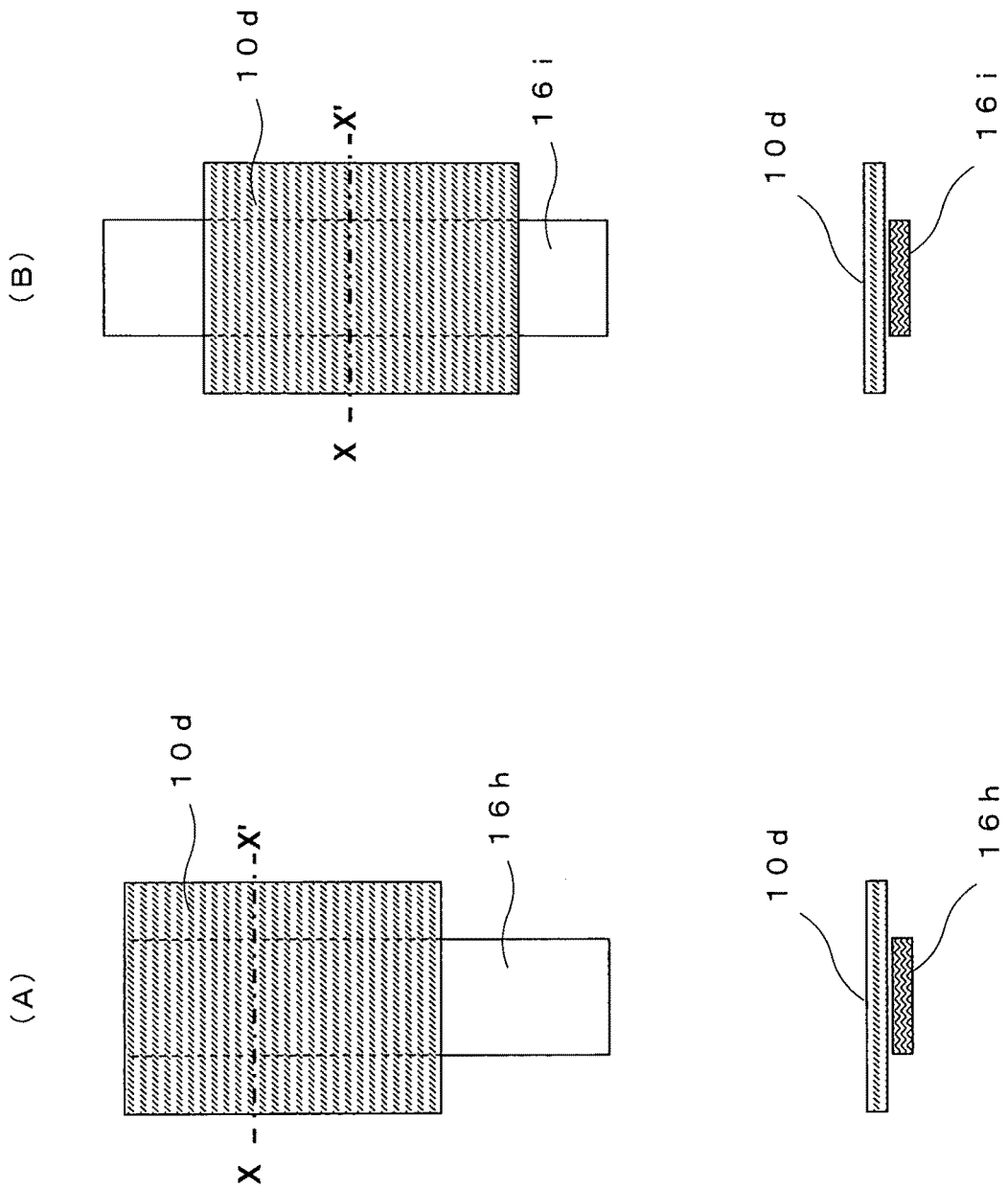
FIG. 12 are schematic plan views illustrating combinations of the liquid guide unit formed of a bulky nonwoven fabric and the support member, and lateral end face views taken along the line X-X' of the plan views.

FIG. 12 are schematic plan views illustrating combinations of the liquid guide unit formed of a bulky nonwoven fabric and the support member, and lateral end face views taken along the line X-X' of the plan views.

The liquid guide unit 10d illustrated in FIG. 12(A) is formed of a rectangular bulky nonwoven fabric, and includes a sheet-form support member 16h extending from the front end to a position behind the rear end beneath the liquid guide unit 10d.

The liquid guide unit 10d illustrated in FIG. 12(B) is formed of a rectangular bulky nonwoven fabric, and includes a sheet-form support member 16i extending from a position in front of the front end to a position behind the rear end beneath the liquid guide unit 10d. The waist band (not shown) and the liquid guide unit 10d are connected by the sheet-form support member 16i.

Figure 13:
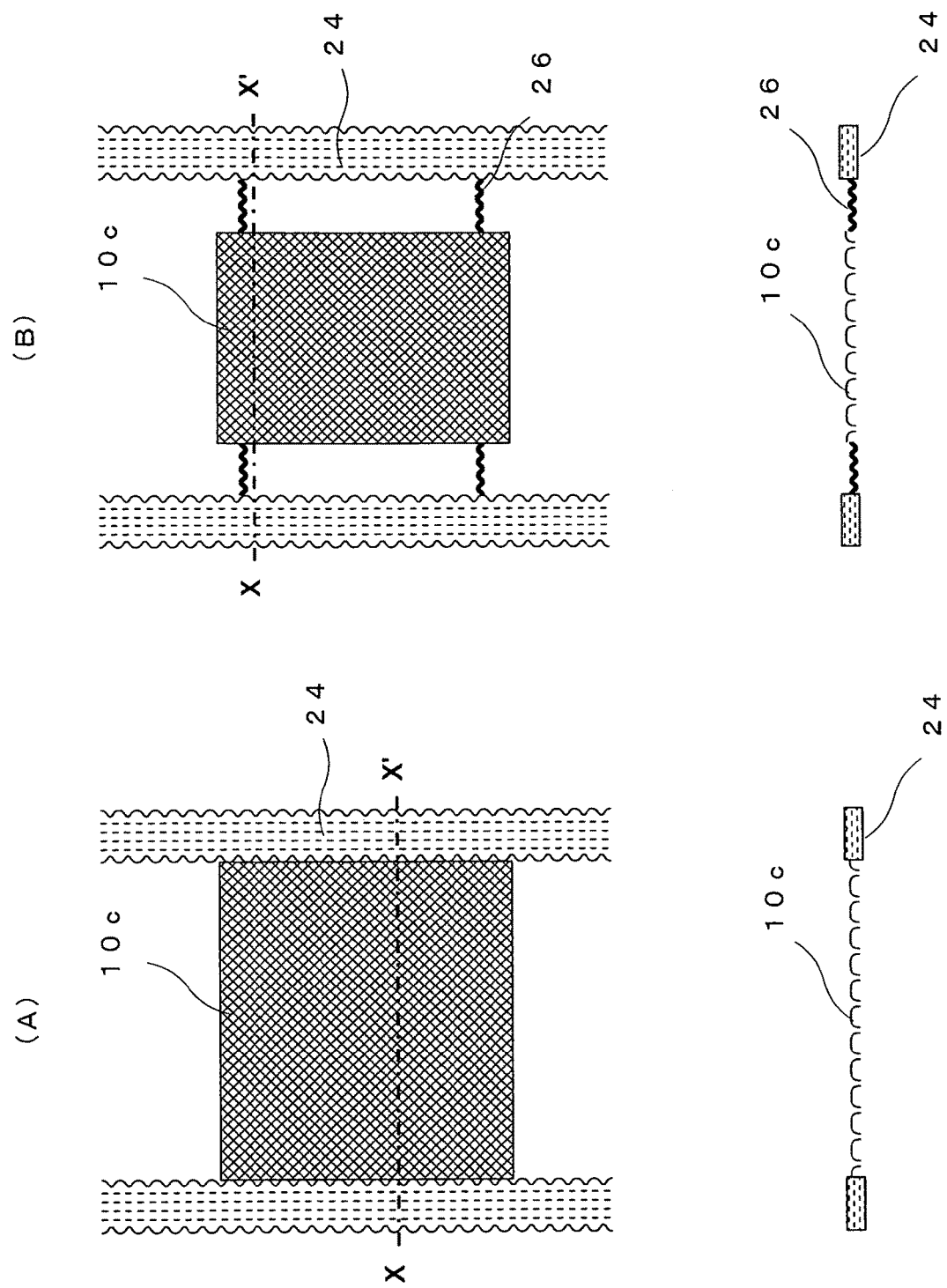
FIG. 13 are schematic plan views illustrating combinations of the liquid guide unit formed of a film having openings and the side edge band, and lateral end face views taken along the line X-X' of the plan views.
Figure 14:
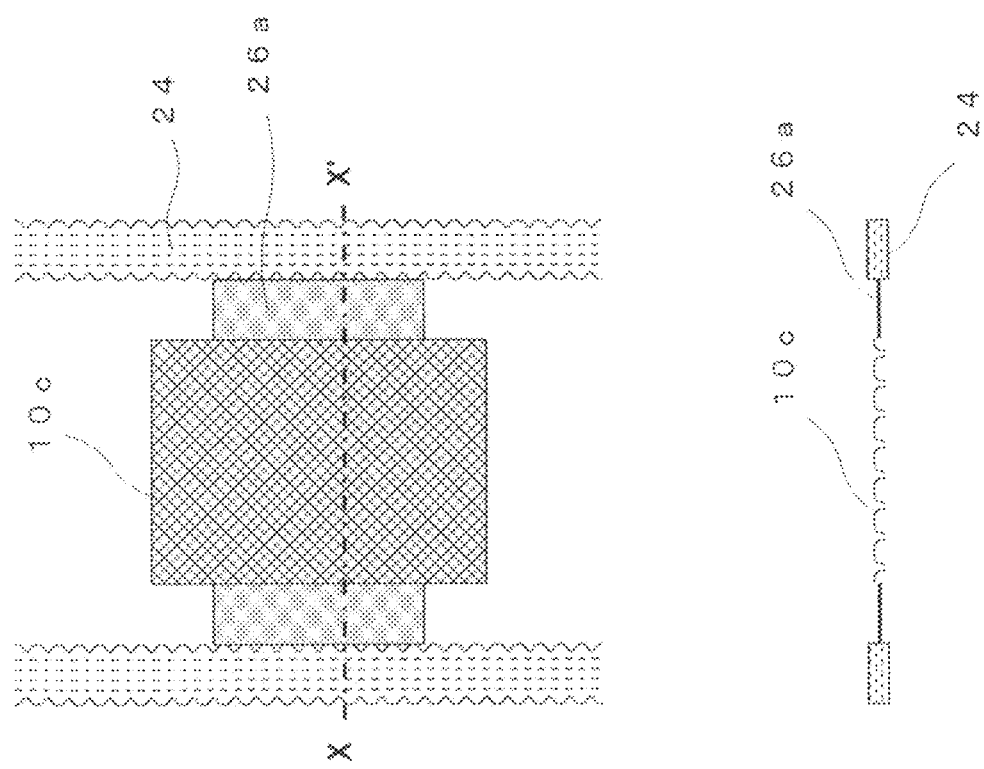
FIG. 14 are a schematic plan view illustrating a combination of the liquid guide unit formed of a film having openings and the side edge band, and a lateral end face view taken along the line X-X' of the plan view.

FIG. 13 and FIG. 14 are schematic plan views illustrating a combination of the liquid guide unit formed of a film having openings and the side edge bands, and lateral end face views taken along the line X-X' of the plan views.

The liquid guide unit 10c illustrated in FIG. 13(A) is formed of a rectangular film having openings, and the left and right ends thereof are directly connected to the side edge bands 24 provided along the ends of the side parts (not shown) of the leak preventer.

The liquid guide unit 10c illustrated in FIG. 13(B) is formed of a rectangular film having openings, and the left and right ends thereof are connected, respectively at two points, to the side edge bands 24 provided along the ends of the side parts (not shown) of the leak preventer by a connection member 26 having stretchability.

The liquid guide unit 10c illustrated in FIG. 14 is formed of a rectangular film having openings, and the left and right ends thereof are connected to side edge bands 24 provided along the ends of the side parts (not shown) of the leak preventer by a connection member (connection sheet) 26a that does not have stretchability.

Figure 15:
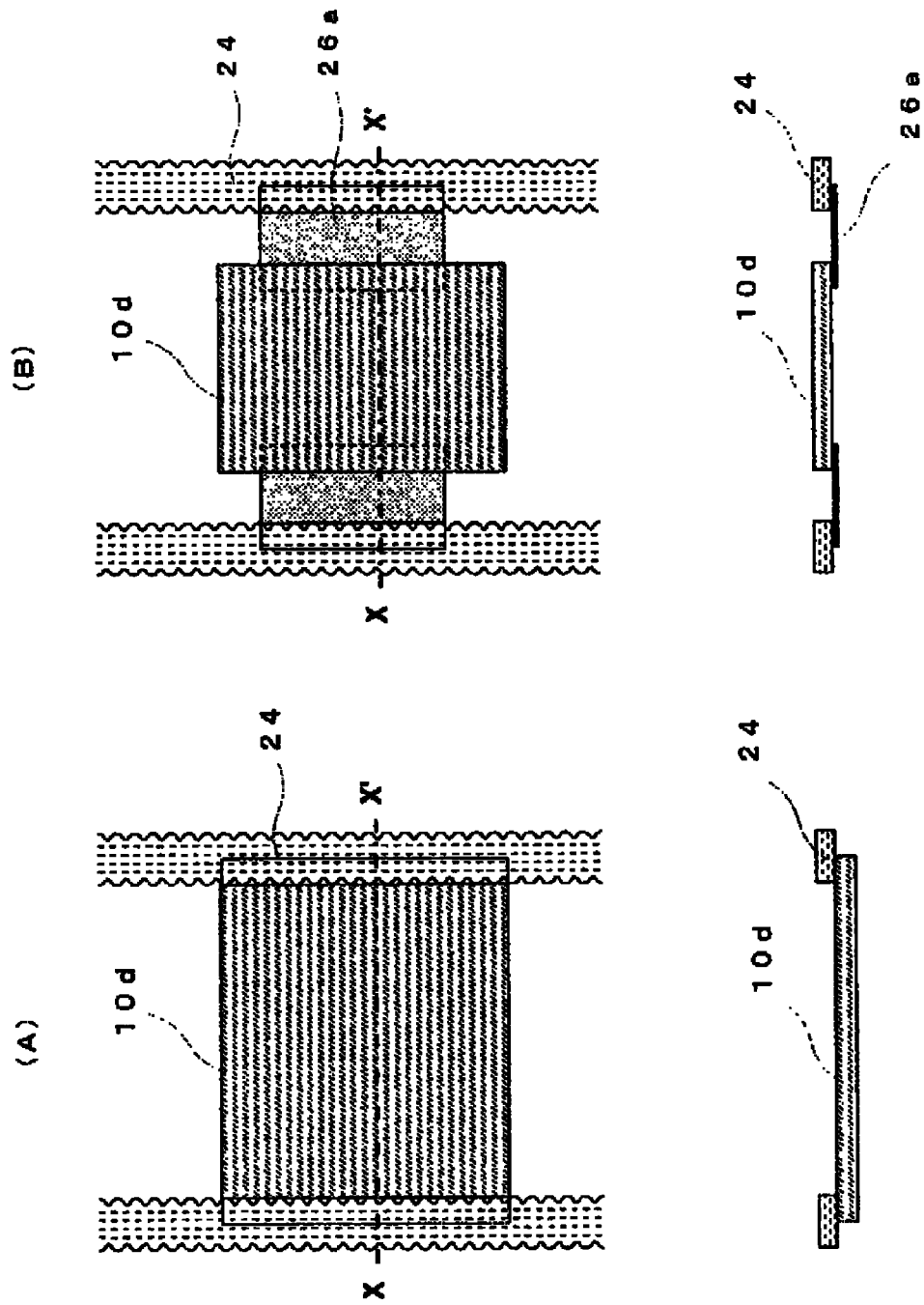
FIG. 15 are schematic plan views illustrating combinations of the liquid guide unit formed of a bulky nonwoven fabric and the side edge band, and lateral end face views taken along the line X-X' of the plan views.

FIG. 15 are schematic plan views illustrating combinations of the liquid guide unit formed of a bulky nonwoven fabric and the side edge bands, and lateral end face views taken along the line X-X' of the plan views.

The liquid guide unit 10d illustrated in FIG. 15(A) is formed of a rectangular nonwoven fabric, and the left and right ends thereof are directly connected to the side edge bands 24 provided along the ends of the side parts (not shown) of the leak preventer.

The liquid guide unit 10d illustrated in FIG. 15(B) is formed of a rectangular nonwoven fabric, and the left and right ends thereof are connected to the side edge bands 24 provided along the ends of the side parts (not shown) of the leak preventer by the connection members (connection sheet) 26a that do not have stretchability.

FIG. 16 are schematic plan views illustrating combinations of the liquid guide unit formed of a film having openings, the side edge band, and the support member, and longitudinal end face views taken along the line Y-Y' of the plan views.

The liquid guide unit 10c illustrated in FIG. 16(A) is formed of a rectangular film having openings, has a sheet-form support member 16h extending from the front end to the position behind the rear end beneath the liquid guide unit 10c and a band-form support member 16l extending from the position on the left of the left end of the liquid guide unit 10c to the position on the right of the right end beneath the support member 16h, and is connected to the side edge bands 24 provided along the ends of the side parts (not shown) of the leak preventer by the band-form support member 16l.

The liquid guide unit 10c illustrated in FIG. 16(B) is formed of a rectangular film having openings, has a sheet-form support member 16m extending from the position on the left of the left end of the liquid guide unit 10c to the position on the right of the right end beneath the liquid guide unit 10c, and is connected to the side edge bands 24 provided along the ends of the side parts (not shown) of the leak preventer by the band-form support member 16m.

FIG. 17 are a schematic plan view illustrating a combination of the liquid guide unit formed of a film having openings, the side edge bands, and the support member, and lateral end face views taken along the line X-X' of the plan view.

The liquid guide unit 10c illustrated in FIG. 17 is formed of a rectangular film having openings, has two band-form support members 16n extending from the positions on the left of the left end of the liquid guide unit 10c to the positions on the right of the right end beneath the liquid guide unit 10c in an X-shape, and is connected to the side edge bands 24 provided along the ends of the side parts (not shown) of the leak preventer by the band-form support members 16*n*.

FIG. 18 are a schematic plan view illustrating a combination of the liquid guide unit formed of a film having openings and the support member, and a lateral end face view taken along the line X-X' of the plan view.

The liquid guide unit 10*c* illustrated in FIG. 18 is formed of a rectangular film having openings, and has a support member 16*o* made of cylindrical urethane foam beneath the liquid guide unit 10*c*. In this mode, a space is ensured between the liquid guide unit 10*c* and the absorber (not shown).

FIG. 19 are schematic views illustrating combinations of the liquid guide unit formed of a film having openings and the support member. FIG. 19(A) are a plan view and a lateral end face view taken along the line X-X' of the plan view. FIG. 19(B) are a plan view and a longitudinal end face view taken along the line Y-Y' of the plan view.

The liquid guide unit 10*c* illustrated in FIG. 19(A) is formed of a rectangular film having openings, and the sheet-form absorber used as the absorber is arranged beneath the liquid guide unit 10*c* so as to have one upward projection at the central part in the left and right direction and functions as the support member 16*p*.

The liquid guide unit 10*c* illustrated in FIG. 19(B) is formed of a rectangular film having openings, and the sheet-form absorber used as the absorber is arranged beneath the liquid guide unit 10*c* so as to have three upward projections in the front-rear direction and functions as the support member 16*q*.

In these modes, a space is ensured between the liquid guide unit 10*c* and the absorber (not shown).

FIG. 20 are schematic views illustrating a combination of the liquid guide unit formed of a molded foam body and the side edge bands. FIG. 20(A) is a plan view, FIG. 20(B) is a longitudinal end face view taken along the line Y-Y' of FIG. 20(A), and FIG. 20(C) is a perspective view.

The liquid guide unit 10*f* illustrated in FIG. 20 is formed of a molded foam body having a recessed surface on the upper side. More specifically, the liquid guide unit includes a bowl-shaped body and a tubular part provided at the rear part of the body, and the interior of the tubular part and the interior of the body are communicated.

The liquid guide unit 10*f* is formed of a molded foam body such as foam polypropylene, and is molded by subjecting a foam sheet to, for example, heat press molding.

The liquid guide unit 10*f* illustrated in FIG. 20 is connected to the side edge bands 24 provided along the ends of the side parts (not shown) of the leak preventer by the connection members 26*b* having stretchability at two points respectively on the left and the right thereof.

In the liquid guide unit 10*f* illustrated in FIG. 20, the flow of discharged urine directly collides to the bowl-shaped body, and is collected at the bottom of the body, passes through the tubular part and moves to the absorber.

Figure 21:
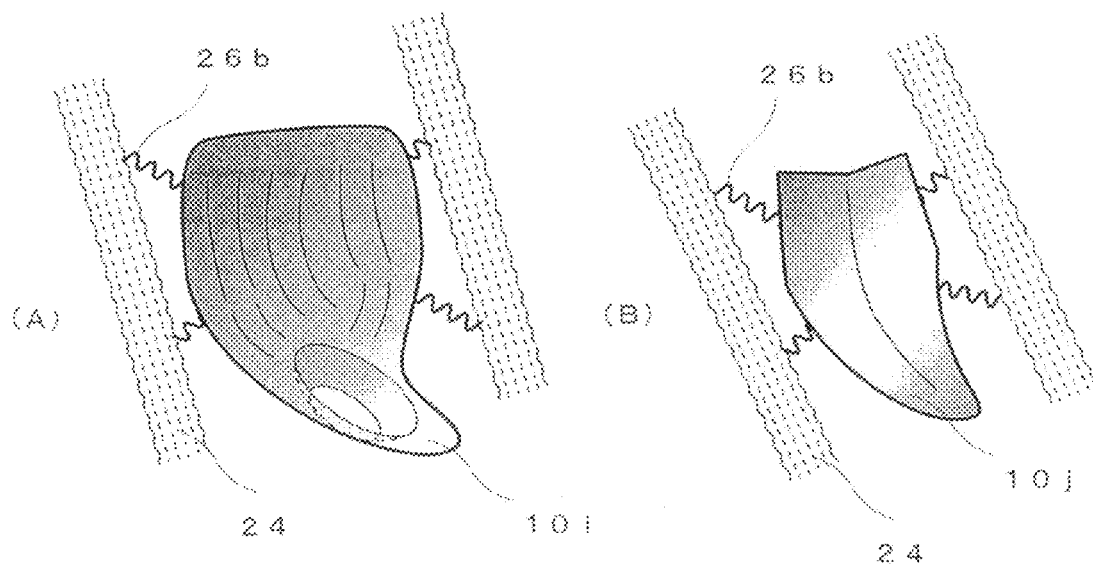
FIG. 21 are schematic perspective views illustrating other combinations of the liquid guide unit formed of the molded foam body and the side edge bands.

FIG. 21 are schematic perspective views illustrating another combination of the liquid guide unit formed of the molded foam body and the side edge bands.

The liquid guide unit 10*i* illustrated in FIG. 21(A) is formed of a molded foam body having a recessed surface on the upper side. More specifically, the liquid guide unit includes the body forming a shallow recessed surface with small streak-shaped depressions, and a large plate-shaped recessed part provided at the rear part of the body, and a hole is formed at the bottom of the recessed part.

The liquid guide unit 10*i* is formed of a molded foam body such as polypropylene foam, and is molded by subjecting a foam sheet to heat press molding.

The liquid guide unit 10*i* illustrated in FIG. 21(A) is connected to the side edge bands 24 provided along the ends of the side parts (not shown) of the leak preventer by the connection members 26*b* having stretchability at two points respectively on the left and the right.

In the liquid guide unit 10*i* illustrated in FIG. 21(A), the discharged urine moves along the small streak-shaped depressions to be easily collected at the recessed part, and the urine collected at the recessed part moves to the absorber from the hole formed at the bottom.

The liquid guide unit 10*j* illustrated in FIG. 21(B) is formed of a molded foam body having a recessed surface on the upper side. More specifically, it is molded to a recessed surface-shape so as to form a bottom at a central part in the left and the right direction.

The liquid guide unit 10*j* is formed of a molded foam body such as foam polypropylene, and is molded by subjecting a foam sheet to the heat press molding.

The liquid guide unit 10*j* illustrated in FIG. 21(B) is connected to the side edge bands 24 provided along the ends of the side parts (not shown) of the leak preventer by the connection members 26*b* having stretchability at two points respectively on the left and the right.

In the liquid guide unit 10*j* illustrated in FIG. 21(B), the discharged urine is collected at the bottom of the recess, and the flow of urine with force is moved to the rear side along the recess, and moved from the rear end of the liquid guide unit 10*j* to the absorber.

When wearing the conventional absorbent article, the central part in the front-rear direction is positioned at a position under the crotch of the wearer, and thus is thinned by being sandwiched by both legs, whereby it is difficult for the urine to move to the rear side, and it is generally difficult to efficiently use the absorber at the rear body part to absorb urine. In the "two-floor structure", if the absorber at the rear body part cannot be efficiently used, the absorbing capacity as a whole does not become large, which becomes a problem.

Each liquid guide unit illustrated in FIG. 20, FIG. 21(A) and FIG. 21(B) is configured to match the size of the part under the crotch with the molded foam body, and thus maintains the shape and barely deforms even if sandwiched by both legs, whereby the urine can smoothly move to the rear body part.

The state of movement of the urine in the absorbent article of the present invention is described.

FIG. 22 are schematic views illustrating the state of movement of urine in one example of the absorbent article of the present invention. FIG. 22(A) is a plan view, and FIG. 22(B) is a lateral end face view taken along the line X-X' of FIG. 22(A). Of the configuring members of the absorbent article of the present invention, only the side parts of the leak preventer, the liquid guide unit, the support member, and the urine/feces separating member are illustrated in FIG. 22(A), and only the liquid guide unit is illustrated in FIG. 22(B).

As illustrated in FIG. 22, the urine discharged from the meatus urinarius M collides to the liquid impermeable liquid guide unit 10*a* supported by the support member 16 at the X mark, as illustrated with an arrow, moves radially on the surface of the liquid guide unit 10*a*, and is absorbed at wide range by the absorber (not shown) while moving and diffusing mainly to the lower side from the peripheral edge of the liquid guide unit 10*a*.

In the case of the conventional absorbent article not including the liquid guide unit used in the present invention, the urine discharged from the meatus urinarius positioned on the front body part is first absorbed by the absorber at the vicinity thereof, and gradually diffused to the periphery when the relevant site is saturated. The diffusion of the urine reaches the distal end of the front body part on the front side but is blocked by the narrowed portion under the crotch on the rear side. Thus, the diffusion of urine is blocked by the narrowed portion under the crotch and the passage to the rear body part is closed not only in the face-down position and the side-lying position where the absorber at the front body part tends to be used but also in the sitting position or the face-up position where the urine tends to easily move to the rear body part by gravity, and thus the urine can move only up to the vicinity of the anus at the most. Therefore, in the conventional absorbent article, the majority of the rear body part is barely used in any body position.

In the present invention, through the use of the liquid guide unit, the discharged urine is moved particularly in the direction of the rear body part in wide range before being absorbed by the absorber existing near the meatus urinarius, and hence the absorber can be used to about half of the rear body part in the face-down position and to the rear end of the rear body part in the face-up position. Thus, the utilization efficiency of the entire absorber can be greatly enhanced since the urine can move in a wide range from the front body part to the rear body part in any body position by using the liquid guide unit.

In the mode illustrated in FIG. 22, the urine/feces separating member 28 is arranged to connect a pair of side parts of the leak preventer 12, thereby preventing the urine from mixing with the feces. If the feces receiving part is spaced apart from the absorber thereunder by a feces barrier, the urine and the feces do not mix even if the urine moves to the entire rear body part.

FIG. 23 are schematic views illustrating the state of movement of urine in another example of the absorbent article of the present invention. FIG. 23(A) is a plan view, and FIG. 23(B) is a lateral end face view taken along the line X-X' of FIG. 23(A). Of the configuring members of the absorbent article of the present invention, only the side parts of the leak preventer, the liquid guide unit, the support member, and the urine/feces separating member are illustrated in FIG. 23(A), and only the liquid guide unit is illustrated in FIG. 23(B).

As illustrated in FIG. 23, the urine discharged from the meatus urinarius M collides to the liquid permeable liquid guide unit 10*b* supported by the support member 16 at the X mark, as illustrated with arrows, moves radially on the surface of the liquid guide unit 10*b* while moving to the lower side, and diffuses and is absorbed at wide range in a short time by the absorber (not shown).

Figure 24:
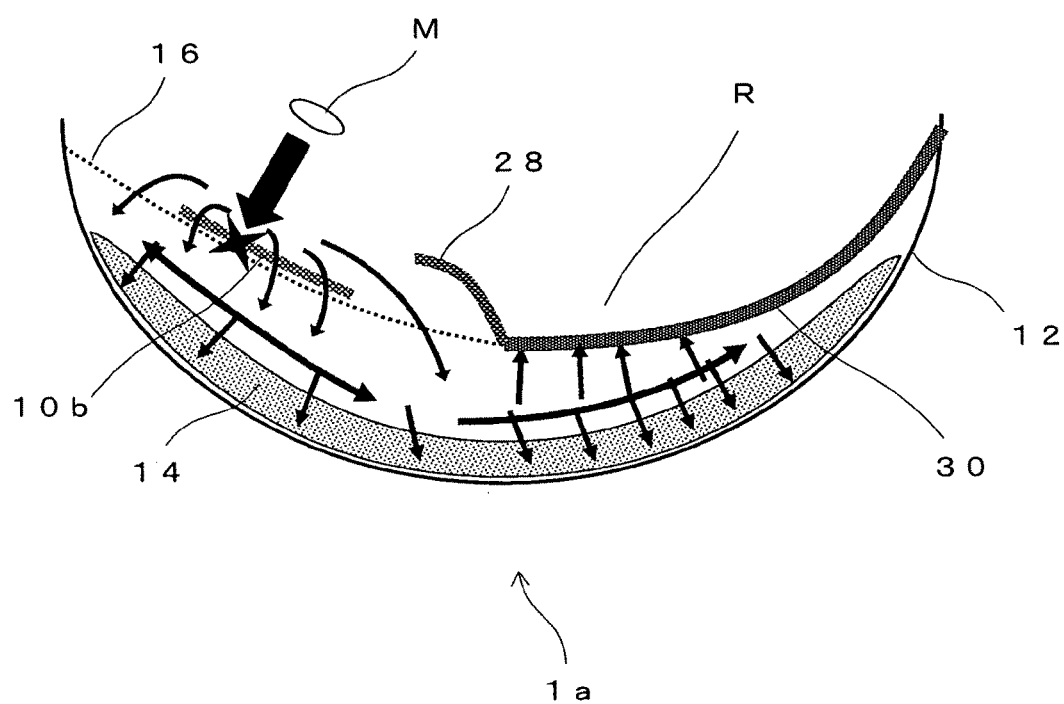
FIG. 24 is a schematic longitudinal end face view illustrating the state of movement of urine in the absorbent article of the present invention illustrated in FIG. 23.

FIG. 24 is a schematic longitudinal end face view illustrating a state of movement of urine in the absorbent article of the present invention illustrated in FIG. 23. FIG. 24 illustrates a longitudinal end face view at the central part in the left and right direction of the absorbent article.

As illustrated in FIG. 24, as illustrated with arrows, the urine discharged from the meatus urinarius M of the wearer of the absorbent article 1*a* collides to the liquid permeable liquid guide unit 10*b* supported by the support member 16 at the mark X and connected to the leak preventer 12, and a part of urine moves to the lower side from the peripheral edge of the liquid guide unit 10*b* to be absorbed by the absorber 14, and the remaining urine passes through the inside of the liquid guide unit 10*b* to be absorbed by the absorber 14. At the front body part, the urine moves forward on the front side from the portion where the discharged urine collides at the surface of the liquid guide unit 10*b*, and the urine moves backward at the rear side from the portion. At the rear body part, the urine moves backward. In this case, as illustrated in the figure, if the absorbent article 1*a* includes the urine/feces separating member 28 and the feces barrier 30, the urine that moved on the surface of the liquid guide unit 10*b* is blocked by the urine/feces separating member 28 and the urine that moved backward through the internal space of the leak preventer 14 is blocked by the feces barrier 30, and thus the urine does not move to the feces receiving part R partitioned by the urine/feces separating member 28 and the feces barrier 30, and as a result, the urine and the feces can be separated.

Figure 26:
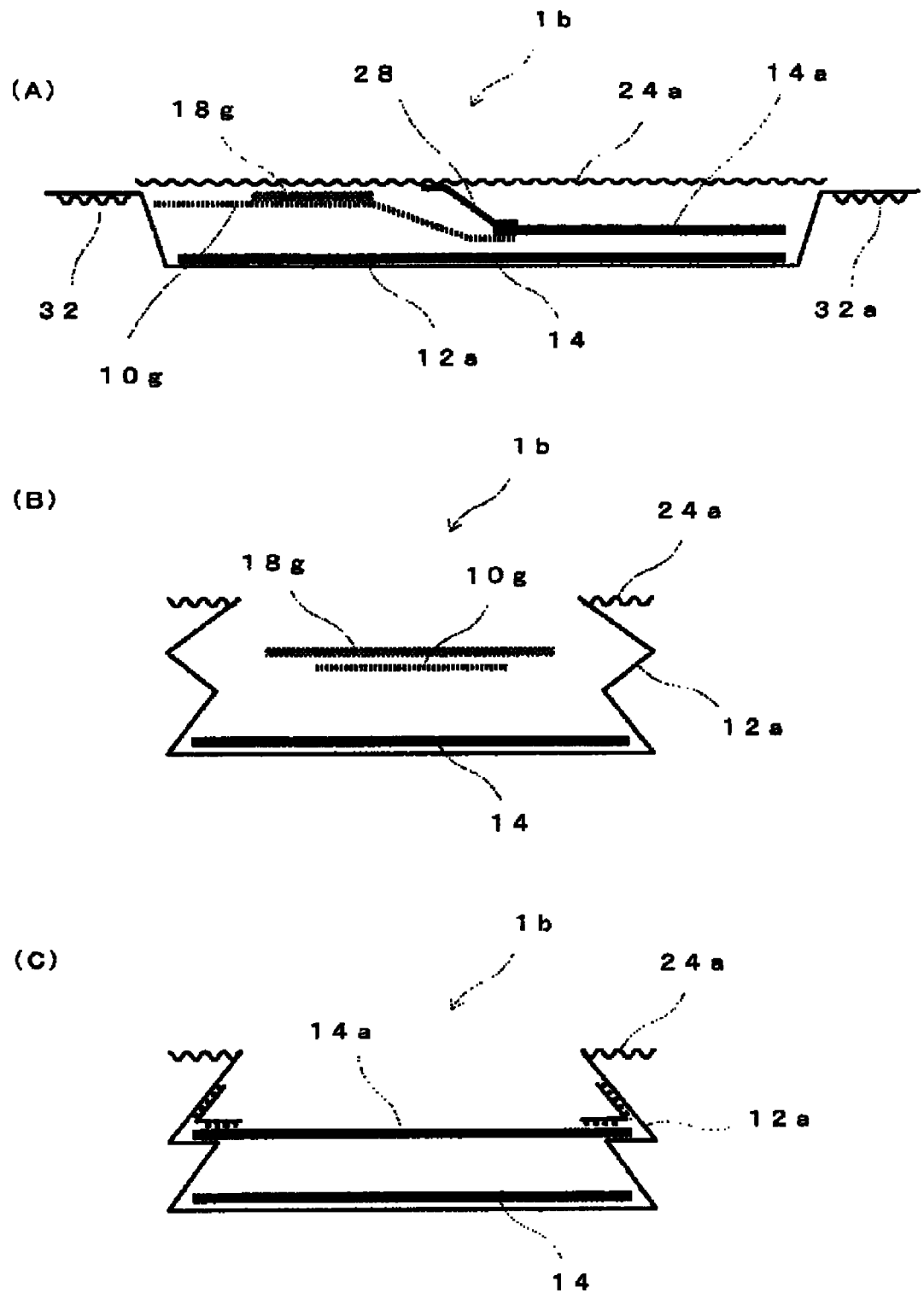
FIG. 26 are schematic views illustrating further another example of the absorbent article of the present invention.

FIG. 25 and FIG. 26 are schematic views illustrating further another example of the absorbent article of the present invention. FIG. 25(A) is a plan view, and FIG. 25(B) is a partially enlarged plan view of the liquid guide unit and the top sheet before and while the absorbent article being worn. FIG. 26(A) is a longitudinal end face view taken along the line Y-Y' of FIG. 25(A), FIG. 26(B) is a lateral end face view taken along the line $X_1$-$X_1$' of FIG. 25(A), and FIG. 26(C) is a lateral end face view taken along the line $X_2$-$X_2$' of FIG. 25(A).

The absorbent article 1*b* illustrated in FIG. 25 and FIG. 26 basically includes: a leak preventer 12*a* having a bottom surface part extending in the front-rear direction and side parts rising upward on both left and right sides of the bottom surface part; an absorber 14 capable of absorbing a body fluid, the absorber containing super absorbent polymer and being placed in an internal space formed by the bottom surface part and the side parts of the leak preventer 12*a* in at least one layer; and a liquid guide unit 10*g* placed in a front body part of the internal space, at a position where the flow of discharged urine directly collides therewith, and, when urine is discharged, moving the urine from the position where the urine has collided therewith to other positions.

The side parts of the leak preventer 12*a* are folded to be an accordion shape, the internal space is divided to two upper and lower levels, where the absorber 14 is arranged at the lower level and the feces receiving absorber 14*a* is arranged on the upper side of the absorber 14 at the rear body part of the upper level, the front end thereof being connected to the rear end of the liquid guide unit 10*g*. The feces receiving absorber 14*a* is a super absorbent sheet obtained through a method of coating the SAP-dispersed slurry on the nonwoven fabric, the SAP layer being arranged on the lower side and the nonwoven fabric layer being arranged on the upper side, and is connected to the inner surface of the leak preventer 12*a* by adhesive and the like at both left and right ends thereof.

The front end of the leak preventer 12*a* is connected with the waist band 32, and the waist band 32 is connected with the front end of the liquid guide unit 10*g*.

The rear end of the leak preventer 12*a* is connected with the waist band 32*a*, and connecting parts 34 for replaceably connecting to the waist band 32 connected to the front end of the leak preventer 12*a* are connected to the left and right ends of the waist band 32*a*.

A pair of side edge bands 24*a* are arranged at the left and right side parts of the leak preventer 12*a* along the ends thereof, and the pair of side edge bands 24*a* are connected to each other at the central part in the front-rear direction to form an X-shape.

The front end of the urine/feces separating member 28 is connected to the lower surface of the connection parts of the pair of side edge bands 24*a*, and the rear end of the urine/feces separating member 28 is connected to the front end of the feces receiving absorber 14*a* with the rear end of the liquid guide unit 10*g*. Thus, the absorbent article 1*b* has a "two-floor structure" in which the feces receiving absorber 14*a* is arranged on the leak preventer 12*a* via the absorber 14 at the rear end to absorb the urine with the absorber 14 on the leak preventer 12*a* and accommodate the feces on the upper side of the feces receiving absorber 14*a*.

The liquid guide unit 10g is formed of a stretchable net (e.g., a rubber filament made of SEBS and EVA, e.g., 60d). The top sheet 18g connected to the upper surface of the liquid guide unit 10g is made of nonwoven fabric (e.g., thermal bond nonwoven fabric), where slits in the left and right direction is arranged in parallel. Before the absorbent article being worn, the liquid guide unit 10g are not stretched, and the slits of the top sheet 18g are closed (see the left view of FIG. 25(B)), but while being worn, the liquid guide unit 10g is stretched and the slits of the top sheet 18g are opened (see the right view of FIG. 25(B)).

The shape of liquid guide unit 10g can follow the shape of the body surface of the wearer when the absorbent article is worn as it has stretchability.

The absorbent article 1b includes two sheet-form absorbers including the absorber 14 and the feces receiving absorber 14a. Therefore, the absorbent article 1b is extremely thin with a thickness of between ½ and ⅓ compared to the conventional absorbent article using a powder absorber mixed with powdered wood pulp and SAP, but is an absorbent article having an extremely high area utilization efficiency as practically all the portions in the front-rear direction and the vertical direction of the absorber can be used to absorb the urine due to the liquid guide unit. Therefore, the absorbing ability that can sufficiently afford to receive the urine discharge of three or more times is normally provided.

The absorbent article 1b has an urine/feces separating function due to the urine/feces separating member 28 and the like, and thus diaper rash rarely occurs even if used for a long period of time, and the area which becomes dirty of the buttock of the wearer is small even when the wearer defecates.

Figure 27:
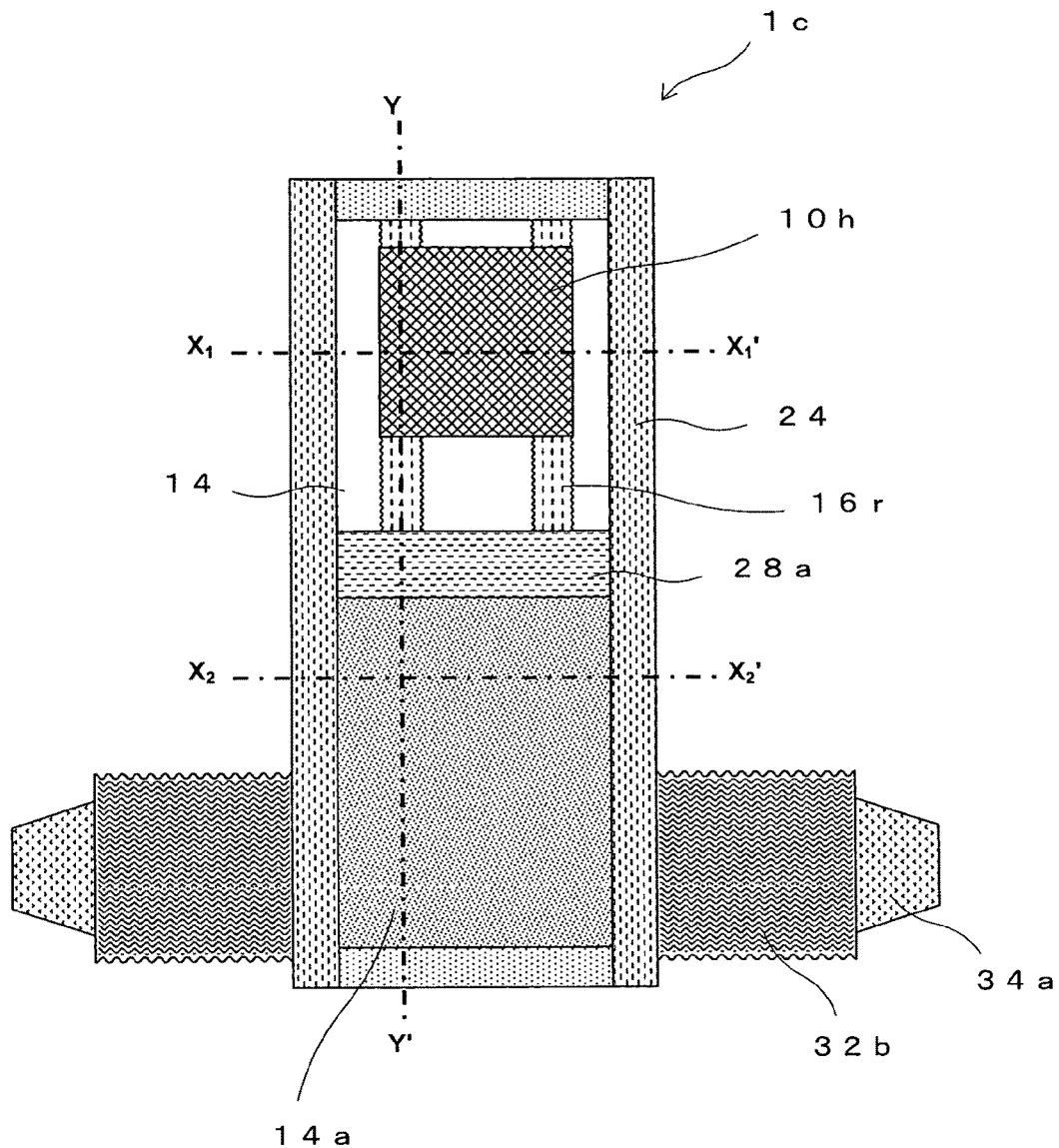
FIG. 27 is a schematic view illustrating further another example of the absorbent article of the present invention.
Figure 28:
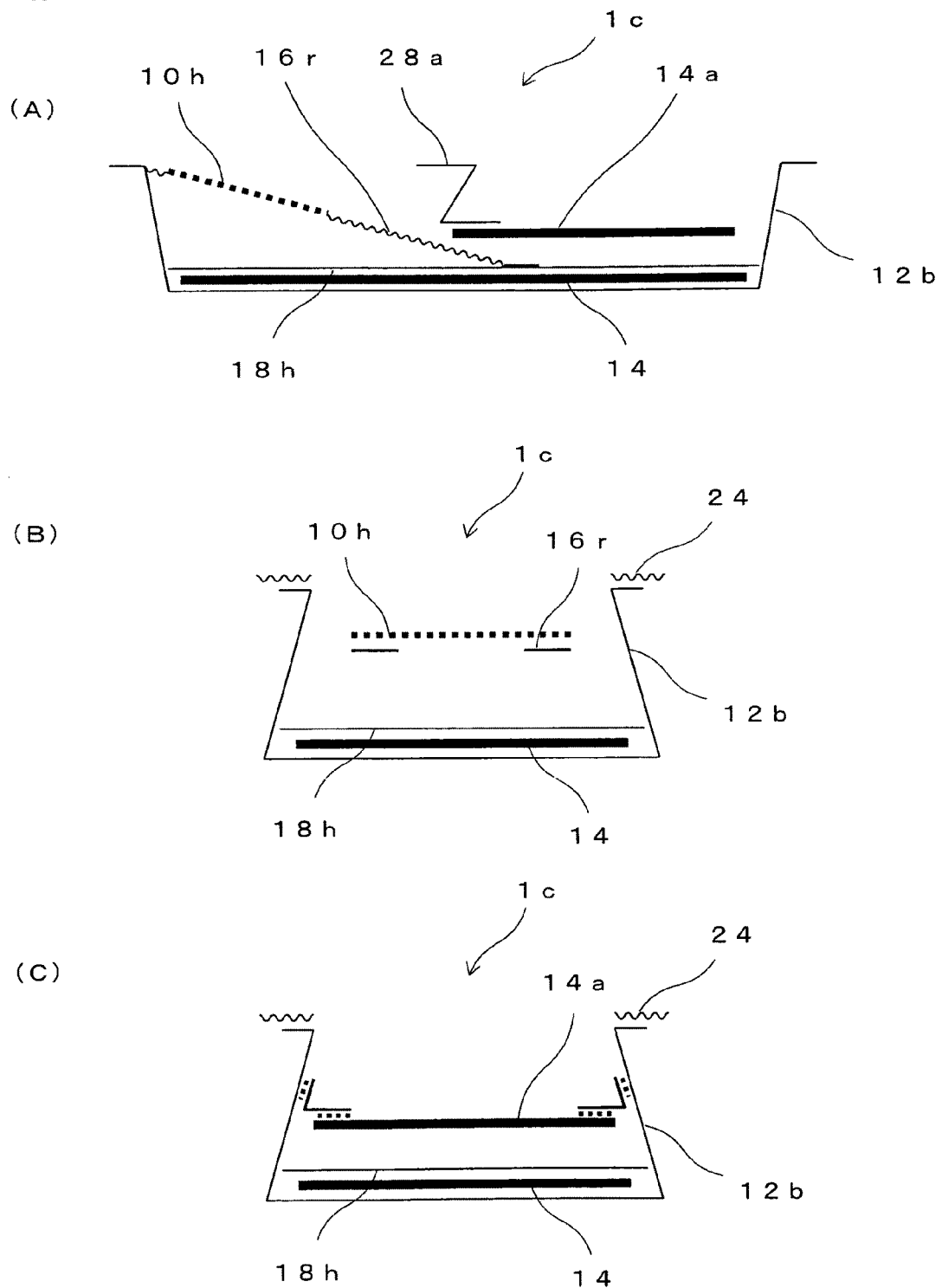
FIG. 28 are schematic views illustrating further another example of the absorbent article of the present invention.

FIG. 27 and FIG. 28 are schematic views illustrating further another example of the absorbent article of the present invention. FIG. 27 is a plan view, FIG. 28(A) is a longitudinal end face view taken along the line Y-Y' of FIG. 27, FIG. 28(B) is a lateral end face view taken along the line $X_1$-$X_1$' of FIG. 27, and FIG. 28(C) is a lateral end face view taken along the line $X_2$-$X_2$' of FIG. 27.

The absorbent article 1c illustrated in FIG. 27 and FIG. 28 basically includes a leak preventer 12b having a bottom surface part extending in the front-rear direction and side parts rising upward on both left and right sides of the bottom surface part; an absorber 14 capable of absorbing a body fluid, the absorber containing super absorbent polymer and placed in an internal space formed by the bottom surface part and the side parts of the leak preventer 12b in at least one layer; and a liquid guide unit 10h placed in a front body part of the internal space, at a position where the flow of discharged urine directly collides therewith, and, when urine is discharged, moving the urine from the position where the urine has collided therewith to other positions.

The absorber 14 contains super absorbent polymer and wood pulp. The top sheet 18h is arranged over the entire surface on the absorber 14. At the rear body part, the feces receiving absorber 14a is arranged above the top sheet 18h. The feces receiving absorber 14a is connected to the inner surface of the leak preventer 12b by adhesive and the like at both left and right ends thereof.

The left and right side parts of the leak preventer 12b have the ends folded outward, and the pair of side edge bands 24 are arranged along the ends.

The upper end surface of the urine/feces separating member 28a having a cross-section of Z-shape is connected to the pair of side edge bands 24 at the central part in the front-rear direction, and the lower end surface of the urine/feces separating member 28a is connected to the front end of the feces receiving absorber 14a. Therefore, the absorbent article 1c has a "two-floor structure" in which the feces absorber 14a is arranged above the leak preventer 12b via the absorber 14 and the top sheet 18h at the rear part thereof to absorb the urine with the absorber 14 on the leak preventer 12b and accommodate the feces on the upper side of the feces absorber 14a.

The leak preventer 12b is raised upward at the front end and the rear end.

Two left and right support members 16r are provided between the front end of the leak preventer 12b and the position slightly behind the urine/feces separating member 28a on the top sheet 18h, and the liquid guide unit 10h is arranged on the two support members 16r to bridge across them.

The waist band 32b is connected to both left and right sides on the rear side of the leak preventer 12b, and the connecting part 34a for replaceably connecting to the lower side of the front part of the bottom surface part of the leak preventer 12b is connected to the left and right ends of the waist band 32b.

Figure 29:
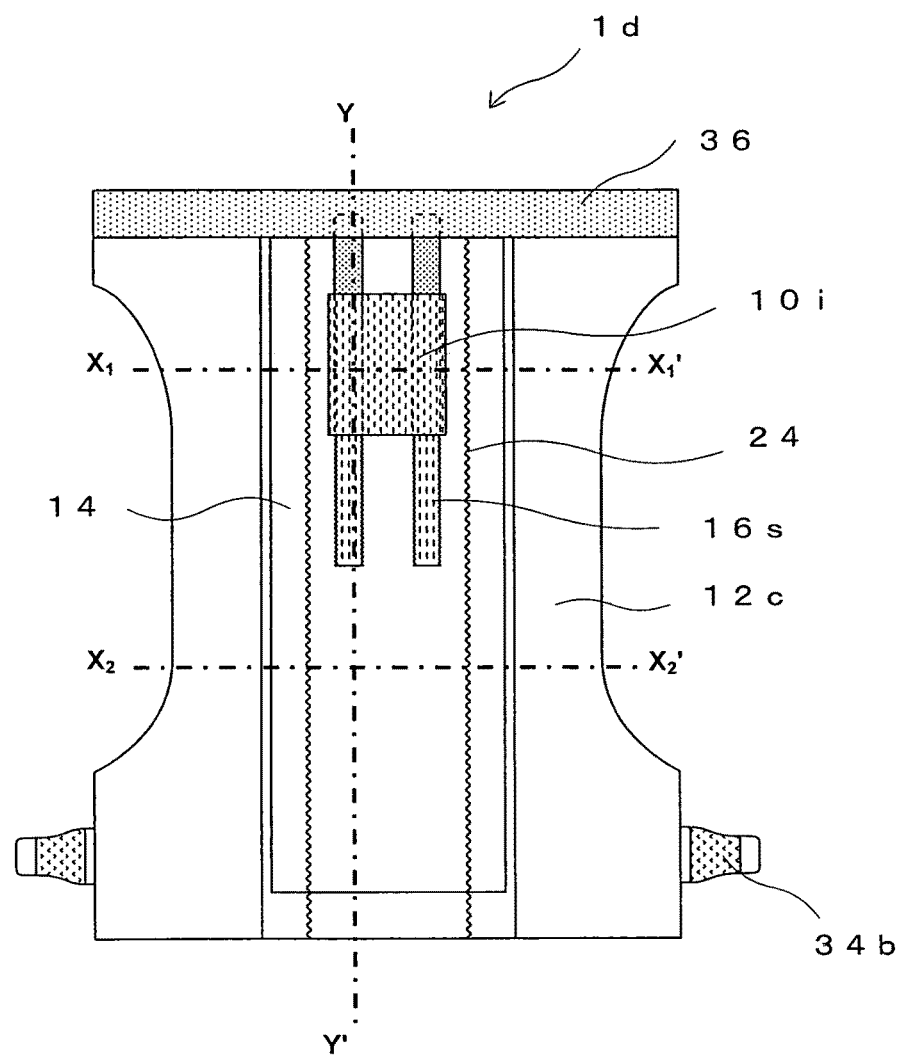
FIG. 29 is a schematic view illustrating further another example of the absorbent article of the present invention.
Figure 30:
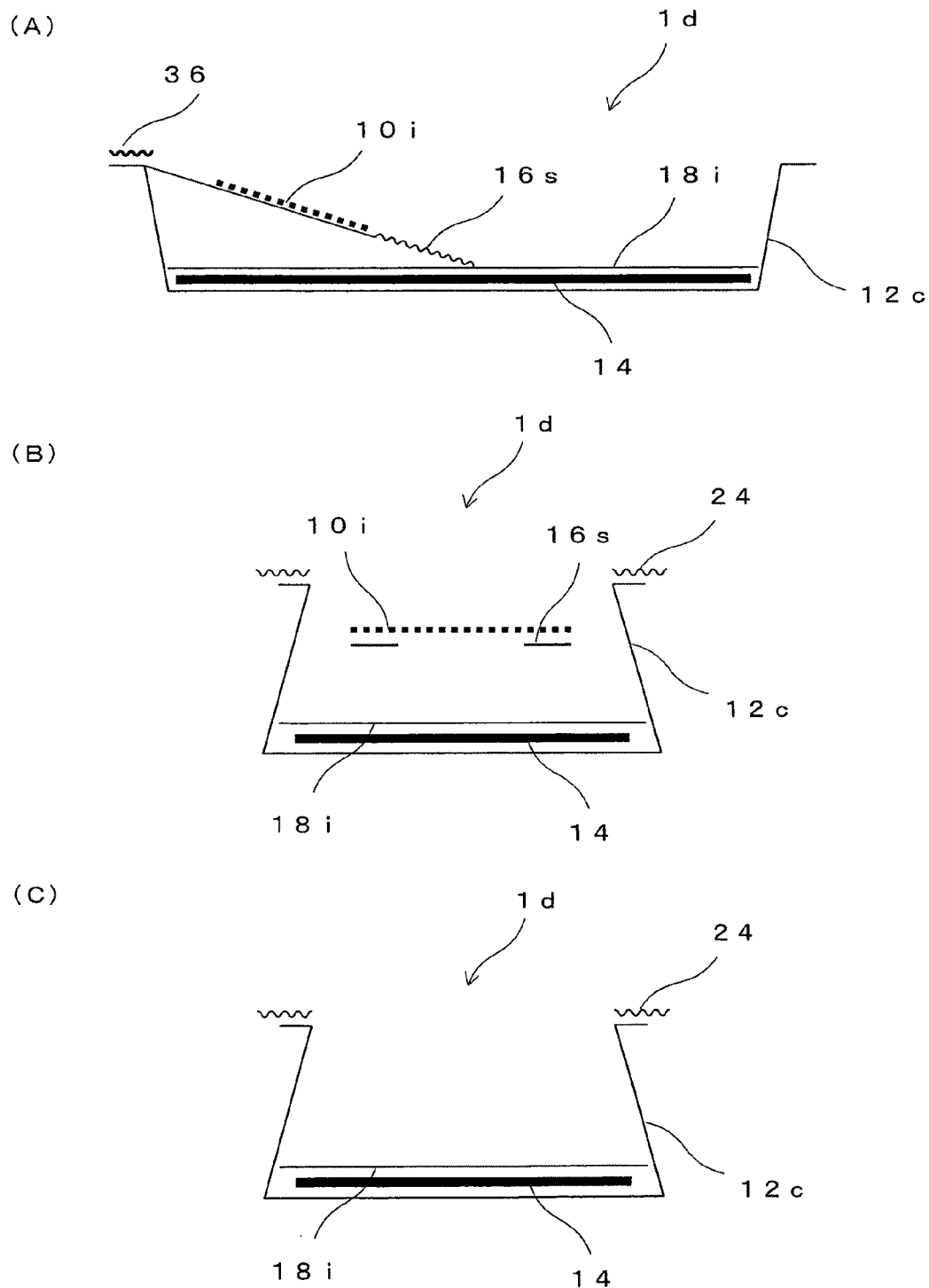
FIG. 30 are schematic views illustrating further another example of the absorbent article of the present invention.

FIG. 29 and FIG. 30 are schematic views illustrating further another example of the absorbent article of the present invention. FIG. 29 is a plan view, FIG. 30(A) is a longitudinal end face view taken along the line Y-Y' of FIG. 29, FIG. 30(B) is a lateral end face view taken along the line $X_1$-$X_1$' of FIG. 29, and FIG. 30(C) is a lateral end face view taken along the line $X_2$-$X_2$' of FIG. 29.

The absorbent article 1d illustrated in FIG. 29 and FIG. 30 basically includes a leak preventer 12c having a bottom surface part extending in the front-rear direction and side parts rising upward on both left and right sides of the bottom surface part; the absorber 14 placed in an internal space formed by the bottom surface part and the side parts of the leak preventer 12c; and a liquid guide unit 10i placed in a front body part of the internal space, at a position where the flow of discharged urine directly collides therewith, and, when urine is discharged, moving the urine from the position where the urine has collided therewith to other positions.

The absorber 14 is an absorber containing super absorbent polymer and wood pulp and wrapped with a tissue paper, for absorbing body fluid. The top sheet 18i is arranged over the entire surface on the absorber 14. Both left and right sides of the leak preventer 12c are raised, and the pair of side edge bands 24 are provided along the ends.

The waist barrier sheet 36 is connected to the front end of the leak preventer 12c, thereby forming a pocket for preventing urine leakage from the front end of the leak preventer 12c. One support member 16s is arranged each on the left and the right at between the waist barrier sheet 36 and substantially the center of the top sheet 18i, and the liquid guide unit 10i is arranged on the upper side of the two support members 16s so as to bridge across them. The support members 16s are non-stretchable in the front side of the liquid guide unit 10i and stretchable in the rear side.

The connecting part 34b for replaceably connecting to the lower side of the front part of the bottom surface part of the leak preventer 12c is connected to both left and right sides of the rear side of the leak preventer 12c.

Figure 31:
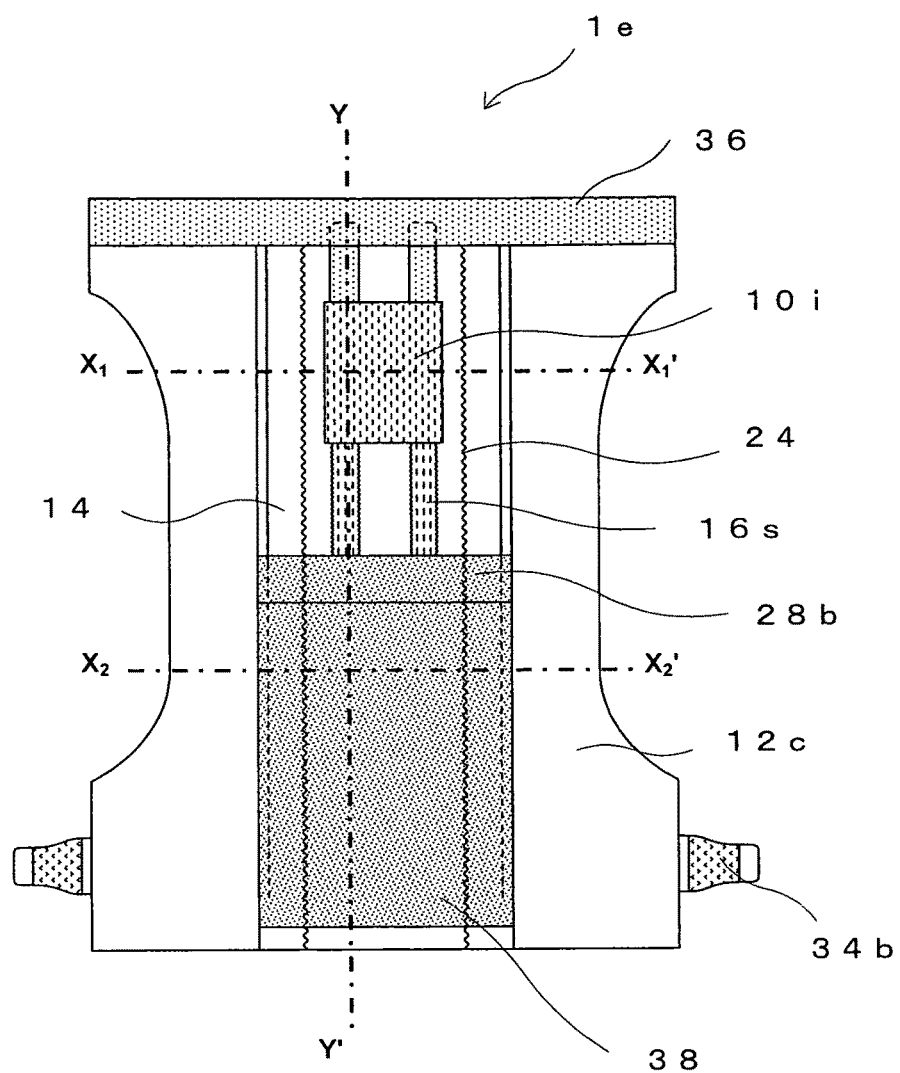
FIG. 31 is a schematic view illustrating further another example of the absorbent article of the present invention.
Figure 32:
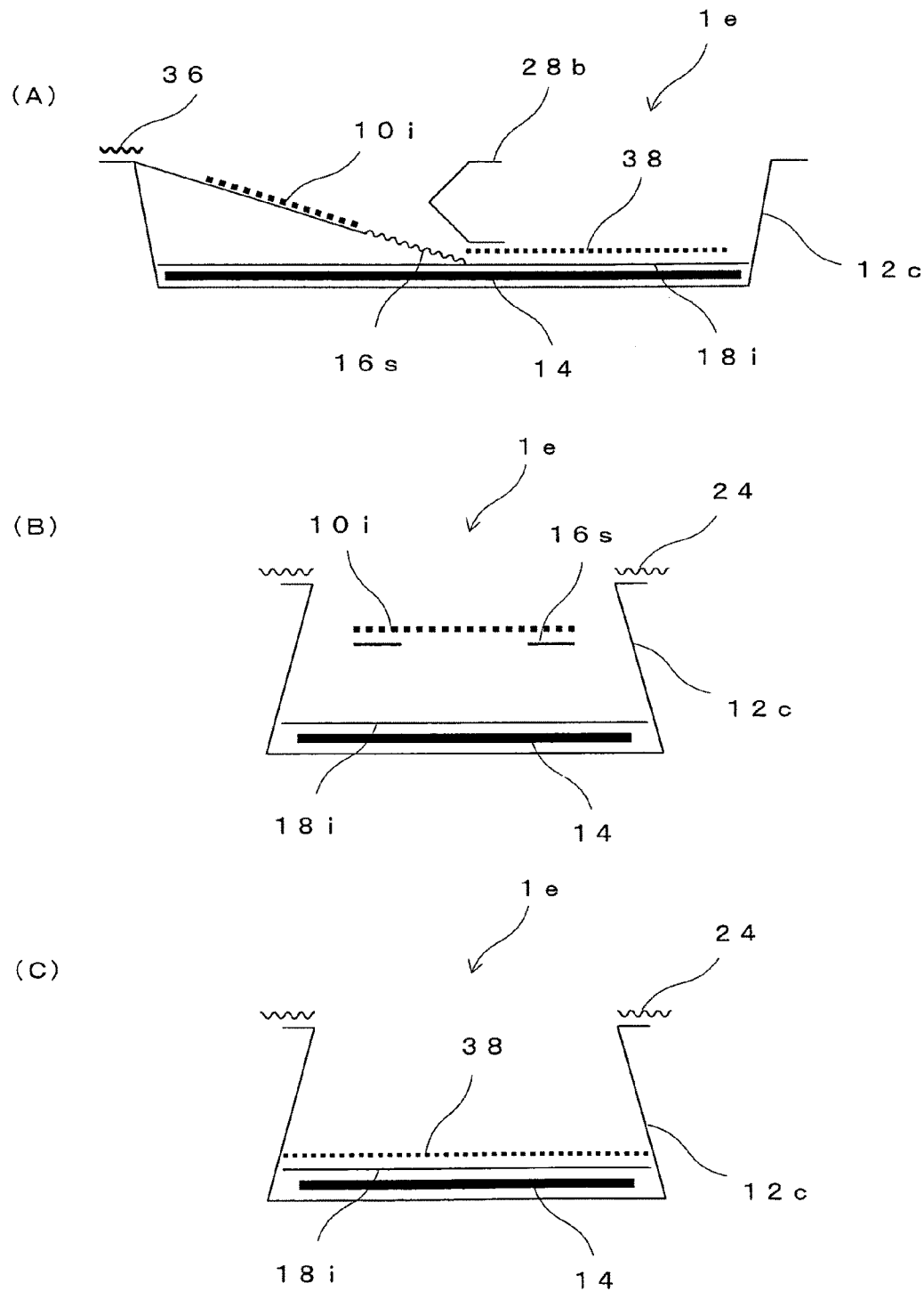
FIG. 32 are schematics views illustrating further another example of the absorbent article of the present invention.

FIG. 31 and FIG. 32 are schematic views illustrating further another example of the absorbent article of the present invention. FIG. 31 is a plan view, FIG. 32(A) is a longitudinal end face view taken along the line Y-Y' of FIG. 31, FIG. 32(B) is a lateral end face view taken along the line $X_1$-$X_1$' of FIG. 31, and FIG. 32(C) is a lateral end face view taken along the line $X_2$-$X_2$' of FIG. 31.

The absorbent article 1e illustrated in FIG. 31 and FIG. 32 is basically the same as the absorbent article 1d illustrated in FIG. 29 and FIG. 30, but at the rear body part, the feces receiving sheet 38 made of hydrophobic SMS nonwoven fabric (e.g., weight 15 g/m²) is provided on the top sheet 18i, and both left and right ends of the feces receiving sheet 38 and the inner surface of the leak preventer 12c are partially connected by adhesive and the like so as to leave a non-connected part. Since the non-connected part remains, if loose feces having an extremely high fluidity such as watery feces is discharged, the loose feces moves from both left and right sides of the feces receiving sheet 38 through the non-connection part to the absorber 14 beneath the feces receiving sheet and absorbed thereat.

One end of the urine/feces separating member 28b having a cross-section of C-shape is connected to the central part in the front-rear direction of the pair of side edge bands 24, and the other end of the urine/feces separating member 28b is connected to the front end of the feces receiving sheet 38. Therefore, the absorbent article 1e has a "two-floor structure" in which the feces receiving sheet 38 is arranged above the leak preventer 12c via the absorber 14 and the top sheet 18i at the rear part thereof to absorb the urine with the absorber 14 on the leak preventer 12c and accommodate the feces on the upper side of the feces receiving sheet 38.

Figure 33:
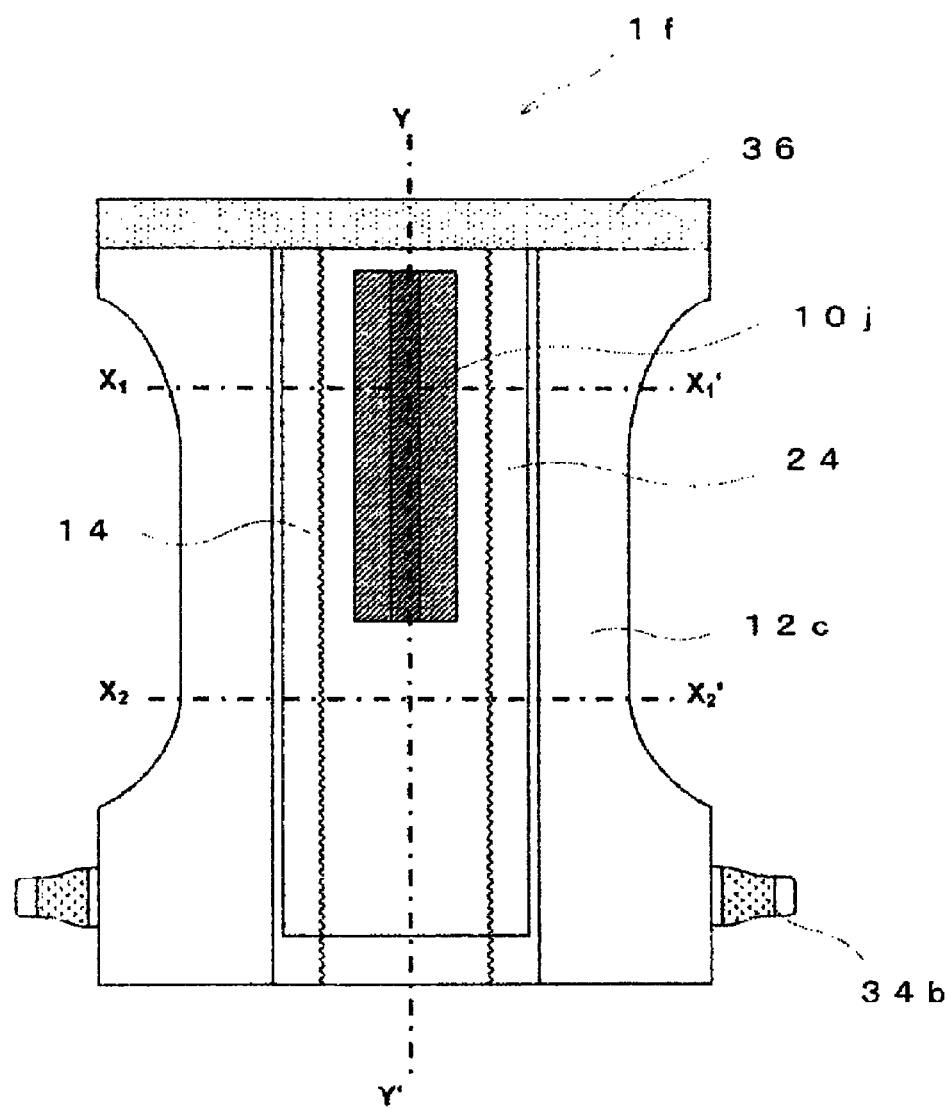
FIG. 33 is a schematic view illustrating further another example of the absorbent article of the present invention.
Figure 34:
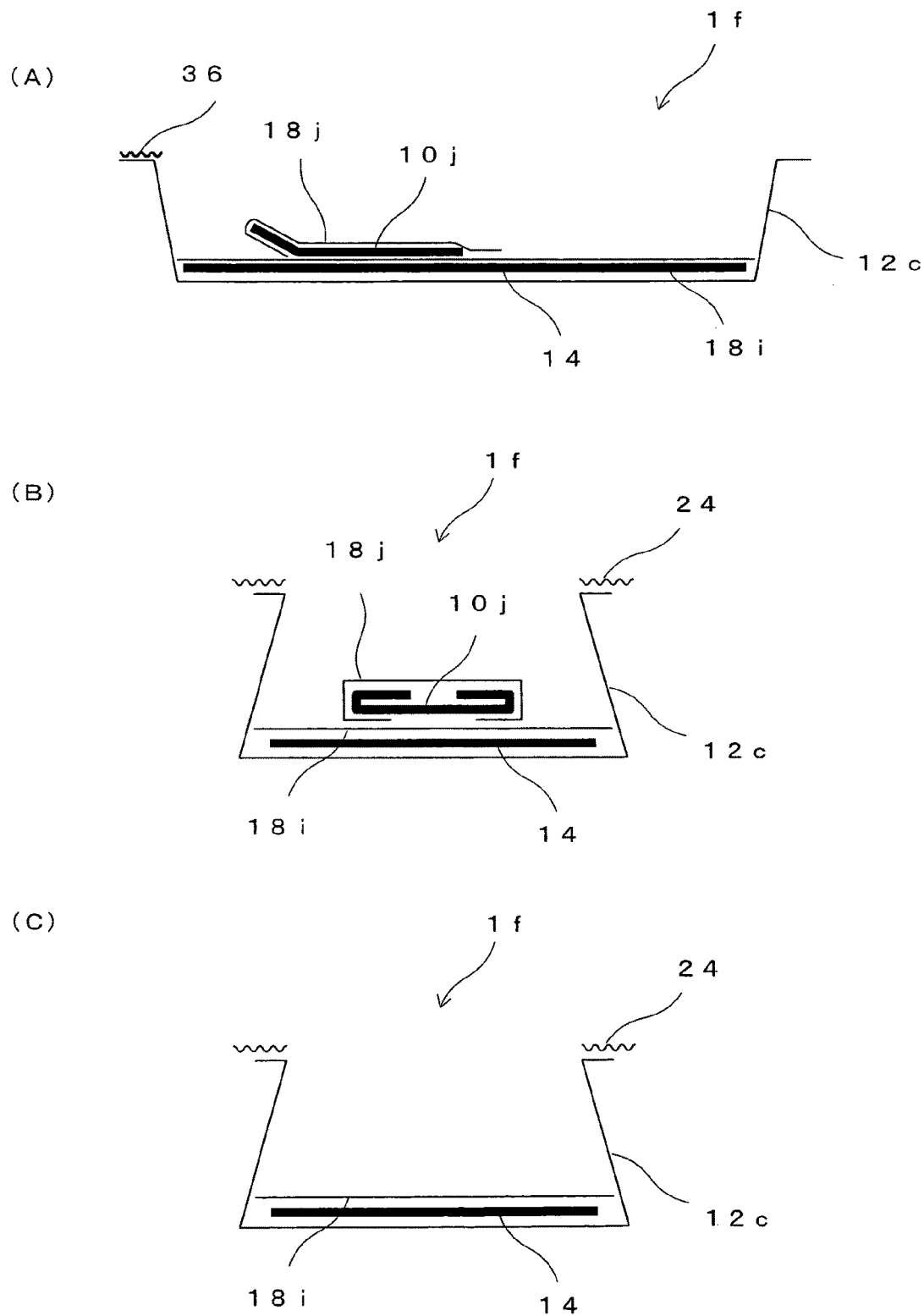
FIG. 34 are schematic views illustrating further another example of the absorbent article of the present invention.

FIG. 33 and FIG. 34 are schematic views illustrating further another example of the absorbent article of the present invention. FIG. 33 is a plan view, FIG. 34(A) is a longitudinal end face view taken along the line Y-Y' of FIG. 33, FIG. 34(B) is a lateral end face view taken along the line $X_1$-$X_1$' of FIG. 33, and FIG. 34(C) is a lateral end face view taken along the line $X_2$-$X_2$' of FIG. 33.

The absorbent article 1f illustrated in FIG. 33 and FIG. 34 basically includes a leak preventer 12c having a bottom surface part extending in the front-rear direction and side parts rising upward on both left and right sides of the bottom surface part; the absorber 14 placed in an internal space formed by the bottom surface part and the side parts of the leak preventer 12c; and a liquid guide unit 10j placed in a front body part of the internal space, at a position where the flow of discharged urine directly collides therewith, and, when urine is discharged, moving the urine from the position where the urine has collided therewith to other positions.

The absorber 14 is an absorber containing super absorbent polymer and wood pulp and wrapped with a tissue paper, for absorbing body fluid. The top sheet 18i is arranged over the entire surface on the absorber 14. Both left and right sides of the leak preventer 12c are raised, and the pair of side edge bands 24 are provided along the ends thereof.

The waist barrier sheet 36 is connected to the front end of the leak preventer 12c, thereby forming a pocket for preventing urine leakage from the front end of the leak preventer 12c. A substantially tube-shaped liquid guide unit 10j is arranged between the waist barrier sheet 36 and substantially the center of the top sheet 18i, and the liquid guide unit 10i is arranged on the central part in the right and left direction.

The substantially tube-shaped liquid guide unit 10j is formed by folding upward both left and right ends of a rectangular super absorbent sheet having a width of about 50 mm (e.g., MegaThin (registered trademark) manufactured by Japan Absorbent Technology Institute)) to have a C-shaped cross-section (see FIG. 34(B)), and then being entirely wrapped with the top sheet 18j. The liquid guide unit 10j has a thickness of about 3 to 5 mm before absorbing urine, which expands to about 30 to 50 mm after absorbing urine, and thus the proximate state with the meatus urinarius of the wearer can be constantly maintained. As such a liquid guide unit, it is possible to use a tube-shaped absorber described in JP 10-314217 A proposed by the inventors of the present invention.

The liquid guide unit 10j has the vicinity of the front end raised upward slightly without being connected to the top sheet 18i, and the other portions connected to the top sheet 18i (see FIG. 34(A)).

The connecting part 34b for replaceably connecting to the lower side of the front part of the bottom surface part of the leak preventer 12c is connected to both left and right sides of the rear side of the leak preventer 12c.

Figure 35:
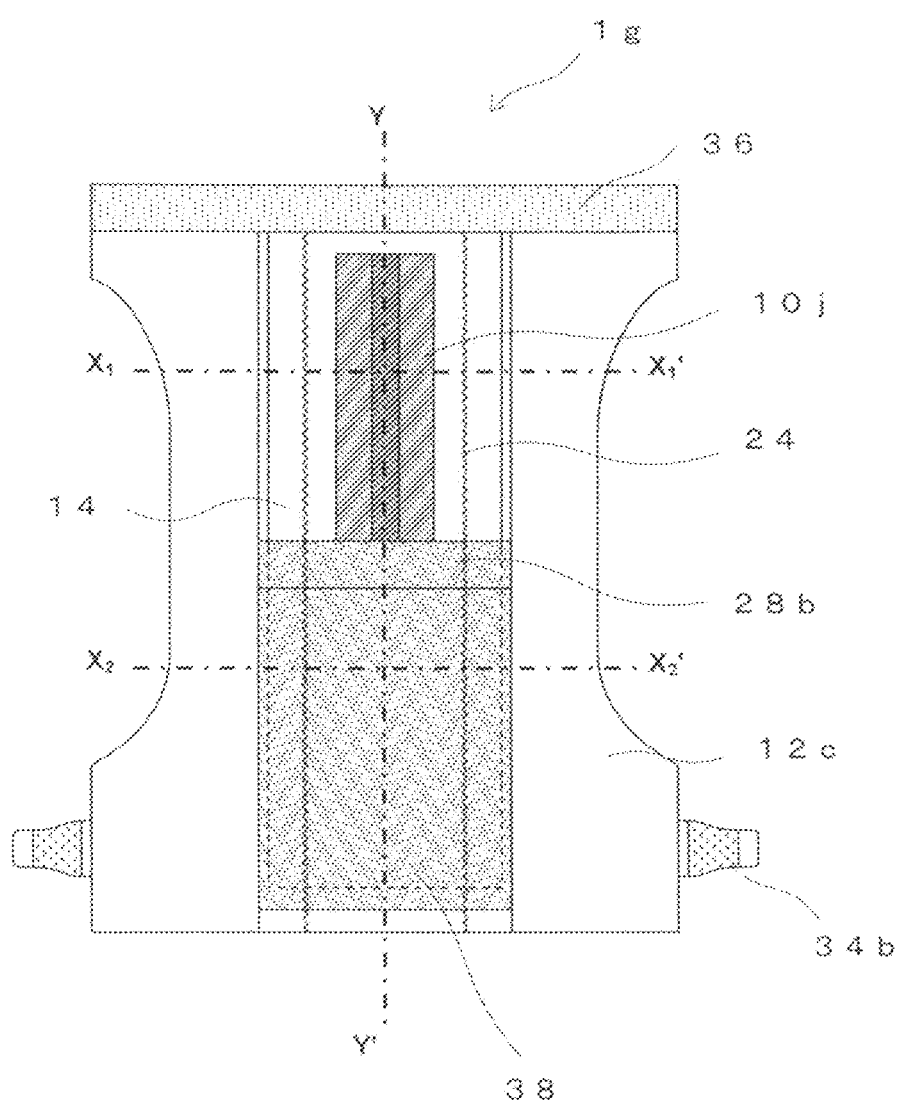
FIG. 35 is a schematic view illustrating further another example of the absorbent article of the present invention.
Figure 36:
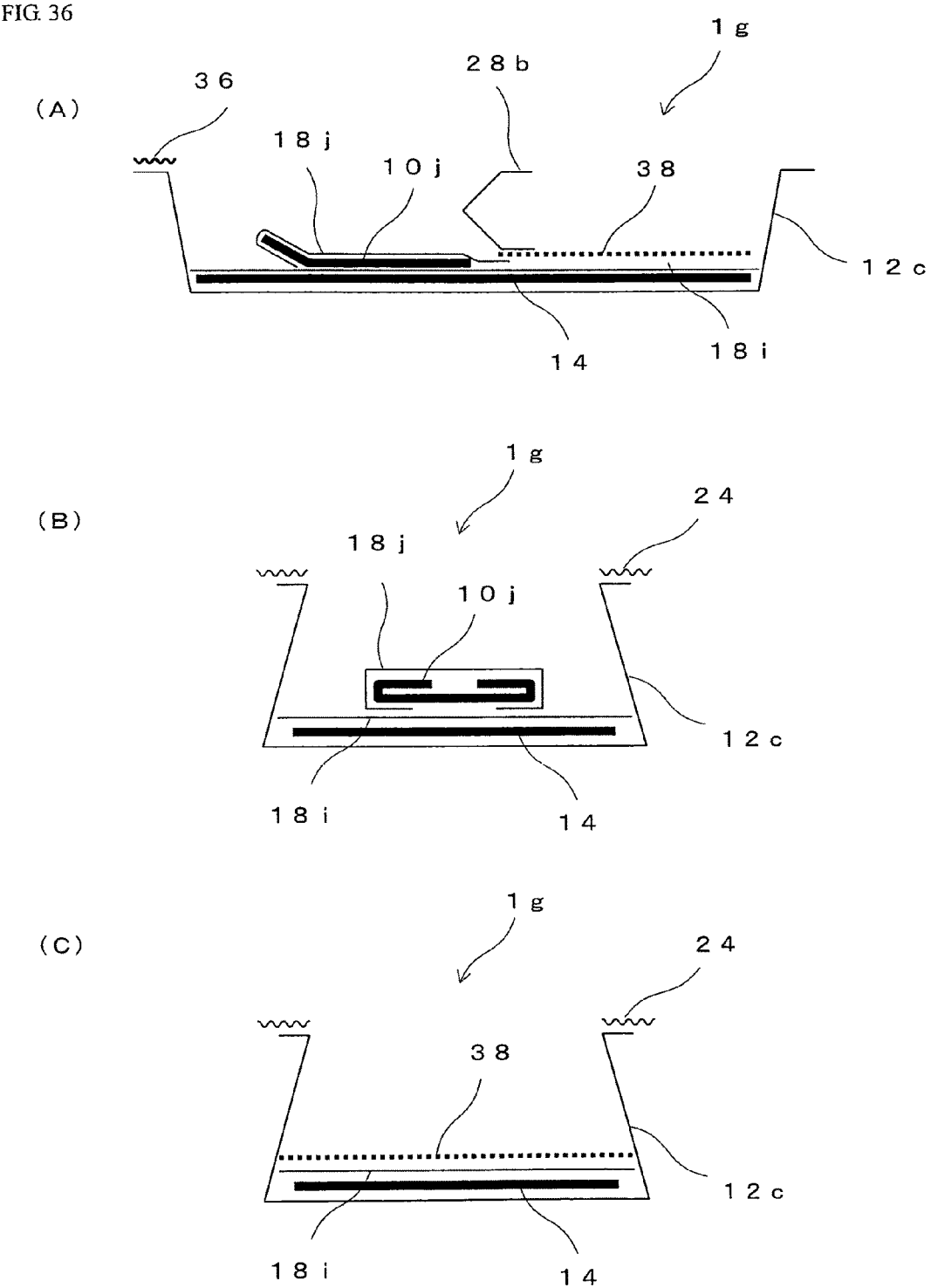
FIG. 36 are schematic views illustrating further another example of the absorbent article of the present invention.

FIG. 35 and FIG. 36 are schematic views illustrating further another example of the absorbent article of the present invention. FIG. 35 is a plan view, FIG. 36(A) is a longitudinal end face view taken along the line Y-Y' of FIG. 35, FIG. 36(B) is a lateral end face view taken along the line $X_1$-$X_1$' of FIG. 35, and FIG. 36(C) is a lateral end face view taken along the line $X_2$-$X_2$' of FIG. 35.

The absorbent article 1g illustrated in FIG. 35 and FIG. 36 is basically the same as the absorbent article if illustrated in FIG. 33 and FIG. 34, but at the rear body part, the feces receiving sheet 38 made of hydrophobic SMS nonwoven fabric (e.g., weight 15 g/m²) is provided on the top sheet 18i, and both left and right ends of the feces receiving sheet 38 and the inner surface of the leak preventer 12c are partially connected by adhesive and the like so as to leave a non-connected part. Since the non-connected part remains, if loose feces having an extremely high fluidity such as watery feces is discharged, the loose feces moves from both left and right sides of the feces receiving sheet 38 through the non-connection part to the absorber 14 under the feces receiving sheet 38 thereof and absorbed thereat.

Further, one end of the urine/feces separating member 28b having a cross-section of C-shape is connected to the central part in the front-rear direction of the pair of side edge bands 24, and the other end of the urine/feces separating member 28b is connected to the front end of the feces receiving sheet 38. Therefore, the absorbent article 1g has a "two-floor structure" in which the feces receiving sheet 38 is arranged above the leak preventer 12c via the absorber 14 and the top sheet 18i at the rear part thereof to absorb the urine with the absorber 14 on the leak preventer 12c and accommodate the feces on the upper side of the feces receiving sheet 38.

Figure 37:
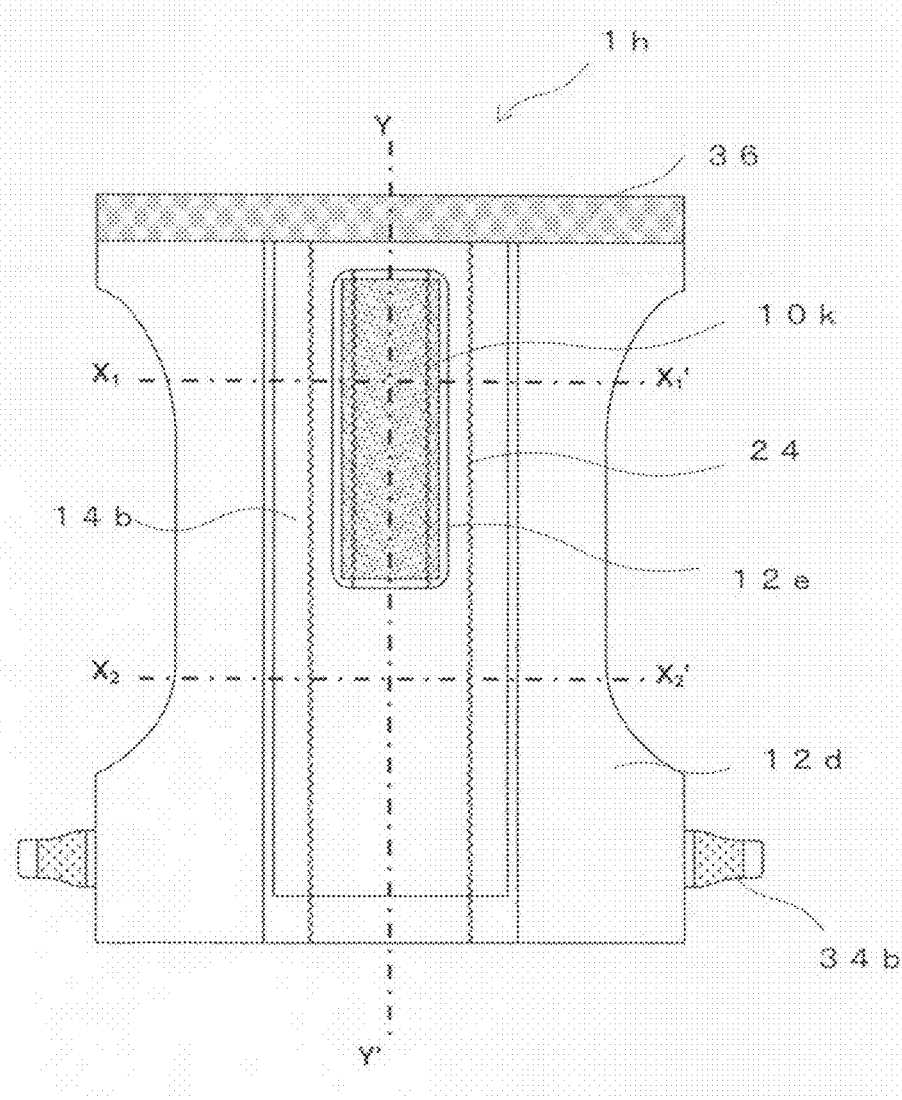
FIG. 37 is a schematic view illustrating further another example of the absorbent article of the present invention.

FIG. 37 and FIG. 38 are schematic views illustrating further another example of the absorbent article of the present invention. FIG. 37 is a plan view, FIG. 38(A) is a longitudinal end face view taken along the line Y-Y' of FIG. 37, FIG. 38(B) is a lateral end face view taken along the line $X_1$-$X_1$' of FIG. 37, and FIG. 38(C) is a lateral end face view taken along the line $X_2$-$X_2$' of FIG. 37.

The absorbent article 1h illustrated in FIG. 37 and FIG. 38 basically includes a leak preventer 12d having a bottom surface part extending in the front-rear direction and side parts rising upward on both left and right sides of the bottom surface part; the absorber 14b placed in an internal space formed by the bottom surface part and the side parts of the leak preventer 12d; and a liquid guide unit 10k placed in a front body part of the internal space, at a position where the flow of discharged urine directly collides therewith, and, when urine is discharged, moving the urine from the position with which the urine has collided to other positions.

The absorber 14b is an absorber containing super absorbent polymer and wood pulp and wrapped with a tissue paper, for absorbing body fluid. The top sheet 18k is arranged over the entire surface on the absorber 14b. Both left and right sides of the leak preventer 12d are raised, and the pair of side edge bands 24 are provided along the ends thereof.

The waist barrier sheet 36 is connected to the front end of the leak preventer 12d, thereby forming a pocket for preventing urine leakage from the front end of the leak preventer 12d.

In the front, body part, a V-shaped recessed portion is formed at the middle in the left and right direction of the leak preventer 12d, and the absorber 14b and the top sheet 18k respectively have a shape that lies along the shape of the leak preventer 12d.

The liquid guide unit 10k and the leak preventer 12e under the liquid guide unit 10k having a shape similar to a sanitary napkin or a urinary pad are provided on the V-shaped recessed portion of the leak preventer 12d via the absorber 14b and the top sheet 18k so as to cover the recessed portion. The leak preventer 12e is connected to the top sheet 18k with an adhesive (shaded part of FIG. 38(B)) at both left and right ends of the lower surface thereof. The front end of the leak preventer 12e is raised without being connected to the top sheet 18k, and is arranged to be proximate to the meatus urinarius.

The liquid guide unit 10k is a rectangular laminated body of the film having openings and the super absorbent sheet (e.g., MegaThin (registered trademark) manufactured by Japan Absorbent Technology Institute)) thereunder, and the bottom surface and both left and right sides thereof are covered by the leak preventer 12e. The leak preventer 12e is raised at both left and right sides to form an expandable gather, and thus has a shape similar to a sanitary napkin or a urine pad.

When urine is discharged to the liquid guide unit 10k, a part of the urine is absorbed by the super absorbent sheet of the liquid guide unit 10k, but the majority of the urine moves to the front and the rear. In this case, the urine does not move from the left and right sides of the liquid guide unit 10k as the leak preventer 12e is raised is raised at the sides.

The absorbent article 1h does not have a feces receiving sheet but can accommodate the feces that flowed out from the rear body part at the recessed portion of the front body part, and thus the possibility the feces contacts the skin of the wearer at the front body part is small.

The connecting part 34b for replaceably connecting to the lower side of the front portion of the bottom surface part of the leak preventer 12d is connected to the left and right sides on the rear side of the leak preventer 12d.

EXAMPLE

Hereinafter, the present invention is specifically described by illustrating examples. However, it should be noted that the present invention is not limited thereto.

1. Fabrication of Absorbent Article

Example 1

Figure 39:
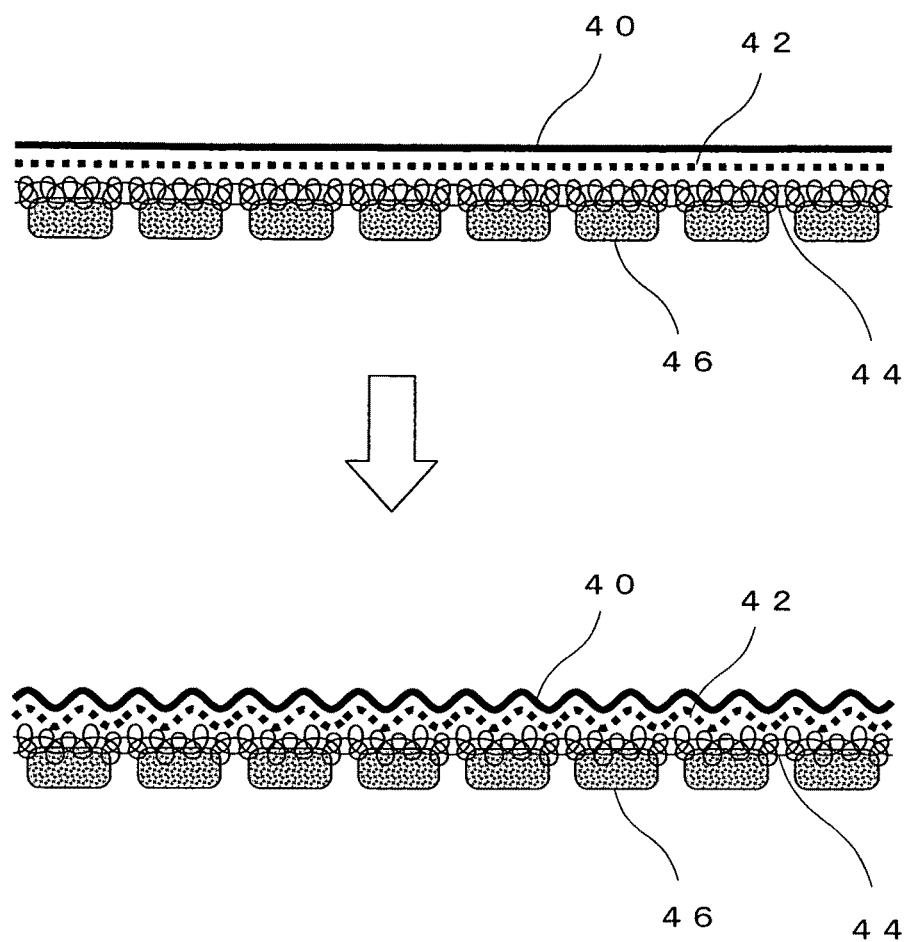
FIG. 39 is a schematic lateral end face view of a thin super absorbent sheet used in the feces receiving absorber of the absorbent article of Example 1.

The absorbent article corresponding to the absorbent article 1c illustrated in FIGS. 27 and 28 was fabricated in the following manner by hand.
(1) Overall Structure
    The fabricated absorbent article is a urine/feces separation type diaper having a urine receiving part in the front body part and a feces receiving part in the rear body part, and a urine/feces separating member at the central part.
    The front body part includes the liquid guide unit, the top sheet, the absorber (lower layer absorber), and the leak preventer (back sheet) in order from the body side of the wearer. The liquid guide unit is arranged at a position where the flow of discharged urine directly collides therewith in the front body part (urine receiving part).
    The rear body part has a feces receiving absorber (upper layer absorber), an absorber (lower layer absorber), and a leak preventer (back sheet) in order from the body side of the wearer. At the rear body part, the absorber has a two-layer structure, and the upper layer absorber is used to receive the feces and absorb the urine, and the lower layer absorber is placed from the front body part to the rear body part to be used to absorb urine.
    The urine/feces separating member arranged at the central part has the lower end connected to the front end of the feces receiving absorber (upper layer absorber) arranged in the rear body part.
    The size was about large size of a diaper for children.
(2) Liquid Guide Unit
    The liquid guide unit was formed of an PE film having openings (X-27373 film, manufactured by Tredegar Corporation) subjected to surface hydrophilic processing. The film having openings had a rectangular shape having the length in the front-rear direction of 80 mm, and the length in the left and right direction of 70 mm.
    The liquid guide unit was arranged to bridge over the upper sides of the two left and right support members. The support members had a structure in which the top and the bottom of a urethane filament were laminated with two sheets of SB nonwoven fabric, and had stretchability. The support members had the front ends connected to the front end portion of the leak preventer (back sheet), and the rear ends connected at the position slightly rear from the central part of the top sheet.
    The liquid guide unit was worn so as to lightly contact the vicinity of the meatus urinarius of the wearer.
(3) Absorber
    (a) Absorber (Lower Layer Absorber)
    A mixture of 10 g of pulp and 5 g of SAP was wrapped with tissue paper to form a sheet-form absorber. The absorber had a rectangular shape having the length in the front-rear direction of 360 mm and the length in the left and right direction of 80 mm.
    The designed absorbent capacity was 320 g of water absorbing capacity and 180 g of water retention capacity.
    The absorber was arranged from the front body part to the rear body part, and served as the main portion for absorbing urine.
    (b) Feces Receiving Absorber (Upper Layer Absorber)
    The thin super absorbent sheet (MegaThin (registered trademark) manufactured by Japan Absorbent Technology Institute)) was used for the feces receiving absorber. FIG. 39 is a schematic lateral end face view of the thin super absorbent sheet used for the feces receiving absorber of the absorbent article of Example 1. The thin super absorbent sheet was a composite sheet (thickness of about 1.1 mm) having a three-layer configuration of the hydrophobic SMS nonwoven fabric 40 (weight 13 g/m$^2$), the tissue paper 42 (weight 15 g/m$^2$), and the polyester web 44 (weight 20 g/m$^2$) that carries the SAP layer 46 (weight 150 g/m$^2$) on the lower surface from the body side of the wearer (see upper figure of FIG. 39). The thin super absorbent sheet was entirely given flexibility and was subjected to microscopic colgate processing with paper climper (manufactured by FISKARS BRANDS, INC.) to provide concave and convex shape on the surface thereof (see lower figure of FIG. 39). The thin super absorbent sheet had a rectangular shape having the length in the front-rear direction of 160 mm, and the length in the left and right direction of 60 mm.
    The SAP layer carried at the polyester web was provided in line pattern with a width of about 10 mm and at an interval of about 5 mm.
    The thin super absorbent sheet was arranged such that the hydrophobic SMS nonwoven fabric faces the body side of the wearer and the surface of the hydrophobic SMS nonwoven fabric receives the feces.

The thin super absorbent sheet was an SAP layer and was provided to absorb the urine that moved to the rear body part.

The thin super absorbent sheet was arranged such that the SAP layer of line pattern is in the front-rear direction.

The designed absorbent capacity was 120 g of water absorbing capacity and 72 g of water retention capacity.

(4) Urine/Feces Separating Member

The urine/feces separating member was formed by folding the laminated article (rectangular shape having the length in the front-rear direction of 60 mm, and the length in the left and right direction of 80 mm) of the SMS nonwoven fabric (manufactured by Toray Saehan Inc., weight 13 g/m$^2$) and the PE (LLDPE) film (manufactured by Mitsui Chemicals Inc.) into Z-shape (length in the front-rear direction of the upper side part, the intermediate part, and the lower side part of the Z-shape was 20 mm each).

The lower surface of the lower side part of the urine/feces separating member was connected to the hydrophobic SMS nonwoven fabric of the feces receiving absorber (upper layer absorber) by the hot melt adhesive.

The left and right ends of the upper side part of the urine/feces separating member were connected to the side edge bands. Thus, the state in which the upper surface of the upper side part of the urine/feces separating member contacts the perineum of the wearer was constantly maintained during wearing.

Due to the Z-shaped folded structure, the space in the vertical direction of the feces receiving part can be ensured while maintaining the state in which the upper surface of the upper side part of the urine/feces separating member contacts the perineum during attaching of the absorbent article and after defecating. The capacity of the feces receiving part was about 200 mL in a state without pressurization, and about 80 mL under pressurization (20 lb/cm$^2$).

The urine/feces separating member was arranged so as to contact the perineum (between sexual organ and anus of the wearer).

(5) Side Edge Bands

The side edge bands were provided from the front end part to the rear end part along the edge of the left and right side parts of the leak preventer, and had stretchability.

The side edge bands comprise plural urethane filaments (manufactured by DU-PONT TORAY CO., LTD., 620tex) arranged in parallel, and sandwiched in the two sheets of SB nonwoven fabric (manufactured by Toray Saehan Inc.).

The side edge bands had a length of 360 mm (in time of contraction), and a width of 20 mm.

The side edge bands had stretchability in the front-rear direction. The stretchability was 200%.

(6) Others

The waist bands and the connecting parts were formed by cutting out the waist portion of a width of 80 mm from a commercially available diaper for children (Moony man Big size, manufactured by Unicharm Corporation), and connecting them to the leak preventer.

Comparative Example 1

The absorbent article was fabricated through a method similar to that of Example 1 other than that the liquid guide unit and the support member were not provided.

2. Evaluation of Absorbent Article (1) Measurement of Water Absorbing Capacity and Swelling Ratio of Absorbent Article The water absorbing capacity and the water-retention amount were measured according to the standard of JIS K7223-1996 "Testing method for water-absorption capacity of super absorbent polymers" with respect to the absorbent article obtained in Example 1.

The water absorbing capacity was measured by immersing the absorbent article in a normal saline solution for 20 minutes in a bat to absorb water.

The water retention amount was measured by removing water through centrifugal separation for ten minutes at 1000 G after measuring the water-absorbing capacity.

The thicknesses of the front body part (one absorber layer) and the rear body part (two absorber layers) were measured before and after water absorption as being respectively placed at the middle in the left and right direction of the absorbent article, and the value after water absorption was divided by the value before water absorption to calculate the swelling ratio.

The measurement result was 440 g of water absorbing capacity and 252 g of water-retention amount.

The thickness of the front body part was 3.0 mm before water absorption and 11.0 mm after water absorption, and the swelling ratio was 3.6 times. The thickness of the rear body part was 4.1 mm before water absorption and 24.0 mm after water absorption, and the swelling ratio was 5.9 times.

Only the absorber using the mixture of pulp and SAP of the related art was arranged at the front body part, and the two-layer absorbers having the absorber and the thin super absorbent sheet was arranged at the rear body part, and thus a large difference was seen between the front body part and the rear body part in the swelling ratio.

(2) Wearing Test

A wearing test was conducted on the absorbent article fabricated in the example.

Specifically, healthy babies (total of six babies including three boys and three girls) having normal urinating function and defecating function were made to wear five sheets of absorbent articles (total of thirty sheets), and they were allowed to carry out urination and defecation. The average wearing time, the number of sheets they urinated on, average absorbing capacity of urine, number of sheets from which urine was leaked, number of sheets they defecated on, type of feces, and number of sheets which leaked feces was examined. The results are illustrated in Table 1.

Among the thirty sheets, those in which the body position was relatively known were decomposed, and the usage state (urine diffusion state) of the absorber (lower layer absorber) and the feces receiving absorber (upper layer absorber) were analyzed for boys and girls for each body position.

The usage state of the absorber (lower layer absorber) was examined just as is. The usage state of the feces receiving absorber (upper layer absorber) was examined by equally dividing into three portions of the front body part, the central part, and the rear body part. The usage state was visually evaluated by measuring the proportion of the portion where the urine was absorbed of the total amount of the absorber or the feces receiving absorber. The results are illustrated in Table 2.

TABLE 1

|  | Example 1 | Comparative Example 1 |
|---|---|---|
| Average wearing time (time) | 4 | 4 |
| Number of urinated sheets (sheet) | 30 | 30 |
| Average absorbing capacity (g) | 200 | 200 |
| Number of urine leaked sheets (sheet) | 1*[1] | 4*[2] |
| Number of defecated sheets (sheet) | 6 | 4 |
| Type of feces (sheet)  Normal feces | 5 | 3 |
| Loose feces | 1 | 1 |
| Number of feces leaked sheets (sheet) | 0 | 0 |

*[1] ooze from the crotch part at sitting position: 1 sheet
*[2] leak from the sides: 2 sheets, sitting position: 2 sheets

TABLE 2

| | | | Usage state of absorber (%) | | | |
|---|---|---|---|---|---|---|
| | | | | Feces receiving absorber (upper layer absorber) | | |
| | | Main body position | Absorber (lower layer absorber) | Front body part | central part | rear body part |
| Example 1 | Boy | Standing position, sitting position | 50 | 60 | 100 | 80 |
| | | Face-up position | 100 | 20 | 90 | 100 |
| | | Face-down position | 50 | 100 | 70 | 50 |
| | | Side-lying position | 80 | 60 | 80 | 80 |
| | Girl | Standing position, sitting position | 80 | 50 | 100 | 100 |
| | | Face-up position | 100 | 10 | 90 | 100 |
| | | Face-down position | 50 | 60 | 100 | 60 |
| | | Side-lying position | 80 | 60 | 80 | 80 |
| Comparative Example 1 | Boy | Standing position, sitting position | 30 | 90 | 100 | 40 |
| | | Face-up position | 80 | 50 | 100 | 80 |
| | | Face-down position | 10 | 100 | 90 | 10 |
| | | Side-lying position | 50 | 80 | 80 | 50 |
| | Girl | Standing position, sitting position | 70 | 60 | 100 | 90 |
| | | Face-up position | 80 | 20 | 90 | 80 |
| | | Face-down position | 20 | 90 | 90 | 20 |
| | | Side-lying position | 40 | 60 | 60 | 60 |

As to urine leakage, ooze did not occur at any body positions other than that it was observed in one sheet at the sitting position for the absorbent article of Example 1, but urine leakage occurred depending on the body position for the absorbent article of Comparative Example 1. The leakage conceivably results from the following. In Comparative Example 1, the urine was not widely distributed in the absorbent article, and the used portion of the absorber concentrated at one area, thereby exceeding the absorbing ability of the absorber at the area, and thus the urine is assumed to have leaked out from the vicinity of the area to the outside of the absorbent article.

Regarding the difference in the usage state of the absorber between boys and girls, the usage state was similar in the absorbent article of Example 1. This is assumed to be because, although the shape of the local part is different, the direction in which the urine moves after colliding to the liquid guide unit is the same between boys and girls. In the absorbent article of Comparative Example 1, on the other hand, the rear body part was barely used in boys and girls, and the use concentrated in the front body part for boys and the central part for girls. Therefore, it can be seen that the difference in the used area of the absorber of boys and girls is eliminated by arranging the liquid guide unit. It can also be seen that the utilization efficiency of the absorber was enhanced.

Regarding the urine/feces separation state, in the absorbent article of Example 1, substantially the entire amount of urine moved to the absorber and the feces receiving absorber and the urine/feces separating member was barely wet for the boys, whereas, in the case of girls, the urine/feces separating member was wet in a few sheets and a few drops of the urine flowed to the feces receiving part. This is assumed to be because in the case of girls, some urine moved on the body surface of the wearer instead of the liquid guide unit depending on the body position, and such urine flowed towards the urine/feces separating member. Other than such a case, substantially the entire amount of urine moved to the absorber of the rear body part and the feces receiving absorber, similarly to the case of boys. As with the absorbent article of Example 1, how to move the urine to the absorber (how to prevent urine from moving on the body surface of the wearer) becomes a problem to be solved in the absorbent article designed to separate the absorber and the body surface during wear in order to avoid the urine and the feces from contacting the body surface of the wearer, but such problem is resolved as substantially the entire amount moved to the absorber of the rear body part and the feces receiving absorber by the liquid guide unit in the absorbent article of Example 1.

In the absorbent article of Comparative Example 1, some urine even reached the feces receiving part past the urine/feces separating member especially in the face-up position, which phenomenon significantly appeared in girls. As a result, the defecated excretion was a mixture of urine and feces.

In the absorbent article of Example 1, the movement of the urine to the rear body part past the crotch part occurs not only in the face-up position at which the urine relatively easily moves to the rear body part but also in the standing position, the sitting position and the like, and the urine was sufficiently absorbed at the rear body part.

In the absorbent article of Example 1, the surface of the liquid guide unit after use was barely wet, substantially the entire amount of discharged urine moved to the absorber and the feces receiving absorber, and reached the rear ends thereof.

Therefore, it was found that as including the liquid guide unit, the absorbent article of the present invention excels in utilization efficiency of the absorber regardless of whether it is used by a boy or a girl, and is less likely to cause leakage, and excels in urine/feces separating function.

The invention claimed is:

1. An absorbent article including:
a leak preventer including a bottom surface part extending in a front-rear direction, and side parts raised to an upper side at both left and right sides of the bottom surface part;
an absorber containing a super absorbent polymer for absorbing a body fluid placed in an internal space formed by the bottom surface part and the side parts of the leak preventer in at least one layer;
a liquid guide unit, having a top surface and a bottom surface, the top surface being opposite the bottom surface, and the top surface being closest to a wearer, wherein:
the liquid guide unit is placed in a front body part of the internal space, at a position near a meatus urinarius of a wearer when the absorbent article is worn by the wearer and where a flow of discharged urine directly collides with the liquid guide unit,
the liquid guide unit is not directly contacting the absorber; and
the liquid guide unit is configured for moving the urine from the position where the urine has collided with the liquid guide to other positions when urine is discharged, wherein the absorbent article does not include a top sheet;
side edge bands along ends of the side parts of the leak preventer, the side edge bands being directly connected to left and right ends of the liquid guide unit or being connected by a connection member such that the side bands are disposed on a same planar surface as the liquid guide unit or on the top surface of the liquid guide unit; and
a support member for supporting the liquid guide unit from a lower surface of the liquid guide unit to make a space between the liquid guide unit and the absorber, the support member having a front end connected to a front end portion of the leak preventer, and a rear end connected at a position in vicinity of a central part of the absorber in the front-rear direction or a position behind the central part of the absorber in the front-rear direction.

2. The absorbent article according to claim 1, in which the liquid guide unit is in sheet-form.

3. The absorbent article according to claim 2, in which the liquid guide unit has a width of between 10 and 100 mm, length of between 20 and 200 mm, and thickness of between 0.1 and 2 mm.

4. The absorbent article according to claim 2, in which a part of a peripheral edge of the liquid guide unit is not connected to other portions of the absorbent article.

5. The absorbent article according to claim 2, in which the liquid guide unit is formed of a film having openings, the film having numerous openings.

6. The absorbent article according to claim 2, in which at least a part of the liquid guide unit has a cushioning property.

7. The absorbent article according to claim 6, in which the liquid guide unit is formed of a bulky nonwoven fabric.

8. The absorbent article according to claim 2, in which at least a part of the liquid guide unit has stretchability.

9. The absorbent article according to claim 8, in which the liquid guide unit is formed of a stretchable net.

10. The absorbent article according to claim 1, in which the liquid guide unit is formed of a molded foam body having a recessed surface on an upper side.

11. The absorbent article according to claim 1, further including an urine/feces separating member in the vicinity of a central part in the front-rear direction of the leak preventer, the urine/feces separating member allowing a front body part of the internal space to function as an urine receiving part and a rear body part of the internal space to function as a feces receiving part.

12. The absorbent article according to claim 11, in which the urine/feces separating member and the liquid guide unit are connected.

13. The absorbent article according to claim 1, in which at least a part of the side edge bands has stretchability.

14. The absorbent article according to claim 1, in which the connection member for connecting the side edge bands and the left and right ends of the liquid guide unit has stretchability.

15. The absorbent article according to claim 1, wherein the support member is for supporting the liquid guide unit from a lower side.

16. The absorbent article according to claim 15, in which at least a part of the support member has stretchability.

17. The absorbent article according to claim 1, further including waist bands at a front end and a rear end of the leak preventer, the waist bands and the liquid guide unit being connected directly or by a connection member.

18. The absorbent article according to claim 17, in which the connection member for connecting the liquid guide unit and the waist bands has stretchability.

19. The absorbent article according to claim 1, in which the absorber is a super absorbent sheet containing the super absorbent polymer at greater than or equal to 50 wt %.

20. The absorbent article according to claim 2, in which a surface of the liquid guide unit is hydrophilic.

21. The absorbent article according to claim 5, in which the film having openings has liquid permeability.

22. The absorbent article according to claim 7, in which the bulky nonwoven fabric has liquid permeability.

23. The absorbent article according to claim 1, further including waist bands at a front end and a rear end of the leak preventer, at least one of the waist bands and the liquid guide unit being connected directly or by a connection member.

24. The absorbent article according to claim 23, where the at least one of the waist bands is a band at the front end of the leak preventer.

25. An absorbent article including:
a leak preventer including a bottom surface part extending in a front-rear direction, and side parts raised to an upper side at both left and right sides of the bottom surface part;
an absorber containing a super absorbent polymer for absorbing a body fluid placed in an internal space formed by the bottom surface part and the side parts of the leak preventer in at least one layer;
a top sheet on an upper side of the absorber;
a liquid guide unit, unit, having a top surface and a bottom surface, the top surface being opposite the bottom surface, and the top surface being closest to a wearer, wherein:
the liquid guide unit is placed in a front body part of the internal space, at a position near a meatus urinarius of a wearer when the absorbent article is worn by the wearer and where a flow of discharged urine directly collides with the liquid guide unit, the liquid guide unit is not directly contacting the absorber;

the liquid guide unit is not directly contacting with the top sheet; and the liquid guide unit is configured for moving the urine from the position where the urine has collided with the liquid guide to other positions when urine is discharged;

side edge bands along ends of the side parts of the leak preventer, the side edge bands being directly connected to left and right ends of the liquid guide unit or being connected by a connection member such that the side bands are disposed on a same planar surface as the liquid guide unit or on the top surface of the liquid guide unit; and a support member for supporting the liquid guide unit from a lower surface of the liquid guide unit to make a space between the liquid guide unit and the absorber, the support member having a front end connected to a front end portion of the leak preventer, and a rear end connected at a position in vicinity of a central part of the top sheet in the front-rear direction or a position behind the central part of the top sheet in the front-rear direction.

26. The absorbent article according to claim 25, in which the liquid guide unit is in sheet-form.

27. The absorbent article according to claim 26, in which the liquid guide unit has a width of between 10 and 100 mm, length of between 20 and 200 mm, and thickness of between 0.1 and 2 mm.

28. The absorbent article according to claim 26, in which a part of a peripheral edge of the liquid guide unit is not connected to other portions of the absorbent article.

29. The absorbent article according to claim 26, in which the liquid guide unit is formed of a film having openings, the film having numerous openings.

30. The absorbent article according to claim 26, in which at least a part of the liquid guide unit has a cushioning property.

31. The absorbent article according to claim 30, in which the liquid guide unit is formed of a bulky nonwoven fabric.

32. The absorbent article according to claim 26, in which at least a part of the liquid guide unit has stretchability.

33. The absorbent article according to claim 32, in which the liquid guide unit is formed of a stretchable net.

34. The absorbent article according to claim 25, in which the liquid guide unit is formed of a molded foam body having a recessed surface on an upper side.

35. The absorbent article according to claim 25, in which a rear end of the liquid guide unit and the top sheet are connected.

36. The absorbent article according to claim 25, further including an urine/feces separating member in the vicinity of a central part in the front-rear direction of the leak preventer, the urine/feces separating member allowing a front body part of the internal space to function as an urine receiving part and a rear body part of the internal space to function as a feces receiving part.

37. The absorbent article according to claim 36, in which the urine/feces separating member and the liquid guide unit are connected.

38. The absorbent article according to claim 25, in which at least a part of the side edge bands has stretchability.

39. The absorbent article according to claim 25, in which the connection member for connecting the side edge bands and the left and right ends of the liquid guide unit has stretchability.

40. The absorbent article according to claim 25, wherein the support member is for supporting the liquid guide unit from a lower side.

41. The absorbent article according to claim 40, in which the absorber is a sheet-form absorber, the sheet-form absorber functioning as the support member.

42. The absorbent article according to claim 40, in which at least a part of the support member has stretchability.

43. The absorbent article according to claim 25, further including waist bands at a front end and a rear end of the leak preventer, the waist bands and the liquid guide unit being connected directly or by a connection member.

44. The absorbent article according to claim 43, in which the connection member for connecting the liquid guide unit and the waist bands has stretchability.

45. The absorbent article according to claim 25, in which the absorber is a super absorbent sheet containing the super absorbent polymer at greater than or equal to 50 wt %.

46. The absorbent article according to claim 26, in which a surface of the liquid guide unit is hydrophilic.

47. The absorbent article according to claim 29, in which the film having openings has liquid permeability.

48. The absorbent article according to claim 31, in which the bulky nonwoven fabric has liquid permeability.

49. The absorbent article according to claim 25, further including waist bands at a front end and a rear end of the leak preventer, at least one of the waist bands and the liquid guide unit being connected directly or by a connection member.

50. The absorbent article according to claim 49, where the at least one of the waist bands is a band at the front end of the leak preventer.

51. The absorbent article according to claim 5, in which the film has openings having a diameter of greater than or equal to 0.5 mm and introductory tubes.

* * * * *